United States Patent
Jones et al.

(10) Patent No.: US 9,833,466 B2
(45) Date of Patent: Dec. 5, 2017

(54) TREATMENT OF LEUKEMIA WITH HISTONE DEACETYLASE INHIBITORS

(71) Applicant: Acetylon Pharmaceuticals Inc., Boston, MA (US)

(72) Inventors: Simon S. Jones, Harvard, MA (US); Chengyin Min, Brookline, MA (US); Min Yang, Newton, MA (US); David Lee Tamang, Watertown, MA (US)

(73) Assignee: ACETYLON PHARMACEUTICALS, INC., Boston, MA (US)

(*) Notice: Subject to any disclaimer, the term of this patent is extended or adjusted under 35 U.S.C. 154(b) by 150 days.

(21) Appl. No.: 14/792,046

(22) Filed: Jul. 6, 2015

(65) Prior Publication Data
US 2016/0030458 A1 Feb. 4, 2016

Related U.S. Application Data

(60) Provisional application No. 62/147,218, filed on Apr. 14, 2015, provisional application No. 62/061,233, filed on Oct. 8, 2014, provisional application No. 62/021,473, filed on Jul. 7, 2014.

(51) Int. Cl.

| | | |
|---|---|---|
| *A61K 31/4045* | (2006.01) | |
| *A61K 31/706* | (2006.01) | |
| *A61K 45/06* | (2006.01) | |
| *A61K 31/505* | (2006.01) | |
| *A61K 31/5377* | (2006.01) | |
| *A61K 31/496* | (2006.01) | |
| *A61K 31/167* | (2006.01) | |
| *A61K 31/506* | (2006.01) | |

(52) U.S. Cl.
CPC .......... *A61K 31/706* (2013.01); *A61K 31/167* (2013.01); *A61K 31/4045* (2013.01); *A61K 31/496* (2013.01); *A61K 31/505* (2013.01); *A61K 31/506* (2013.01); *A61K 31/5377* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,549,633 A | 12/1970 | Grabowski et al. | |
| 6,777,217 B1 | 8/2004 | Schreiber et al. | |
| 7,244,853 B2 | 7/2007 | Schreiber et al. | |
| 7,250,504 B2 | 7/2007 | Grozinger et al. | |
| 7,501,417 B2 | 3/2009 | Van Emelen et al. | |
| 7,541,369 B2 | 6/2009 | Angibaud et al. | |
| 7,868,205 B2 | 1/2011 | Moradei et al. | |
| 7,994,362 B2 | 8/2011 | Schreiber et al. | |
| 8,119,685 B2 | 2/2012 | Heidebrecht et al. | |
| 8,148,526 B1 | 4/2012 | van Duzer et al. | |
| 8,394,810 B2 | 3/2013 | van Duzer et al. | |
| 8,524,711 B2 | 9/2013 | Angibaud et al. | |
| 8,598,168 B2 | 12/2013 | Moradei et al. | |
| 8,609,678 B2 | 12/2013 | van Duzer et al. | |
| 8,614,223 B2 | 12/2013 | van Duzer et al. | |
| 9,096,549 B2 | 8/2015 | van Duzer et al. | |
| 9,139,583 B2 | 9/2015 | van Duzer et al. | |
| 9,145,412 B2 | 9/2015 | van Duzer et al. | |
| 9,150,560 B2 | 10/2015 | Van Emelen et al. | |
| 2004/0266769 A1 | 12/2004 | Bressi et al. | |
| 2005/0096468 A1 | 5/2005 | Van Emelen et al. | |
| 2005/0119305 A1 | 6/2005 | Naka et al. | |
| 2006/0239909 A1 | 10/2006 | Anderson et al. | |
| 2007/0093413 A1 | 4/2007 | Schreiber et al. | |
| 2007/0149495 A1 | 6/2007 | Bressi et al. | |
| 2008/0039509 A1 | 2/2008 | Lu et al. | |
| 2008/0207590 A1 | 8/2008 | Deziel et al. | |
| 2009/0023786 A1 | 1/2009 | Miller et al. | |
| 2009/0124631 A1 | 5/2009 | Li et al. | |
| 2009/0209590 A1 | 8/2009 | Mazitschek et al. | |
| 2009/0305384 A1 | 12/2009 | Grozinger et al. | |
| 2009/0312363 A1 | 12/2009 | Bradner et al. | |

(Continued)

FOREIGN PATENT DOCUMENTS

| | | |
|---|---|---|
| EP | 2 524 918 A1 | 11/2012 |
| WO | 01/70675 A2 | 9/2001 |

(Continued)

OTHER PUBLICATIONS

Derissen, E. J., Beijnen, J. H., & Schellens, J. H. (2013). Concise drug review: azacitidine and decitabine. The oncologist, 18(5), 619-624.*
Abel et al. (2008) "Epigenetic targets of HDAC inhibition in neurodegenerative and psychiatric disorders," Curr. Opin. Pharmacol. 8(1):57-64.
Abujamra et al. (2010) "Histone deacetylase inhibitors: a new perspective for the treatment of leukemia," Leuk. Res. 34(6):687-695.
Alfonso R. Gennaro: Ed. (1970) Remington's Pharmaceutical Science. 17th Ed. Mack Publishing Co. Easton, Pennsylvania. p. 1418.
Angibaud et al. (2005) "Discovery of Pyrimidyl-5-hydroxamic acids as New Potent Histone Deacetylase Inhibitors," European Journal of Medicinal Chemistry. 40(6):597-606.
Berge et al. (1977) "Pharmaceutical salts," Journal of Pharmaceutical Sciences. 66:1-19.

(Continued)

*Primary Examiner* — Shaojia Anna Jiang
*Assistant Examiner* — Dale R Miller
(74) *Attorney, Agent, or Firm* — Lathrop Gage LLP; Brian C. Trinque

(57) ABSTRACT

Provided herein are combinations comprising an HDAC inhibitor and azacitidine for the treatment of leukemia in a subject in need thereof. Provided herein are combinations comprising an HDAC inhibitor and azacitidine for the treatment of acute myelogenous leukemia in a subject in need thereof. Also provided herein are methods for treating leukemia in a subject in need thereof, comprising administering to the subject an effective amount of the above combination or an HDAC inhibitor, as well as methods for treating acute myelogenous leukemia in a subject in need thereof, comprising administering to the subject an effective amount of the above combination or an HDAC inhibitor.

10 Claims, 37 Drawing Sheets

(56) References Cited

U.S. PATENT DOCUMENTS

| | | |
|---|---|---|
| 2010/0137196 A1 | 6/2010 | Schreiber et al. |
| 2010/0152254 A1 | 6/2010 | Bialer et al. |
| 2010/0168463 A1 | 7/2010 | Hirata et al. |
| 2010/0317678 A1 | 12/2010 | Moffat et al. |
| 2010/0330197 A1 | 12/2010 | Higashiguchi et al. |
| 2011/0218154 A1 | 9/2011 | Schreiber et al. |
| 2011/0300134 A1 | 12/2011 | van Duzer et al. |
| 2012/0094927 A1 | 4/2012 | Stam et al. |
| 2012/0121502 A1 | 5/2012 | van Duzer et al. |
| 2013/0225543 A1 | 8/2013 | Jones et al. |
| 2014/0011767 A1 | 1/2014 | Yang et al. |
| 2014/0128391 A1 | 5/2014 | van Duzer et al. |
| 2014/0142104 A1 | 5/2014 | van Duzer et al. |
| 2014/0142117 A1 | 5/2014 | van Duzer et al. |
| 2014/0357512 A1 | 12/2014 | Jones et al. |
| 2015/0045380 A1 | 2/2015 | van Duzer et al. |
| 2015/0099744 A1 | 4/2015 | Yang et al. |
| 2015/0105358 A1 | 4/2015 | Quayle et al. |
| 2015/0105383 A1 | 4/2015 | Quayle et al. |
| 2015/0105384 A1 | 4/2015 | Jones et al. |
| 2015/0105409 A1 | 4/2015 | Quayle et al. |
| 2015/0150871 A1 | 6/2015 | Quayle et al. |
| 2015/0176076 A1 | 6/2015 | Yang et al. |
| 2015/0239869 A1 | 8/2015 | Mazitschek et al. |
| 2015/0299130 A1 | 10/2015 | van Duzer et al. |

FOREIGN PATENT DOCUMENTS

| | | |
|---|---|---|
| WO | 02/074298 A1 | 9/2002 |
| WO | 03/037869 A1 | 5/2003 |
| WO | 03/076401 A1 | 9/2003 |
| WO | 03/076430 A1 | 9/2003 |
| WO | 03/087057 A1 | 10/2003 |
| WO | 2004/052869 A1 | 6/2004 |
| WO | 2005/012261 A1 | 2/2005 |
| WO | 2005/028447 A1 | 3/2005 |
| WO | 2005/030704 A1 | 4/2005 |
| WO | 2005/030705 A1 | 4/2005 |
| WO | 2006/102557 A2 | 9/2006 |
| WO | 2006/123121 A1 | 11/2006 |
| WO | 2007/022638 A1 | 3/2007 |
| WO | 2007/091703 A2 | 8/2007 |
| WO | 2007/130429 A2 | 11/2007 |
| WO | 2007/144341 A1 | 12/2007 |
| WO | 2008/003801 A1 | 1/2008 |
| WO | 2008/033746 A2 | 3/2008 |
| WO | 2008/055068 A2 | 5/2008 |
| WO | 2008/091349 A1 | 7/2008 |
| WO | 2008/111299 A1 | 9/2008 |
| WO | 2009/137462 A1 | 11/2009 |
| WO | 2009/137503 A1 | 11/2009 |
| WO | 2010/009155 A2 | 1/2010 |
| WO | 2010/011296 A2 | 1/2010 |
| WO | 2010/080996 A1 | 7/2010 |
| WO | 2010/131922 A2 | 11/2010 |
| WO | 2011/011186 A1 | 1/2011 |
| WO | 2011/019393 A2 | 2/2011 |
| WO | 2011/084991 A2 | 7/2011 |
| WO | 2011/091213 A2 | 7/2011 |
| WO | 2011/146855 A1 | 11/2011 |
| WO | 2012/068109 A2 | 5/2012 |
| WO | 2012/098132 A1 | 7/2012 |
| WO | 2013/013113 A2 | 1/2013 |

OTHER PUBLICATIONS

Bertrand et al. (2010) "Inside HDAC with HDAC inhibitors," European Journal of Medicinal Chemistry. 45:2095-2116.
Bradner (Jan. 28, 2010) "Chemical genetic strategy identifies histone deacetylase 1 (HDAC1) and HDAC2 as therapeutic targets in sickle cell disease," Proc. Natl. Acad. Sci. USA. 107(28):12617-22.
Brana et al. (2002) "Synthesis and biological evaluation of novel 2-(1H-1-imidazol-4-yl)cyclopropane carboxylic acids: key intermediates for H3 histamine receptor ligands," BioOrganic & Medicinal Chemistry Letter. 12(24):3561-3563.
Broxterman et al. (1992) "Synthesis of (optically active) sulfur-containing trifunctional amino acids by radical addition to (optically active) unsaturated amino acids," The Journal of Organic Chemistry. 57(23):6286-6294.
Butler et al. (2000) "Suberoylanilide Hydroxamic Acid, an Inhibitor of Histone Deactylase, Suppresses the Growth of Prostate Cancer Cells in Vitro and in Vivo," Cancer Research. 60:5165-5170.
Carey et al. (2006) "Histone deacetylase inhibitors: gathering pace," Current Opinion in Pharmacology. 6:369-375.
Chuang et al. (2009) "Multiple roles of HDAC inhibition in neurodegenerative conditions," Trends in Neurosciences. 32 (11):591-601.
Costello et al. (Dec. 2012) "Evidence for Changes in RREB-1, ZIP3, and Zinc in the Early Development of Pancreatic Adenocarcinoma," J. Gastrointest. Canc. 43:570-578.
Dallavalle et al. (2012) "Development and therapeutic impact of HDAC6-selective inhibitors," Biochemical Pharmacology. 84:756-765.
Dokmanovic et al. (2007) "Histone Deacetylase Inhibitors: Overview and Perspectives," Mol. Cancer Res. 5 (10):981-989.
Elaut et al. (2007) "The Pharmaceutical Potential of Histone Deacetylase Inhibitors," Current Pharmaceutical Design. 13:2584-2620.
Fischer et al. (2010) "Targeting the correct HDAC(s) to treat cognitive disorders," Trends in Pharmacological Sciences. 31(12):605-617.
Foks et al. (1972) "Investigations on Pyrazine Derivatives Part II. Synthesis and Tuberculostatic Action of Some 6Alkylaminopyrazine-2-carboxylic acids," Dissertationes Pharmaceuticae and Pharmacologicae. 24:(6)577-583.
Foks et al. (1974) "Studies on Pyrazine Derivatives," Pol. J. Pharmacol. Pharm. 26:537-543.
Giannini et al. (Jul. 2012) "Histone Deacetylase Inhibitors in the Treatment of Cancer: Overview and Perspectives," Future Med. Chem. 4(11):1439-1460.
Graff (Feb. 29, 2012) "An epigenetic blockade of cognitive functions in the neurodegenerating brain," Nature. 483 (7388):222-226.
Grozinger et al. (1999) "Three proteins define a class of human histone deacetylases related to yeast Hda1p," Proc. Natl. Acad. Sci. USA. 96:4868-4873.
Guan (2009) "HDAC2 negatively regulates memory formation and synaptic plasticity," Nature. 459(7243):55-60.
Haggarty et al. (2003) "Domain-selective Small-molecule Inhibitor of Histone Deacetylase 6 (HDAC6)-mediated Tubulin Deacetylation," Proc. Natl. Acad. Sci. USA. 100(8):4389-4394.
Hassig et al. (1997) "Nuclear histone acetylases and deacetylases and transcriptional regulation: HATs off to HDACs," Curr. Opin. Chem. Biol. 1:300-308.
Hu et al. (2000) "Cloning and characterization of a novel human class I histone deacetylase that functions as a transcription repressor," J. Biol. Chem. 275:15254-15264.
Johnstone et al. (2002) "Histone-deacetylase inhibitors: novel drugs for the treatment of cancer," Nature Reviews in Drug Discovery. 1:287-299.
Kao et al. (2000) "Isolation of a novel histone deacetylase reveals that class I and class II deacetylases promote SMRT-mediated repression," Genes Dev. 14:55-66.
Kim et al. (2011) "Histone deacetylase inhibitors: molecular mechanisms of action and clinical trials as anti-cancer drugs," Am. J. Transl. Res. 3:166-179.
Kim et al. (Aug. 22, 2012) "HDAC6 Inhibitor Blocks Amyloid Beta-Induced Impairment of Mitochondrial Transport in Hippocampal Neurons," PLoS ONE. 7(8): e42983.
Kozikowski et al. (2008) "Use of the Nitrile Oxide Cycloaddition (NOC) Reaction for Molecular Probe Generation: A New Class of Enzyme Selective Histone Deacetylase Inhibitors (HDACIs) Showing Picomolar Activity at HDAC6," Journal of Medicinal Chemistry. 51:4370-4373.
Lane et al. (2009) "Histone Deacetylase Inhibitors in Cancer Therapy," J. Clin. Oncol. 27:5459-5468.

(56) References Cited

OTHER PUBLICATIONS

Loudni et al. (2007) "Design, synthesis and biological evaluation of 1, 4-benzodiazepine-2, 5-dione-based HDAC inhibitors," Bioorganic and Medicinal Chemistry Letters. 17:4819-4823.
Marks et al. (2001) "Histone deacetylases and cancer: causes and therapies," Nat. Rev. Cancer. 1:194-202.
Mazitschek et al. (2008) "Development of a Fluorescence Polarization Based Assay for Histone Deacetylase Ligand Discovery," Bioorganic and Medicinal Chemistry Letters. 18(9):2809-2812.
Miller et al. (1998) "Paclitaxel as the Initial Treatment of Multiple Myeloma: An Eastern Cooperative Oncology Group Study (E1A93)," Am. J. Clin. Oncol. 21(6):553-556.
Morris (Apr. 10, 2013) "Loss of histone deacetylase 2 improves working memory and accelerates extinction learning," J. Neurosci. 33(15):6401-6411.
Neidle, Stephen: Ed. (2008) Cancer Drug Design and Discovery. Elsevier/Academic Press. pp. 427-431.
Pellicciari et al. (1996) "Synthesis and Pharmacological Characterization of AII Sixteen Stereoisomers of 2-(2'-Carboxy-3'-phenylcyclopropyl)glycine. Focus on (2S,1'S,2'S,3'R)-2-(2'-Carboxy-3'-phenylcyclopropyl)glycine, a Novel and Selective Group II Metabotropic Glutamate Receptors Antagonist," Journal of Medicinal Chemistry. 39 (11):2259-2269.
Perez (1998) "Paclitaxel in Breast Cancer," The Oncologist. 3:373-389.
Rajak et al. (2011) "2,5-Disubstituted-1,3,4-oxadiazoles/thiadiazole as Surface Recognition Moiety: Design and Synthesis of Novel Hydroxamic acid Based Histone Deacetylase Inhibitors," Bioorganic & Medicinal Chemistry Letters. 21(19):5735-5738.
Richon et al. (2009) "Development of vorinostat: Current applications and future perspectives for cancer therapy," Cancer Letters. 280:201-210.
Ropero et al. (2007) "The Role of Histone Deacetylases (HDACs) in Human Cancer," Molecular Oncology. 1:19-25.
Simoes-Peres et al. (Jan. 29, 2013) "HDAC6 as a target for neurodegenerative diseases: what makes it different from the other HDACs," Mol. Neurodegener. 8:7.
Smil et al. (2009) "Novel HDAC6 Isoform Selective Chiral Small Molecule Histone Deacetylase Inhibitors," Bioorganic and Medicinal Chemistry Letters. 19:688-692.
Sporn et al. (2000) "Chemoprevention of Cancer," Carcinogenesis. 21(3):525-530.
Stilling et al. (2011) "The role of histone acetylation in age-associated memory impairment and Alzheimer's disease," Neurobiology of Learning. 96:19-26.
Sung et al. (Oct. 11, 2012) "Mercaptoacetamide-based class II HDAC inhibitor lowers Aβ levels and improves learning and memory in a mouse model of Alzheimer's disease," Experimental Neurology. 239:192-201.
Taunton et al. (1996) "A mammalian histone deacetylase related to the yeast transcriptional regulator Rpd3p," Science. 272:408-411.
Thoppil et al. (Sep. 2011) "Terpenoids as Potential Chemopreventive and Therapeutic Agents in Liver Cancer," World J. Hepatol. 3(9):228-249.
Venter et al. (2001) "The sequence of the human genome," Science. 291:1304-1351.
Walbrick et al.(1968) "A general method for synthesizing optically active 1,3-disubstituted allene hydrocarbons," The Journal of the American Chemical Society. 90(11):2895-2901.
Warner et al. (1992) "Electron demand in the transition state of the cyclopropylidene to allene ring opening," The Journal of Organic Chemistry. 57(23):6294-6300.
Warrell et al. (1998) "Therapeutic targeting of transcription in acute promyelocytic leukemia by use of an inhibitor of histone deacetylase," J. Natl. Cancer Inst. 90:1621-1625.
Weichert (2009) "HDAC expression and clinical prognosis in human malignancies," Cancer Letters. 280:168-176.
Witt et al. (2009) "HDAC family: What are the cancer relevant targets?" Cancer Letters. 277:8-21.
Xiong et al. (Mar. 4, 2013) "HDAC6 mutations rescue human tau-induced microtubule defects in Drosophila," Proc. Natl. Acad. Sci. U S A. 110(12):4604-4609.
Yang et al. (1997) "Isolation and characterization of cDNAs corresponding to an additional member of the human histone deacetylase gene family," J. Biol. Chem. 272:28001-28007.
Zhou et al. (2001) "Cloning and characterization of a histone deacetylase, HDAC9," Proc. Natl. Acad. Sci. USA. 98:10572-10577.
International Preliminary Report on Patentability corresponding to International Patent Application No. PCT/US2011/060791, dated Jul. 22, 2014.
International Search Report with Written Opinion corresponding to International Patent Application No. PCT/US2011/021982, dated Oct. 10, 2011.
International Search Report with Written Opinion corresponding to International Patent Application No. PCT/US2011/060791, dated Mar. 5, 2014.
International Search Report with Written Opinion corresponding to International Patent Application No. PCT/US2014/059863, dated Feb. 19, 2015.
International Search Report with Written Opinion corresponding to International Patent Application No. PCT/US2015/039225, dated Oct. 29, 2015.
Search Opinion corresponding to European Patent Application No. 11735212, dated Jun. 26, 2014.
Supplementary European Search Report corresponding to European Application No. 11840803.8, dated Mar. 5, 2014.
Written Opinion corresponding to Singapore Patent Application No. Application No. 201205393-0, dated Nov. 15, 2013.

* cited by examiner

Compound E (µM)

Azacytidine (uM)

6 primary AML samples primary AML sample 184090514 primary AML sample 103113SH

MV4-11 cell line

TREATMENT OF LEUKEMIA WITH HISTONE DEACETYLASE INHIBITORS

CROSS-REFERENCE TO RELATED APPLICATIONS

This application is related to U.S. Provisional Application No. 62/021,473, filed Jul. 7, 2014, U.S. Provisional Application No. 62/061,233, filed Oct. 8, 2014, and U.S. Provisional Application No. 62/147,218, filed Apr. 14, 2015. The contents of each of these applications are incorporated herein by reference in their entirety.

BACKGROUND

Cancer is distinguished by uncontrolled proliferation of cells. The cellular components of blood originate from pluripotent hematopoietic stem cells. Via their regenerative and differentiating capacities, stem cells generate lymphoid and myeloid precursors, which then produce lymphocytes, neutrophils, eosinophils, basophils, erythrocytes, and platelets. In leukemia, high levels of immature white blood cells, or blasts, are present. Four main types of leukemia are recognized: acute lymphoblastic leukemia (ALL), acute myeloid leukemia (AML), chronic lymphocytic leukemia (CLL) and chronic myeloid leukemia (CML); although less common types are known as well.

Leukemia has an average 5-year mortality rate of 40%, and in 2012 developed in over 350,000 people globally. Therefore, there remains a continued and urgent need for therapies directed toward treatment of leukemia.

SUMMARY

In one aspect, provided herein is a pharmaceutical combination for treating leukemia, comprising a therapeutically effective amount of a histone deacetylase (HDAC) inhibitor or a pharmaceutically acceptable salt thereof, and azacitidine or a pharmaceutically acceptable salt thereof. In one embodiment, the HDAC inhibitor is an HDAC6-specific inhibitor. In another embodiment, the HDAC inhibitor is an HDAC1/2-specific inhibitor. In another embodiment, the HDAC inhibitor is an HDAC1/2/6-specific inhibitor.

In an embodiment, the HDAC6-specific inhibitor is a compound of Formula I:

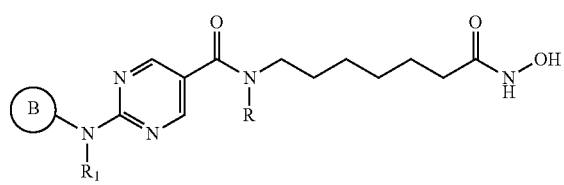

(I)

or a pharmaceutically acceptable salt thereof.

In another embodiment, the HDAC6-specific inhibitor is a compound of Formula II:

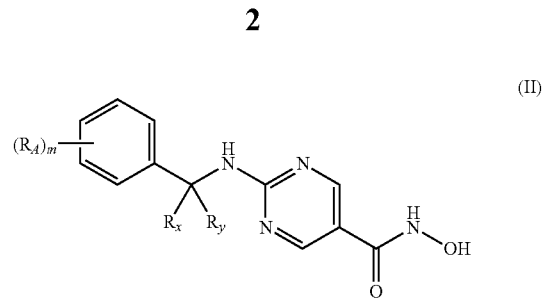

(II)

or a pharmaceutically acceptable salt thereof.

In another embodiment, the HDAC1/2-specific inhibitor is a compound of Formula III:

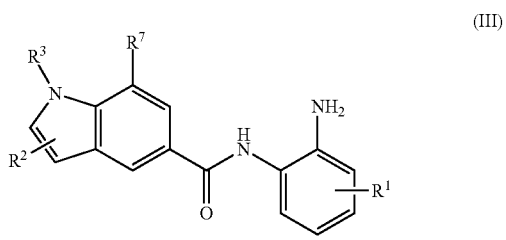

(III)

or a pharmaceutically acceptable salt thereof.

In another embodiment, the HDAC inhibitor is:

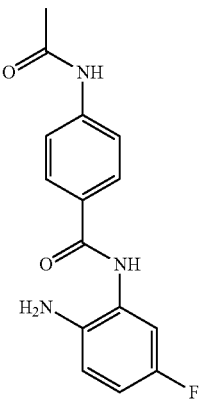 [SMILES: CC(=O)Nc1ccc(C(=O)Nc2cc(F)ccc2N)cc1]

or a pharmaceutically acceptable salt thereof.

In another embodiment, the HDAC1/2/6-specific inhibitor is a compound of Formula IV:

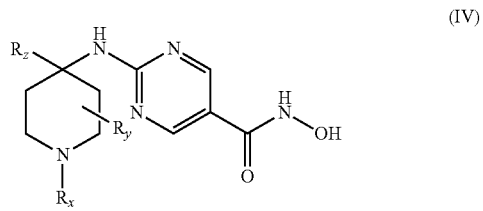

(IV)

or a pharmaceutically acceptable salt thereof.

In another embodiment, the combination further comprises a pharmaceutically acceptable carrier.

In another aspect, provided herein is a method for treating leukemia in a subject in need thereof comprising administering to the subject a therapeutically effective amount of a pharmaceutical combination comprising a histone deacetylase (HDAC) inhibitor or a pharmaceutically acceptable salt thereof, and azacitidine or a pharmaceutically acceptable salt thereof. In one embodiment, the HDAC inhibitor is an HDAC6-specific inhibitor. In another embodiment, the HDAC inhibitor is an HDAC1/2-specific inhibitor. In another embodiment, the HDAC inhibitor is an HDAC1/2/6-specific inhibitor.

In yet another embodiment, the HDAC6-specific inhibitor is a compound of Formula I:

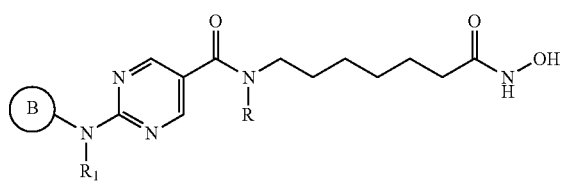

(I)

or a pharmaceutically acceptable salt thereof.

In another embodiment, the HDAC6-specific inhibitor is a compound of Formula II:

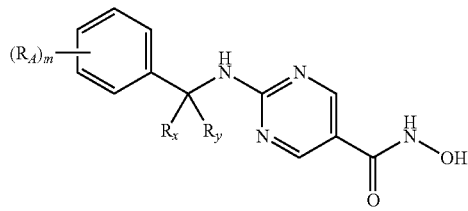

(II)

or a pharmaceutically acceptable salt thereof,

In another embodiment, the HDAC1/2-specific inhibitor is a compound of Formula III:

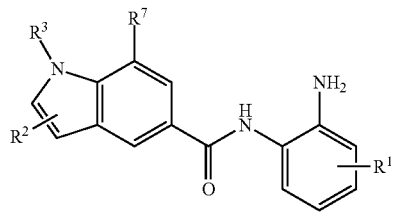

(III)

or a pharmaceutically acceptable salt thereof.

In another embodiment, the HDAC inhibitor is:

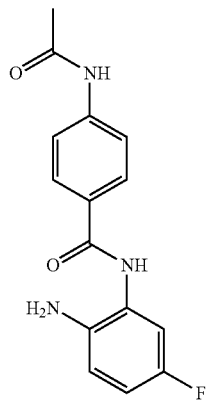 [SMILES: CC(=O)Nc1ccc(C(=O)Nc2cc(F)ccc2N)cc1]

or a pharmaceutically acceptable salt thereof.

In another embodiment, the HDAC1/2/6-specific inhibitor is a compound of Formula IV:

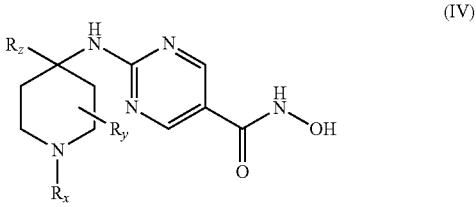

(IV)

or a pharmaceutically acceptable salt thereof.

In another aspect, provided herein is a method for treating acute myelogenous leukemia in a subject in need thereof comprising administering to the subject a therapeutically effective amount of a compound of Formula I:

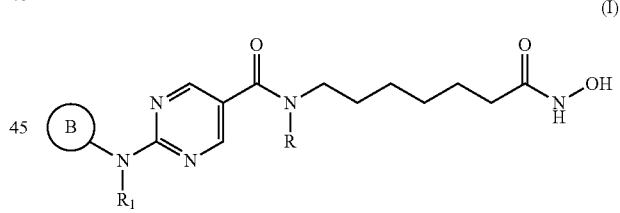

(I)

or a pharmaceutically acceptable salt thereof.

In another aspect, provided herein is a method for treating acute myelogenous leukemia in a subject in need thereof comprising administering to the subject a therapeutically effective amount of a compound of Formula II:

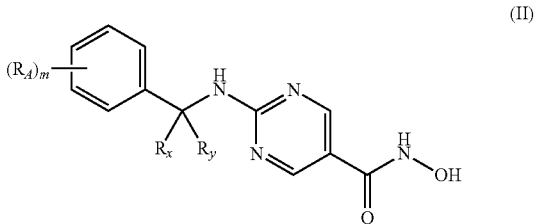

(II)

or a pharmaceutically acceptable salt thereof.

In another aspect, provided herein is a method for treating acute myelogenous leukemia in a subject in need thereof comprising administering to the subject a therapeutically effective amount of a compound of Formula III:

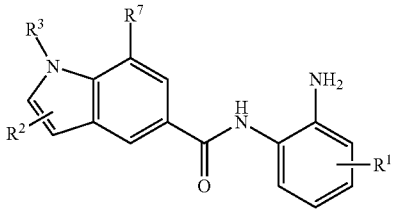

(III)

or a pharmaceutically acceptable salt thereof.

In another aspect, provided herein is a method for treating acute myelogenous leukemia in a subject in need thereof comprising administering to the subject a therapeutically effective amount of the compound:

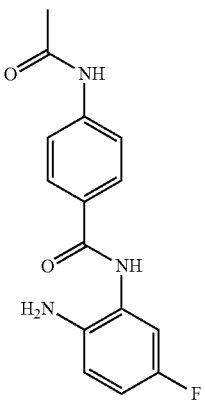

or a pharmaceutically acceptable salt thereof.

In another aspect, provided herein is a method for treating acute myelogenous leukemia in a subject in need thereof comprising administering to the subject a therapeutically effective amount of a compound of Formula IV:

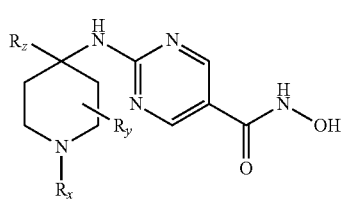

(IV)

or a pharmaceutically acceptable salt thereof.

In an embodiment, the compound of Formula IV is:

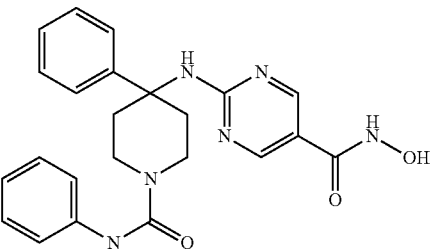

or a pharmaceutically acceptable salt thereof.

In another aspect, provided herein is a method for treating acute myelogenous leukemia in a subject in need thereof comprising administering to the subject a therapeutically effective amount of a HDAC1/2-specific inhibitor.

In yet another aspect, provided herein is a method for treating acute myelogenous leukemia in a subject in need thereof comprising administering to the subject a therapeutically effective amount of a HDAC1/2/6-specific inhibitor.

BRIEF DESCRIPTION OF THE FIGURES

FIG. 1A shows data for azacitidine and Compound A on HL-60 cells, FIG. 1B shows data for azacitidine and Compound C on HL-60 cells, FIG. 1C shows data for azacitidine and Compound E on HL-60 cells, and FIG. 1D shows data for azacitidine and Compound F on HL-60 cells.

FIGS. 2A-C show data for the Kasumi-1 cell cycle at 72 hours. FIG. 2A shows data for Compound B, FIG. 2B shows data for Compound G, and FIG. 2C shows data for Compound E. FIG. 2D shows pictures of gels and the expression of the fusion protein AML1/ETO or ACTB. Data is shown for Compound A and panobinostat.

In FIGS. 4A-C, surface levels of the myeloid differentiation marker CD11b were determined. In FIGS. 4D-F, apoptosis was assessed by flow cytometry by measuring Annexin V binding and cellular permeability to propidium iodide at 96 hours post-treatment. The relative fraction of cells that were alive, in early apoptosis, in late apoptosis, or dead was then determined.

FIG. 9A shows surface levels of myeloid differentiation marker CD11b, determined by FACS at 72 h post-treatment. Compound E, Compound H, Compound A, and Compound G increased the percentage of CD11b positive cells. Compound C had no effect. FIG. 9B shows assessment of the cell cycle by flow cytometry after incorporation of EdU and staining with Far Red at 72 h post-treatment. The distribution of cells among G0/G1 phase, G2/M phase, S phase and subG1 phase was determined. FIG. 9C shows the assessment of apoptosis by flow cytometry via measuring Annexin V binding and cellular permeability to propidium iodide at 96 h post-treatment. The relative fraction of cells that were live, in early apoptosis, in late apoptosis, or dead was then determined.

FIGS. 10A, 10C, and 10E show surface levels of myeloid differentiation marker CD11b determined by FACS at 72 h post-treatment. FIGS. 10B, 10D, and 10F show the assessment of apoptosis by FACS at 96 h post-treatment (see, e.g., FIG. 9C).

FIGS. 12A, 12C, and 12E show surface levels of CD11b determined by FACS at 72 h post-treatment. FIGS. 12B, 12D, and 12F show assessment of apoptosis by FACS at 96 h post-treatment.

DETAILED DESCRIPTION

Figure 1A:
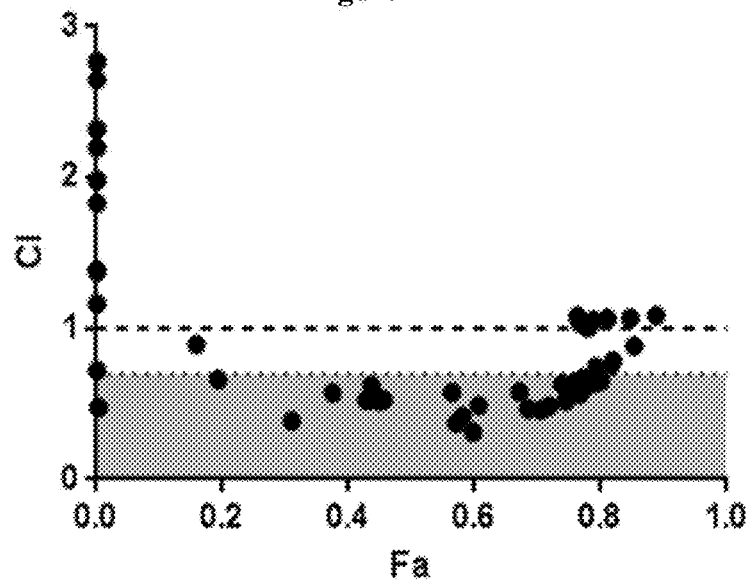
FIGS. 1A-D are a set of four graphs that show synergy of HDAC inhibitors and azacitidine on AML cells. Each of the graphs shows the CI values plotted as a function of Fa.
Figure 1B:
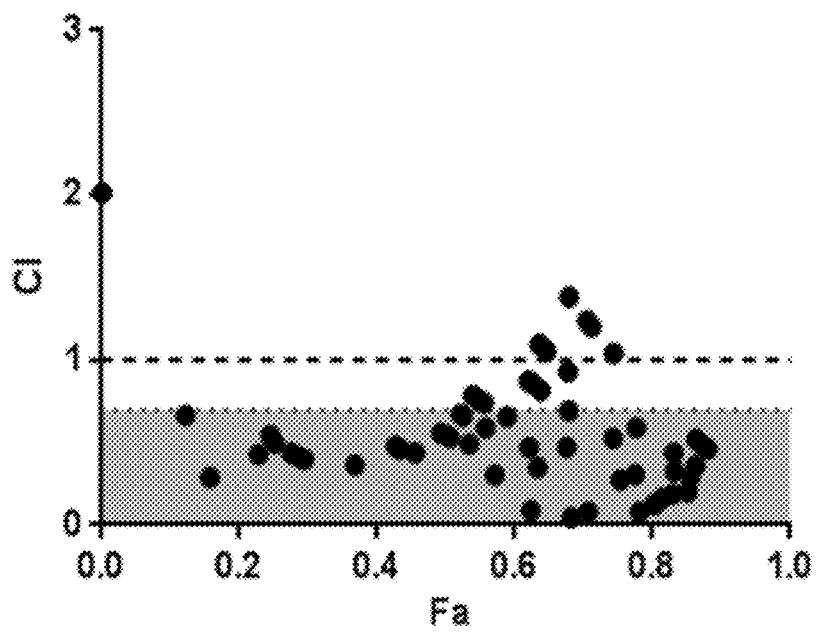
Figure 1C:
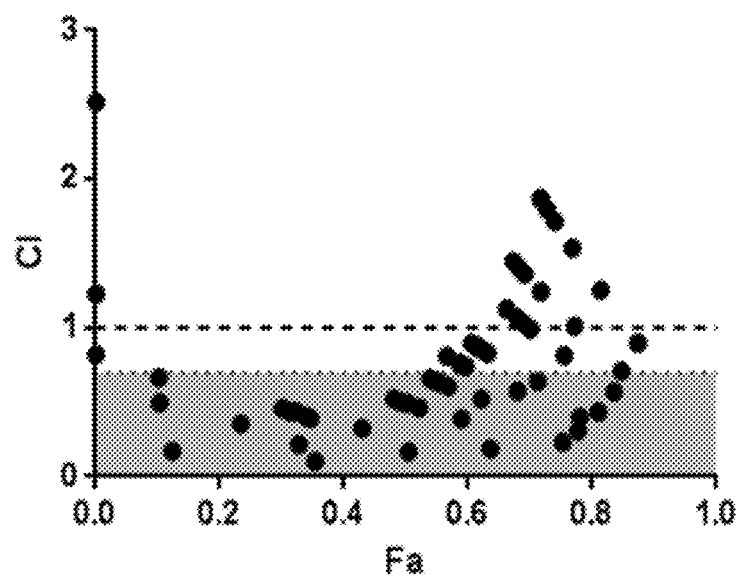
Figure 1D:
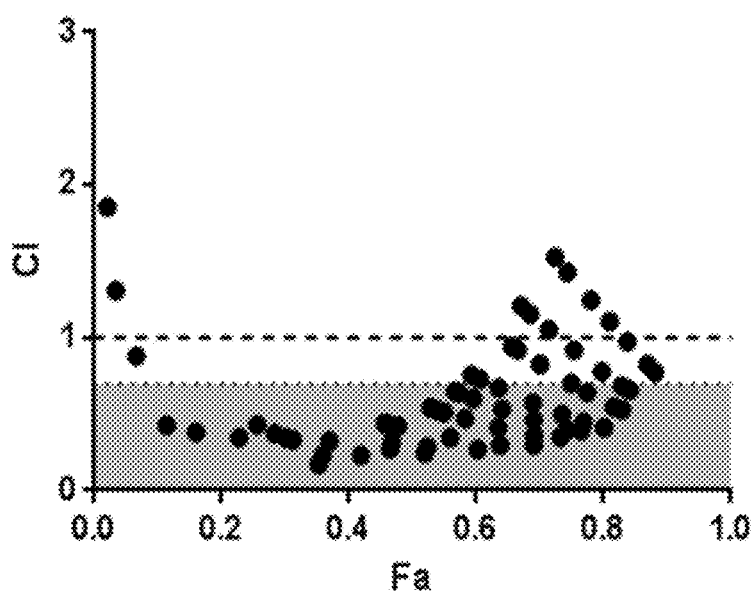

Provided herein are combinations comprising an HDAC inhibitor and azacitidine for the treatment of leukemia in a subject in need thereof. Also provided herein are combinations comprising an HDAC inhibitor and azacitidine for the treatment of acute myelogenous leukemia in a subject in need thereof. Also provided herein are methods for treating leukemia in a subject in need thereof, comprising administering to the subject an effective amount of an HDAC inhibitor, or alternatively administering the above combination comprising an HDAC inhibitor and azacitidine. Provided herein are methods for treating acute myelogenous leukemia in a subject in need thereof, comprising administering to the subject an effective amount of an HDAC inhibitor, or alternatively administering the above combination comprising an HDAC inhibitor and azacitidine.

Definitions

Listed below are definitions of various terms used herein. These definitions apply to the terms as they are used throughout this specification and claims, unless otherwise limited in specific instances, either individually or as part of a larger group.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "alkyl" refers to saturated, straight- or branched-chain hydrocarbon moieties containing, in certain embodiments, between one and six ($C_{1-6}$ alkyl), or one and eight carbon atoms ($C_{1-8}$ alkyl), respectively. Examples of $C_{1-6}$ alkyl moieties include, but are not limited to, methyl, ethyl, propyl, isopropyl, n-butyl, tert-butyl, neopentyl, n-hexyl moieties; and examples of $C_{1-8}$ alkyl moieties include, but are not limited to, methyl, ethyl, propyl, isopropyl, n-butyl, tert-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "alkoxy" refers to an —O-alkyl moiety.

The terms "cycloalkyl" or "cycloalkylene" denote a monovalent group derived from a monocyclic or polycyclic saturated or partially unsaturated carbocyclic ring compound. Examples of $C_{3-8}$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but are not limited to, cyclopropyl, cyclobutyl, cyclopentyl, cyclohexyl, bicyclo[2.2.1]heptyl, and bicyclo[2.2.2]octyl. Also contemplated are groups derived from a monocyclic or polycyclic carbocyclic ring compound having at least one carbon-carbon double bond. Examples of such groups include, but are not limited to, cyclopropenyl, cyclobutenyl, cyclopentenyl, cyclohexenyl, cycloheptenyl, cyclooctenyl, and the like. In some embodiments, cycloalkyl groups have from three to six carbon atoms ($C_{3-6}$ cycicoalkyl). In some embodiments, cycloalkyl groups have from three to eight carbon atoms ($C_{3-8}$ cycicoalkyl).

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl and the like. In some embodiments, aryl groups have six carbon atoms. In some embodiments, aryl groups have from six to ten carbon atoms ($C_{6-10}$-aryl). In some embodiments, aryl groups have from six to sixteen carbon atoms ($C_{6-16}$-aryl).

The term "heteroaryl" refers to a mono- or poly-cyclic (e.g., bi-, or tri-cyclic or more) fused or non-fused, moieties or ring system having at least one aromatic ring, having from five to ten ring atoms of which one ring atom is selected from S, O, N and Si; zero, one or two ring atoms are additional heteroatoms independently selected from S, O, N and Si; and the remaining ring atoms are carbon. Heteroaryl includes, but is not limited to pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "halo" refers to a halogen, such as fluorine, chlorine, bromine, and iodine.

The term "alkenyl" denotes a monovalent group derived from a hydrocarbon moiety containing, in certain embodiments, from two to six ($C_{2-6}$ alkenyl), or two to eight carbon atoms having at least one carbon-carbon double bond ($C_{2-8}$ alkenyl). The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "cycloalkyl" denotes a monovalent group derived from a monocyclic or polycyclic saturated or partially unsaturated carbocyclic ring compound. Examples of $C_{3-8}$-cycloalkyl include, but are not limited to, cyclopropyl, cyclobutyl, cyclopentyl, cyclohexyl, cyclopentyl and cyclooctyl; and examples of $C_{3-12}$-cycloalkyl include, but are not limited to, cyclopropyl, cyclobutyl, cyclopentyl, cyclohexyl, bicyclo[2.2.1]heptyl, and bicyclo[2.2.2]octyl. Also contemplated are groups derived from a monocyclic or polycyclic carbocyclic ring compound having at least one carbon-carbon double bond. Examples of such groups include, but are not limited to, cyclopropenyl, cyclobutenyl, cyclopentenyl, cyclohexenyl, cycloheptenyl, cyclooctenyl, and the like. In some embodiments, cycloalkyl groups have from three to six carbon atoms ($C_{3-6}$ cycicoalkyl). In some embodiments, cycloalkyl groups have from three to eight carbon atoms ($C_{3-8}$ cycicoalkyl).

The term "heterocycloalkyl" refers to a non-aromatic 3-, 4-, 5-, 6- or 7-membered ring or a bi- or tri-cyclic group fused or non-fused system, where (i) each ring contains between one and three heteroatoms independently selected from oxygen, sulfur, and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In an embodiment, the heterocycloalkyl group is a 4-7, e.g., 4-6, membered ring.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "HDAC6-specific" means that the compound binds to HDAC6 to a substantially greater extent, such as 5×, 10×, 15×, 20× greater or more, than to any other type of HDAC enzyme, such as HDAC1 or HDAC2. That is, the compound is selective for HDAC6 over any other type of HDAC enzyme. For example, a compound that binds to HDAC6 with an $IC_{50}$ of 10 nM and to HDAC1 with an $IC_{50}$ of 50 nM is HDAC6-specific. On the other hand, a compound that binds to HDAC6 with an $IC_{50}$ of 50 nM and to HDAC1 with an $IC_{50}$ of 60 nM is not HDAC6-specific.

The term "HDAC1/2-specific" means that the compound binds to HDAC1 and HDAC2 to a substantially greater extent, such as 5×, 10×, 15×, 20× greater or more, than to any other type of HDAC enzyme, such as HDAC3 or HDAC6. That is, the compound is selective for HDAC1 and HDAC2 over any other type of HDAC enzyme. For example, a compound that binds to HDAC1 and HDAC2 with an $IC_{50}$ of 10 nM and to HDAC3 with an $IC_{50}$ of 50 nM is HDAC1/2-specific. On the other hand, a compound that binds to HDAC1 and HDAC2 with an $IC_{50}$ of 50 nM and to HDAC3 with an $IC_{50}$ of 60 nM is not HDAC1/2-specific.

The term "HDAC1/2/6-specific" means that the compound binds to HDAC1, HDAC2 and HDAC6 to a substantially greater extent, such as 5×, 10×, 15×, 20× greater or more, than to any other type of HDAC enzyme, such as HDAC3. That is, the compound is selective for HDAC1, HDAC2 and HDAC6 over any other type of HDAC enzyme. For example, a compound that binds to HDAC1, HDAC2 and HDAC6 with an $IC_{50}$ of 10 nM and to HDAC3 with an $IC_{50}$ of 50 nM is HDAC1/2-specific. On the other hand, a compound that binds to HDAC1, HDAC2 and HDAC6 with an $IC_{50}$ of 50 nM and to HDAC3 with an $IC_{50}$ of 60 nM is not HDAC1/2-specific.

The term "combination" refers to two or more therapeutic agents to treat a therapeutic condition or disorder described in the present disclosure. Such combination of therapeutic agents may be in the form of a single pill, capsule, or intravenous solution. However, the term "combination" also encompasses the situation when the two or more therapeutic agents are in separate pills, capsules, or intravenous solutions. Likewise, the term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, or in separate containers (e.g., capsules) for each active ingredient. In addition, such administration also encompasses use of each type of therapeutic agent in a sequential manner, either at approximately the same time or at different times. In either case, the treatment regimen will provide beneficial effects of the drug combination in treating the conditions or disorders described herein.

The term "leukemia" refers to a hematologic malignancy. The term "leukemia" includes but is not limited to acute lymphoblastic leukemia (ALL), acute myelogenous leukemia (AML), chronic lymphocytic leukemia (CLL), chronic myelogenous leukemia (CML), acute monocytic leukemia (AML), biphenotypic acute leukemia (BAL), hairy cell leukemia (HCL), or acute promyelocytic leukemia (APL).

As used herein, the term "CD11b-expressing" refers to the expression of Cluster of Differentiation Molecule 11B (CD11b).

The term "inhibitor" is synonymous with the term antagonist.

Histone Deacetylase (HDAC) Inhibitors

Provided herein are methods for treating leukemia in a subject in need thereof. Also provided herein are pharmaceutical combinations for the treatment of leukemia (e.g., AML) in a subject in need thereof.

The combinations and methods provided herein comprise a histone deacetylase (HDAC) inhibitor. The HDAC inhibitor can be any HDAC inhibitor. Thus, the HDAC inhibitor may be selective or non-selective to a particular type of histone deacetylase enzyme. Preferably, the HDAC inhibitor is a selective HDAC inhibitor. More preferably, the HDAC inhibitor is an HDAC6-specific inhibitor, an HDAC1/2-specific inhibitor, or an HDAC1/2/6-specific inhibitor.

In some embodiments, the HDAC6-specific inhibitor is a compound of Formula I:

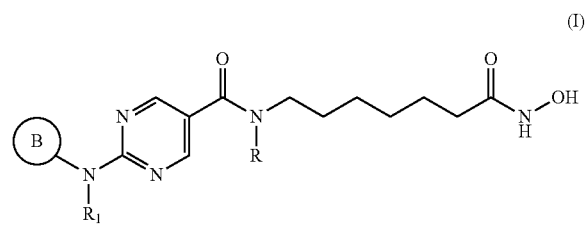

or a pharmaceutically acceptable salt thereof, wherein, ring B is aryl or heteroaryl;

$R_1$ is an aryl or heteroaryl, each of which may be optionally substituted by OH, halo, or $C_{1-6}$-alkyl; and R is H or $C_{1-6}$-alkyl.

Representative compounds of Formula I include, but are not limited to:

Compound A

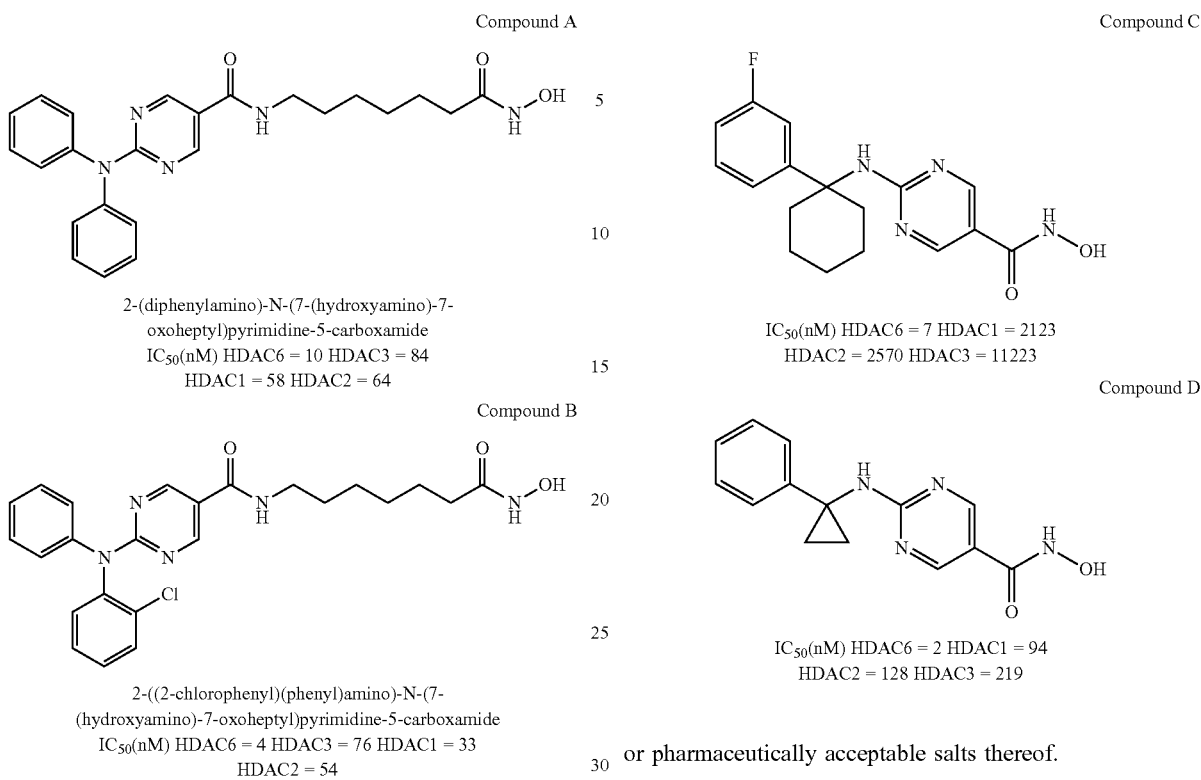

2-(diphenylamino)-N-(7-(hydroxyamino)-7-oxoheptyl)pyrimidine-5-carboxamide
IC$_{50}$(nM) HDAC6 = 10 HDAC3 = 84
HDAC1 = 58 HDAC2 = 64

Compound B 2-((2-chlorophenyl)(phenyl)amino)-N-(7-(hydroxyamino)-7-oxoheptyl)pyrimidine-5-carboxamide
IC$_{50}$(nM) HDAC6 = 4 HDAC3 = 76 HDAC1 = 33
HDAC2 = 54

Compound C

IC$_{50}$(nM) HDAC6 = 7 HDAC1 = 2123
HDAC2 = 2570 HDAC3 = 11223

Compound D

IC$_{50}$(nM) HDAC6 = 2 HDAC1 = 94
HDAC2 = 128 HDAC3 = 219 or pharmaceutically acceptable salts thereof.

The preparation and properties of selective HDAC6 inhibitors according to Formula I are provided in International Patent Application No. PCT/US2011/021982, the entire contents of which are incorporated herein by reference.

In other embodiments, the HDAC6-specific inhibitor is a compound of Formula II:

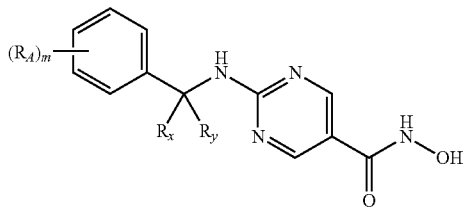

(II)

or a pharmaceutically acceptable salt thereof,
wherein, $R_x$ and $R_y$, together with the carbon to which each is attached, form a cyclopropyl, cyclobutyl, cyclopentyl, cyclohexyl, cycloheptyl, or cyclooctyl;

each $R_A$ is independently $C_{1-6}$-alkyl, $C_{1-6}$-alkoxy, halo, OH, —NO$_2$, —CN, or —NH$_2$; and m is 0, 1, or 2.

Representative compounds of Formula II include, but are not limited to:

or pharmaceutically acceptable salts thereof.

The preparation and properties of selective HDAC6 inhibitors according to Formula II are provided in International Patent Application No. PCT/US2011/060791, the entire contents of which are incorporated herein by reference.

In some embodiments, the HDAC1/2-specific inhibitor is a compound of Formula III:

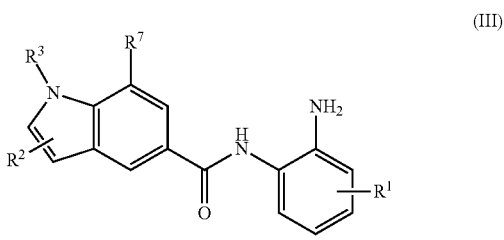

(III)

or a pharmaceutically acceptable salt thereof,
wherein, $R^1$ is aryl or heteroaryl;

$R^2$ and $R^3$ are each independently selected from $C_{3-6}$-cycloalkyl, $C_{1-6}$-alkyl-OR$^6$, $C_{1-6}$-alkyl-$C_{3-6}$-cycloalkyl, $C_{1-6}$-alkyl-heterocycloalkyl, and $C_{2-6}$-alkenyl;

$R^6$ is H or $C_{1-6}$-alkyl; and $R^7$ is H or $C_{3-6}$-cycloalkyl.

Compounds of Formula III are represented by, but not limited to, Compound E, or pharmaceutically acceptable salts thereof.

COMPOUND E

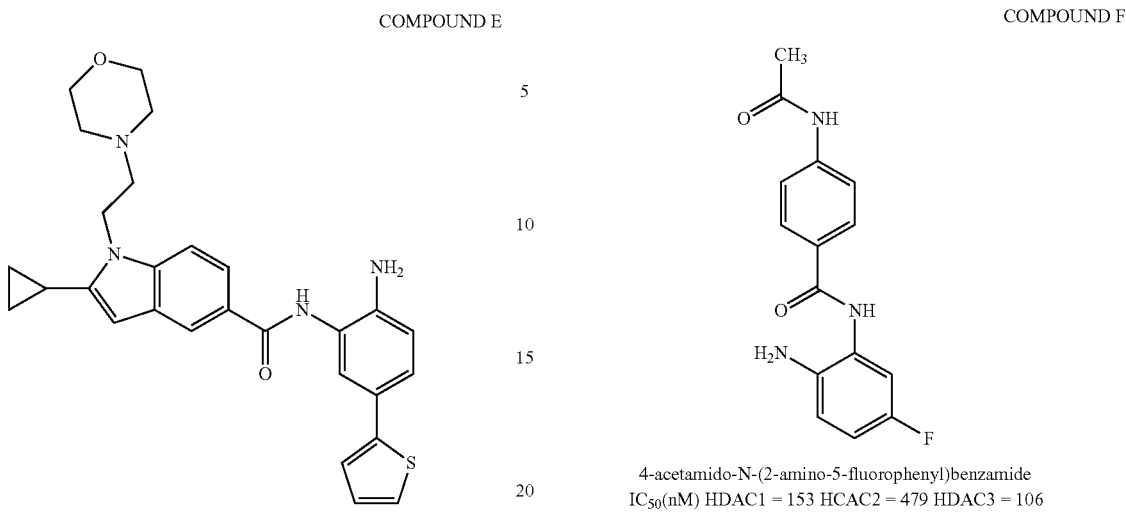

N-(2-amino-5-(thiophen-2-yl)phenyl)-2-cyclopropyl-1-(2-morpholinoethyl)-1H-indole-5-carboxamide
IC$_{50}$(nM): HDAC1 = 6 HDAC2 = 36 HDAC3 = 445
C$_{max}$ = 2037 AUC = 9496
hERG IC$_{50}$ (μM) >30

In another embodiments, the HDAC1/2-specific inhibitor is N-(2-amino-5-(thiophen-2-yl)phenyl)-2-(piperazin-1-yl)quinoline-6-carboxamide (or a pharmaceutically acceptable salt thereof:

Compound J

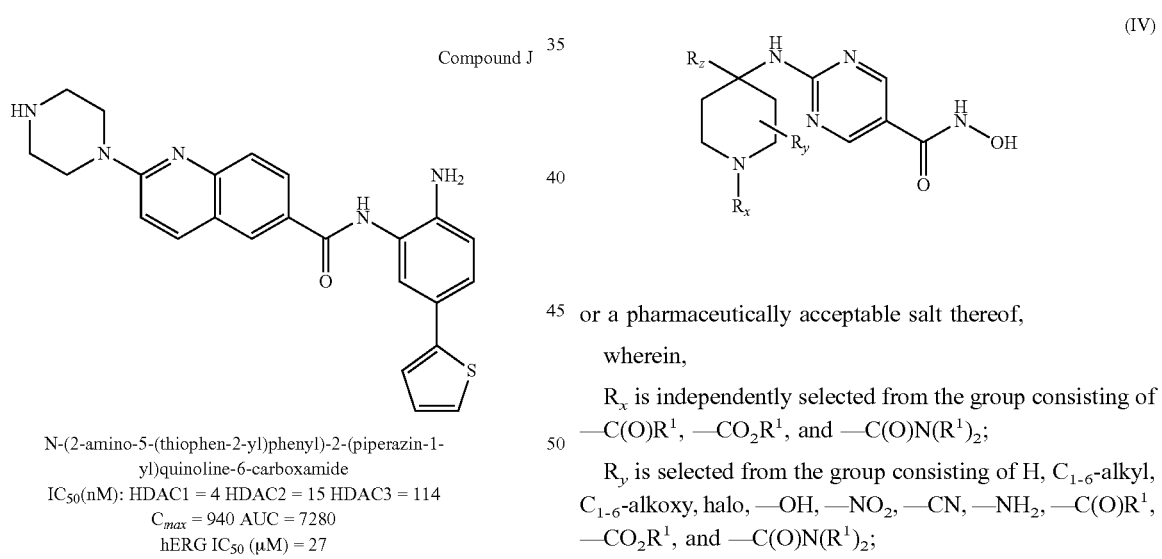

N-(2-amino-5-(thiophen-2-yl)phenyl)-2-(piperazin-1-yl)quinoline-6-carboxamide
IC$_{50}$(nM): HDAC1 = 4 HDAC2 = 15 HDAC3 = 114
C$_{max}$ = 940 AUC = 7280
hERG IC$_{50}$ (μM) = 27

The preparation and properties of selective HDAC1/2 inhibitors according to Formula III, as well as Compound J, are provided in U.S. patent application Ser. No. 14/069,741, the entire contents of which are incorporated herein by reference.

In another embodiment, the HDAC inhibitor is 4-acetamido-N-(2-amino-5-fluorophenyl)benzamide (Compound F), or a pharmaceutically acceptable salt thereof.

COMPOUND F 4-acetamido-N-(2-amino-5-fluorophenyl)benzamide
IC$_{50}$(nM) HDAC1 = 153 HCAC2 = 479 HDAC3 = 106

The preparation and properties of the HDAC inhibitor Compound F are provided in International Patent Application No. PCT/US2013/052572, the entire contents of which are incorporated herein by reference.

In some embodiments, the HDAC1/2/6-specific inhibitor is a compound of Formula IV:

(IV)

or a pharmaceutically acceptable salt thereof, wherein,

R$_x$ is independently selected from the group consisting of —C(O)R$^1$, —CO$_2$R$^1$, and —C(O)N(R$^1$)$_2$;

R$_y$ is selected from the group consisting of H, C$_{1-6}$-alkyl, C$_{1-6}$-alkoxy, halo, —OH, —NO$_2$, —CN, —NH$_2$, —C(O)R$^1$, —CO$_2$R$^1$, and —C(O)N(R$^1$)$_2$;

each R$^1$ is, independently for each occurrence, selected from the group consisting of H, C$_{1-6}$-alkyl, C$_{3-8}$-cycloalkyl, C$_{3-7}$-heterocycloalkyl, aryl, heteroaryl, C$_{1-6}$-alkyl-cycloalkyl, C$_{1-6}$-alkyl-heterocycloalkyl, C$_{1-6}$-alkyl-aryl, and C$_{1-6}$-alkyl-heteroaryl; and R$_z$ is selected from the group consisting of C$_{1-6}$-alkyl, C$_{3-8}$-cycloalkyl, C$_{3-7}$-heterocycloalkyl, aryl, and heteroaryl.

Compounds of Formula IV are represented by, but not limited to, Compound G, or a pharmaceutically acceptable salt thereof.

Compound G

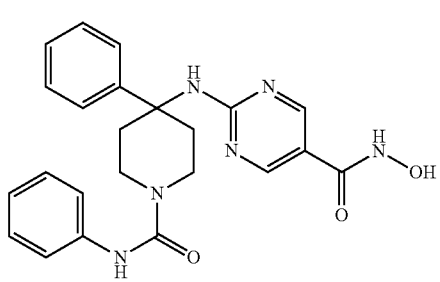 [SMILES: O=C(NO)c1cnc(NC2(c3ccccc3)CCN(C(=O)Nc3ccccc3)CC2)nc1]

N-hydroxy-2-((4-phenyl-1-(phenylcarbamoyl)piperidin-
4-yl)amino)pyrimidine-5-carboxamide
IC$_{50}$(nM) HDAC1 = 38 HDAC2 = 34 HDAC3 = 1010
HDAC6 = 1.9

The preparation and properties of HDAC1/2/6 specific inhibitors according to Formula IV are provided in International Application No. PCT/US2014/059863, the entire contents of which are incorporated herein by reference.

In some embodiments, the compounds described herein are unsolvated. In other embodiments, one or more of the compounds are in solvated form. As known in the art, the solvate can be any of pharmaceutically acceptable solvent, such as water, ethanol, and the like.

Combinations/Pharmaceutical Combinations

Provided herein are combinations for the treatment of leukemia in a subject in need thereof. Provided in some embodiments are combinations comprising a histone deacetylase (HDAC) inhibitor and azacitidine for the treatment of leukemia (e.g., AML) in a subject in need thereof.

In some embodiments of the combinations, the HDAC inhibitor is an HDAC6-specific inhibitor. In specific embodiments, the HDAC6-specific inhibitor is a compound of Formula I:

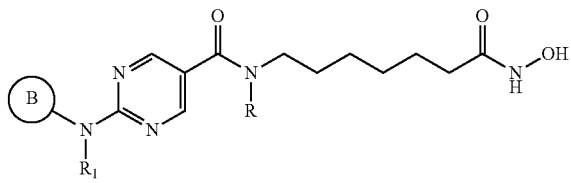

(I)

or a pharmaceutically acceptable salt thereof.

In preferred embodiments, the compound of Formula I is:

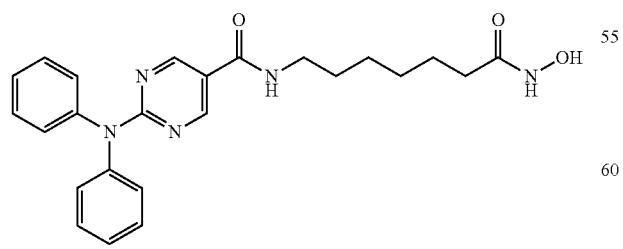

or a pharmaceutically acceptable salt thereof.

In other preferred embodiments, the compound of Formula I is:

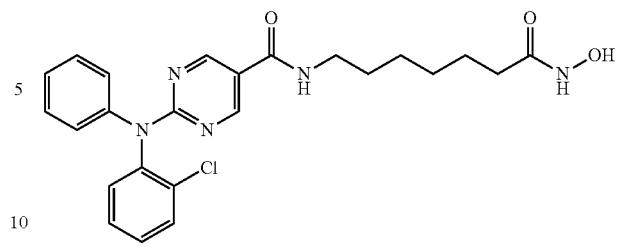

or a pharmaceutically acceptable salt thereof.

In other specific embodiments, the HDAC6-specific inhibitor is a compound of Formula II:

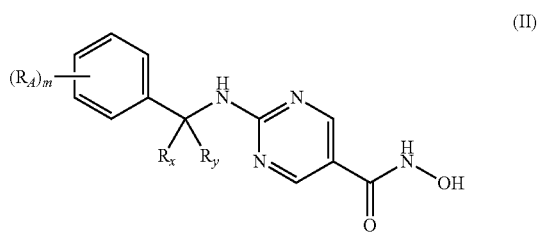

(II)

or a pharmaceutically acceptable salt thereof.

In preferred embodiments, the compound of Formula II is:

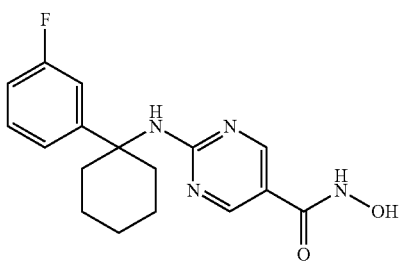 [SMILES: O=C(NO)c1cnc(NC2(c3cccc(F)c3)CCCCC2)nc1]

or a pharmaceutically acceptable salt thereof.

In other preferred embodiments, the compound of Formula II is:

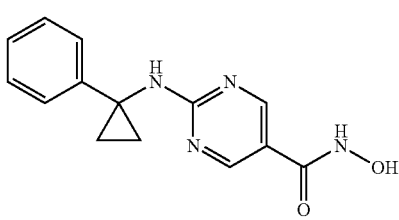 [SMILES: O=C(NO)c1cnc(NC2(c3ccccc3)CC2)nc1]

or a pharmaceutically acceptable salt thereof.

In some embodiments of the combinations, the HDAC inhibitor is an HDAC1/2-specific inhibitor. In specific embodiments, the HDAC1/2-specific inhibitor is a compound of Formula III:

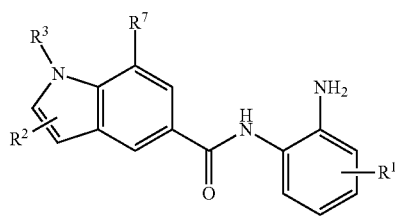

or a pharmaceutically acceptable salt thereof.

In preferred embodiments, the compound of Formula III is:

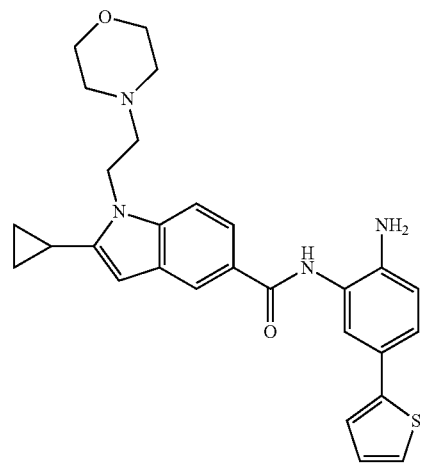 [SMILES: Nc1ccc(-c2cccs2)cc1NC(=O)c1ccc2c(c1)cc(C1CC1)n2CCN1CCOCC1]

or a pharmaceutically acceptable salt thereof.

In another embodiment, the HDAC1/2-specific inhibitor is the compound J:

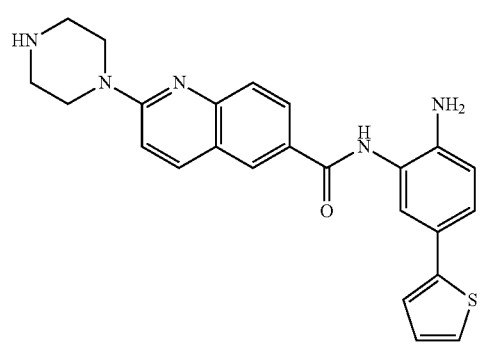 [SMILES: Nc1ccc(-c2cccs2)cc1NC(=O)c1ccc2nc(N3CCNCC3)ccc2c1]

or a pharmaceutically acceptable salt thereof.

In another embodiment, the HDAC inhibitor is the compound F:

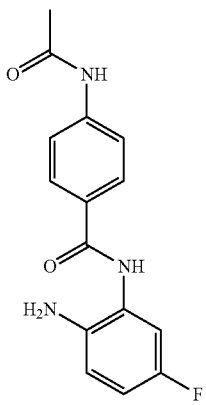 [SMILES: CC(=O)Nc1ccc(C(=O)Nc2cc(F)ccc2N)cc1]

or a pharmaceutically acceptable salt thereof.

In some embodiments of the combinations, the HDAC inhibitor is an HDAC1/2/6-specific inhibitor. In other specific embodiments, the HDAC1/2/6-specific inhibitor is a compound of Formula IV:

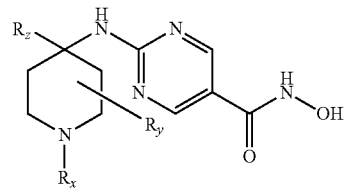

or a pharmaceutically acceptable salt thereof.

In preferred embodiments, the compound of Formula IV is:

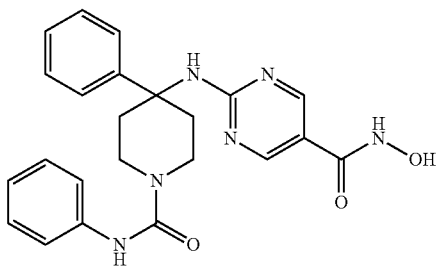 [SMILES: O=C(NO)c1cnc(NC2(c3ccccc3)CCN(C(=O)Nc3ccccc3)CC2)nc1]

or a pharmaceutically acceptable salt thereof.

In some embodiments of the combinations, azacitidine may be the free base or a pharmaceutically acceptable salt thereof. See Cihak, "Biological effects of 5-azacytidine in eukaryotes", *Oncology*, vol. 30(5), pp. 405-422 (1974). 5-azacytidine (also known as azacitidine and 4-amino-1-β-D-ribofuranosyl-S-triazin-2(1H)-one; Nation Service Center designation NSC-102816; CAS Registry Number 320-67-2) is sold under the trade name Vidaza for the treatment of myelodysplastic syndrome (MDS).

Although the compounds of Formulas I, II, III, IV, Compound F, and Compound J are depicted in their neutral forms, in some embodiments, these compounds are used in a pharmaceutically acceptable salt form. As used herein, "pharmaceutically acceptable salts" refers to derivatives of the disclosed compounds wherein the parent compound is modified by converting an existing acid or base moiety to its salt form. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Administration/Dose

In some embodiments, the HDAC inhibitor (a compound of Formulas I, II, III, IV, Compound F or Compound J) is administered simultaneously with azacitidine. Simultaneous administration typically means that both compounds enter the patient at precisely the same time. However, simultaneous administration also includes the possibility that the HDAC inhibitor and azacitidine enter the patient at different times, but the difference in time is sufficiently miniscule that the first administered compound is not provided the time to take effect on the patient before entry of the second administered compound. Such delayed times typically correspond to less than 1 minute, and more typically, less than 30 seconds. In one example, wherein the compounds are in solution, simultaneous administration can be achieved by administering a solution containing the combination of compounds. In another example, simultaneous administration of separate solutions, one of which contains the HDAC inhibitor and the other of which contains azacitidine, can be employed. In one example wherein the compounds are in solid form, simultaneous administration can be achieved by administering a composition containing the combination of compounds. Alternatively, simultaneous administration can be achieved by administering two separate compositions, one comprising the HDAC inhibitor and the other comprising azacitidine.

In other embodiments, the HDAC inhibitor and azacitidine are not administered simultaneously. In some embodiments, the HDAC inhibitor is administered before azacitidine. In other embodiments, azacitidine is administered before the HDAC inhibitor. In other embodiments, the first administered compound is provided time to take effect on the patient before the second administered compound is administered. Generally, the difference in time does not extend beyond the time for the first administered compound to complete its effect in the patient, or beyond the time the first administered compound is completely or substantially eliminated or deactivated in the patient.

In some embodiments, one or both of the HDAC inhibitor and azacitidine are administered in a therapeutically effective amount or dosage. A "therapeutically effective amount" is an amount of HDAC inhibitor (a compound of Formulas I, II, III, IV, Compound F or Compound J) or azacitidine that, when administered to a patient by itself, effectively treats leukemia. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the compound that corresponds to a therapeutically effective amount is strongly dependent on the type of cancer, stage of the cancer, the age of the patient being treated, and other facts. In general, therapeutically effective amounts of these compounds are well-known in the art, such as provided in the supporting references cited above.

In other embodiments, one or both of the HDAC inhibitor and azacitidine are administered in a sub-therapeutically effective amount or dosage. A sub-therapeutically effective amount is an amount of HDAC inhibitor (a compound of Formulas I, II, III, IV, Compound F or Compound J) or azacitidine that, when administered to a patient by itself, does not completely inhibit over time the biological activity of the intended target.

Whether administered in therapeutic or sub-therapeutic amounts, the combination of the HDAC inhibitor and azacitidine should be effective in treating a leukemia, e.g., AML. For example, a sub-therapeutic amount of a compound of azacitidine can be an effective amount if, when combined with a compound of Formulas I, II, III, IV, Compound F, or Compound J (HDAC inhibitor), the combination is effective in the treatment of leukemia. For example, a sub-therapeutic amount of a compound of azacitidine can be an effective amount if, when combined with a compound of Formulas I, II, III, Compound F, or Compound J (HDAC inhibitor), the combination is effective in the treatment of leukemia, wherein the combination is administered at dosages that would not be effective when one or both of the compounds are administered alone, but which amounts are effective in combination.

In some embodiments, the combination of compounds exhibits a synergistic effect (i.e., greater than additive effect) in the treatment of leukemia. In further embodiments, the combination of compounds exhibits a synergistic effect (i.e., greater than additive effect) in the treatment of acute myelogenous leukemia. The term "synergistic effect" refers to the action of two agents, such as, for example, an HDAC inhibitor and azacitidine, producing an effect, for example, slowing the symptomatic progression of cancer or symptoms thereof, which is greater than the simple addition of the effects of each drug administered alone. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

In preferred embodiments provided herein are combinations and methods that include an HDAC inhibitor of Formula I and azacitidine. Thus, in one embodiment, the combinations and methods include Compound A and azacitidine. In another embodiment, the combinations and methods include Compound B and azacitidine. In other preferred embodiments provided herein, the combinations and methods include an HDAC inhibitor of Formula II and azacitidine. Thus, in one embodiment, the combinations and methods include Compound C and azacitidine. In another embodiment, the combinations and methods include Compound D and azacitidine. In other preferred embodiments provided herein, the combinations and methods include an HDAC inhibitor of Formula III and azacitidine. Thus, in one embodiment, the combinations and methods include Compound E and azacitidine. In another preferred embodiment provided herein, the combinations and methods include the HDAC inhibitor Compound J and azacitidine. In other preferred embodiments provided herein, the combinations and methods include the HDAC inhibitor Compound F and azacitidine. In other preferred embodiments provided herein, the combinations and methods include an HDAC inhibitor of Formula IV and azacitidine. Thus, in one embodiment, the combinations and methods include Compound G and azacitidine.

In different embodiments, depending on the combination and the effective amounts used, the combination of compounds can inhibit leukemia growth, achieve leukemia stasis, or even achieve substantial or complete leukemia regression.

While the amounts of an HDAC inhibitor and azacitidine should result in the effective treatment of leukemia, the amounts, when combined, are preferably not excessively toxic to the patient (i.e., the amounts are preferably within toxicity limits as established by medical guidelines). In some embodiments, either to prevent excessive toxicity and/or provide a more efficacious treatment of leukemia, a limitation on the total administered dosage is provided. Typically, the amounts considered herein are per day; however, half-day and two-day or three-day cycles also are considered herein.

Different dosage regimens may be used to treat leukemia. In some embodiments, a daily dosage, such as any of the exemplary dosages described above, is administered once, twice, three times, or four times a day for three, four, five, six, seven, eight, nine, or ten days. Depending on the stage and severity of the cancer, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day. In some embodiments, each dosage contains both an HDAC inhibitor and azacitidine to be delivered as a single dosage, while in other embodiments each dosage contains an HDAC inhibitor or azacitidine to be delivered as separate dosages.

Compounds of Formulas I, II, III, IV, Compound F, or Compound J, or their pharmaceutically acceptable salts or solvate forms, in pure form or in an appropriate pharmaceutical composition, can be administered via any of the accepted modes of administration or agents known in the art. The compounds can be administered, for example, orally, nasally, parenterally (intravenous, intramuscular, or subcutaneous), topically, transdermally, intravaginally, intravesically, intracisternally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, preferably in unit dosage forms suitable for simple administration of precise dosages. A particular route of administration is oral, particularly one in which a convenient daily dosage regimen can be adjusted according to the degree of severity of the disease to be treated.

As discussed above, the HDAC inhibitor and azacitidine pharmaceutical combination can be administered in a single unit dose or separate dosage forms. Accordingly, the phrase "pharmaceutical combination" includes a combination of two drugs in either a single dosage form or separate dosage forms, i.e., the pharmaceutically acceptable carriers and excipients described throughout the application can be combined with an HDAC inhibitor and azacitidine in a single unit dose, as well as individually combined with an HDAC inhibitor and azacitidine when these compounds are administered separately.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

Solid dosage forms can be prepared with coatings and shells, such as enteric coatings and others well-known in the art. They can contain pacifying agents and can be of such composition that they release the active compound or compounds in a certain part of the intestinal tract in a delayed manner. Examples of embedded compositions that can be used are polymeric substances and waxes. The active compounds also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the HDAC inhibitors or azacitidine described herein, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Generally, depending on the intended mode of administration, the pharmaceutically acceptable compositions will contain about 1% to about 99% by weight of the compounds described herein, or a pharmaceutically acceptable salt thereof, and 99% to 1% by weight of a pharmaceutically acceptable excipient. In one example, the composition will be between about 5% and about 75% by weight of a compound described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

Methods

Provided herein are methods for treating leukemia in a subject in need thereof comprising administering to the subject a pharmaceutical combination provided herein. Further provided herein are methods for treating leukemia in a subject in need thereof comprising administering to the subject an HDAC inhibitor. Thus, provided herein are methods for treating leukemia in a subject in need thereof comprising administering to the subject a therapeutically effective amount of a combination comprising an HDAC inhibitor and azacitidine, or alternatively administering to the subject a therapeutically effective amount of an HDAC inhibitor. In a preferred embodiment of the methods provided herein, the leukemia is acute myelogenous leukemia. In another preferred embodiment of the methods provided herein, the HDAC inhibitor is an HDAC6-specific, HDAC1/2-specific, or HDAC1/2/6-specific inhibitor. In another preferred embodiment of the methods provided herein, the HDAC inhibitor is a compound of Formula I, Formula II, Formula III or Formula IV. In another preferred embodiment of the methods provided herein, the HDAC inhibitor is Compound A, Compound B, Compound C, Compound D, Compound E, Compound F, Compound G, Compound H or Compound J.

Also provided herein are methods for treating a CD11b-expressing cancer in a subject in need thereof comprising administering to the subject a pharmaceutical combination provided herein. Further provided herein are methods for treating a CD11b-expressing cancer in a subject in need thereof comprising administering to the subject an HDAC inhibitor. Thus, provided herein are methods for treating a CD11b-expressing cancer in a subject in need thereof comprising administering to the subject a therapeutically effective amount of a combination comprising an HDAC inhibitor and azacitidine, or alternatively administering to the subject a therapeutically effective amount of an HDAC inhibitor. In another preferred embodiment of the methods provided herein, the HDAC inhibitor is an HDAC6-specific, HDAC1/2-specific, or HDAC1/2/6-specific inhibitor. In another preferred embodiment of the methods provided herein, the HDAC inhibitor is a compound of Formula I, Formula II, Formula III or Formula IV. In another preferred embodiment of the methods provided herein, the HDAC inhibitor is Compound A, Compound B, Compound C, Compound D, Compound E, Compound F, Compound G, Compound H or Compound J.

The subject considered herein is typically a human. However, the subject can be any mammal for which treatment is desired. Thus, the methods described herein can be applied to both human and veterinary applications.

The terms "treating" or "treatment" indicates that the method has, at the least, mitigated abnormal cellular proliferation. For example, the method can reduce the rate of leukemia growth in a patient, or prevent the continued growth or spread of the leukemia, or even reduce the overall reach of leukemia.

In one embodiment, provided herein is a method for treating leukemia in a subject in need thereof comprising administering to the subject a therapeutically effective amount of an HDAC6-specific inhibitor, or a pharmaceutically acceptable salt thereof, and azacitidine, or a pharmaceutically acceptable salt thereof.

In another embodiment, provided herein is a method for treating leukemia in a subject in need thereof comprising administering to the subject a therapeutically effective amount of an HDAC1/2-specific inhibitor, or a pharmaceutically acceptable salt thereof, and azacitidine, or a pharmaceutically acceptable salt thereof.

In yet another embodiment, provided herein is a method for treating leukemia in a subject in need thereof comprising administering to the subject a therapeutically effective amount of an HDAC1/2/6-specific inhibitor, or a pharmaceutically acceptable salt thereof, and azacitidine, or a pharmaceutically acceptable salt thereof.

In another embodiment, provided herein is a method for treating leukemia in a subject in need thereof comprising administering to the subject a therapeutically effective amount of a compound of Formula I, or a pharmaceutically acceptable salt thereof, and azacitidine, or a pharmaceutically acceptable salt thereof.

In another embodiment, provided herein is a method for treating leukemia in a subject in need thereof comprising administering to the subject a therapeutically effective amount of a compound of Formula II, or a pharmaceutically acceptable salt thereof, and azacitidine, or a pharmaceutically acceptable salt thereof.

In another embodiment, provided herein is a method for treating leukemia in a subject in need thereof comprising administering to the subject a therapeutically effective amount of a compound of Formula III, or a pharmaceutically acceptable salt thereof, and azacitidine, or a pharmaceutically acceptable salt thereof.

In another embodiment, provided herein is a method for treating leukemia in a subject in need thereof comprising administering to the subject a therapeutically effective amount of a compound of Formula IV, or a pharmaceutically acceptable salt thereof, and azacitidine, or a pharmaceutically acceptable salt thereof.

In another embodiment, provided herein is a method for treating leukemia in a subject in need thereof comprising administering to the subject a therapeutically effective amount of Compound A, or a pharmaceutically acceptable salt thereof, and azacitidine, or a pharmaceutically acceptable salt thereof.

In another embodiment is a method for treating leukemia in a subject in need thereof comprising administering to the subject a therapeutically effective amount of Compound B, or a pharmaceutically acceptable salt thereof, and azacitidine, or a pharmaceutically acceptable salt thereof.

In another embodiment is a method for treating leukemia in a subject in need thereof comprising administering to the subject a therapeutically effective amount of Compound C, or a pharmaceutically acceptable salt thereof, and azacitdine, or a pharmaceutically acceptable salt thereof.

In another embodiment is a method for treating leukemia in a subject in need thereof comprising administering to the subject a therapeutically effective amount of Compound D, or a pharmaceutically acceptable salt thereof, and azacitidine, or a pharmaceutically acceptable salt thereof.

In another embodiment is a method for treating leukemia in a subject in need thereof comprising administering to the subject a therapeutically effective amount of Compound E, or a pharmaceutically acceptable salt thereof, and azacitidine, or a pharmaceutically acceptable salt thereof.

In another embodiment is a method for treating leukemia in a subject in need thereof comprising administering to the subject a therapeutically effective amount of Compound F, or a pharmaceutically acceptable salt thereof, and azacitidine, or a pharmaceutically acceptable salt thereof.

In another embodiment is a method for treating leukemia in a subject in need thereof comprising administering to the subject a therapeutically effective amount of Compound G, or a pharmaceutically acceptable salt thereof, and azacitidine, or a pharmaceutically acceptable salt thereof.

In another embodiment is a method for treating leukemia in a subject in need thereof comprising administering to the subject a therapeutically effective amount of Compound H, or a pharmaceutically acceptable salt thereof, and azacitidine, or a pharmaceutically acceptable salt thereof.

In another embodiment is a method for treating leukemia in a subject in need thereof comprising administering to the subject a therapeutically effective amount of Compound J, or a pharmaceutically acceptable salt thereof, and azacitidine, or a pharmaceutically acceptable salt thereof.

In one embodiment, provided herein is a method for treating acute myelogenous leukemia in a subject in need thereof comprising administering to the subject a therapeutically effective amount of an HDAC6-specific inhibitor, or a pharmaceutically acceptable salt thereof, and azacitidine, or a pharmaceutically acceptable salt thereof.

In another embodiment, provided herein is a method for treating acute myelogenous leukemia in a subject in need thereof comprising administering to the subject a therapeutically effective amount of an HDAC1/2-specific inhibitor, or a pharmaceutically acceptable salt thereof, and azacitidine, or a pharmaceutically acceptable salt thereof.

In yet another embodiment, provided herein is a method for treating acute myelogenous leukemia in a subject in need thereof comprising administering to the subject a therapeutically effective amount of an HDAC1/2/6-specific inhibitor, or a pharmaceutically acceptable salt thereof, and azacitidine, or a pharmaceutically acceptable salt thereof.

In another embodiment, provided herein is a method for treating acute myelogenous leukemia in a subject in need thereof comprising administering to the subject a therapeutically effective amount of a compound of Formula I, or a pharmaceutically acceptable salt thereof, and azacitidine, or a pharmaceutically acceptable salt thereof.

In another embodiment, provided herein is a method for treating acute myelogenous leukemia in a subject in need thereof comprising administering to the subject a therapeutically effective amount of a compound of Formula II, or a pharmaceutically acceptable salt thereof, and azacitidine, or a pharmaceutically acceptable salt thereof.

In another embodiment, provided herein is a method for treating acute myelogenous leukemia in a subject in need thereof comprising administering to the subject a therapeutically effective amount of a compound of Formula III, or a pharmaceutically acceptable salt thereof, and azacitidine, or a pharmaceutically acceptable salt thereof.

In another embodiment, provided herein is a method for treating acute myelogenous leukemia in a subject in need thereof comprising administering to the subject a therapeutically effective amount of a compound of Formula IV, or a pharmaceutically acceptable salt thereof, and azacitidine, or a pharmaceutically acceptable salt thereof.

In another embodiment is a method for treating acute myelogenous leukemia in a subject in need thereof comprising administering to the subject a therapeutically effective amount of Compound A, or a pharmaceutically acceptable salt thereof, and azacitidine, or a pharmaceutically acceptable salt thereof.

In another embodiment is a method for treating acute myelogenous leukemia in a subject in need thereof comprising administering to the subject a therapeutically effective amount of Compound B, or a pharmaceutically acceptable salt thereof, and azacitidine, or a pharmaceutically acceptable salt thereof.

In another embodiment is a method for treating acute myelogenous leukemia in a subject in need thereof comprising administering to the subject a therapeutically effective amount of Compound C, or a pharmaceutically acceptable salt thereof, and azacitdine, or a pharmaceutically acceptable salt thereof.

In another embodiment is a method for treating acute myelogenous leukemia in a subject in need thereof comprising administering to the subject a therapeutically effective amount of Compound D, or a pharmaceutically acceptable salt thereof, and azacitidine, or a pharmaceutically acceptable salt thereof.

In another embodiment is a method for treating acute myelogenous leukemia in a subject in need thereof comprising administering to the subject a therapeutically effective amount of Compound E, or a pharmaceutically acceptable salt thereof, and azacitidine, or a pharmaceutically acceptable salt thereof.

In another embodiment is a method for treating acute myelogenous leukemia in a subject in need thereof comprising administering to the subject a therapeutically effective amount of Compound F, or a pharmaceutically acceptable salt thereof, and azacitidine, or a pharmaceutically acceptable salt thereof.

In another embodiment is a method for treating acute myelogenous leukemia in a subject in need thereof comprising administering to the subject a therapeutically effective amount of Compound G, or a pharmaceutically acceptable salt thereof, and azacitidine, or a pharmaceutically acceptable salt thereof.

In another embodiment is a method for treating acute myelogenous leukemia in a subject in need thereof comprising administering to the subject a therapeutically effective amount of Compound H, or a pharmaceutically acceptable salt thereof, and azacitidine, or a pharmaceutically acceptable salt thereof.

In another embodiment is a method for treating acute myelogenous leukemia in a subject in need thereof comprising administering to the subject a therapeutically effective amount of Compound J, or a pharmaceutically acceptable salt thereof, and azacitidine, or a pharmaceutically acceptable salt thereof.

In one embodiment, provided herein is a method for treating leukemia in a subject in need thereof comprising administering to the subject a therapeutically effective amount of an HDAC6-specific inhibitor, or a pharmaceutically acceptable salt thereof.

In another embodiment, provided herein is a method for treating leukemia in a subject in need thereof comprising administering to the subject a therapeutically effective amount of an HDAC1/2-specific inhibitor, or a pharmaceutically acceptable salt thereof.

In yet another embodiment, provided herein is a method for treating leukemia in a subject in need thereof comprising administering to the subject a therapeutically effective amount of an HDAC1/2/6-specific inhibitor, or a pharmaceutically acceptable salt thereof.

In another embodiment, provided herein is a method for treating leukemia in a subject in need thereof comprising administering to the subject a therapeutically effective amount of a compound of Formula I, or a pharmaceutically acceptable salt thereof.

In another embodiment, provided herein is a method for treating leukemia in a subject in need thereof comprising administering to the subject a therapeutically effective amount of a compound of Formula II, or a pharmaceutically acceptable salt thereof.

In another embodiment, provided herein is a method for treating leukemia in a subject in need thereof comprising administering to the subject a therapeutically effective amount of a compound of Formula III, or a pharmaceutically acceptable salt thereof.

In another embodiment, provided herein is a method for treating leukemia in a subject in need thereof comprising administering to the subject a therapeutically effective amount of a compound of Formula IV, or a pharmaceutically acceptable salt thereof.

In another embodiment, provided herein is a method for treating leukemia in a subject in need thereof comprising administering to the subject a therapeutically effective amount of Compound A, or a pharmaceutically acceptable salt thereof.

In another embodiment is a method for treating leukemia in a subject in need thereof comprising administering to the subject a therapeutically effective amount of Compound B, or a pharmaceutically acceptable salt thereof.

In another embodiment is a method for treating leukemia in a subject in need thereof comprising administering to the subject a therapeutically effective amount of Compound C, or a pharmaceutically acceptable salt thereof.

In another embodiment is a method for treating leukemia in a subject in need thereof comprising administering to the subject a therapeutically effective amount of Compound D, or a pharmaceutically acceptable salt thereof.

In another embodiment is a method for treating leukemia in a subject in need thereof comprising administering to the subject a therapeutically effective amount of Compound E or a pharmaceutically acceptable salt thereof.

In another embodiment is a method for treating leukemia in a subject in need thereof comprising administering to the subject a therapeutically effective amount of Compound F or a pharmaceutically acceptable salt thereof.

In another embodiment is a method for treating leukemia in a subject in need thereof comprising administering to the subject a therapeutically effective amount of Compound G or a pharmaceutically acceptable salt thereof.

In another embodiment is a method for treating leukemia in a subject in need thereof comprising administering to the subject a therapeutically effective amount of Compound H, or a pharmaceutically acceptable salt thereof.

In another embodiment is a method for treating leukemia in a subject in need thereof comprising administering to the subject a therapeutically effective amount of Compound J, or a pharmaceutically acceptable salt thereof.

In one embodiment, provided herein is a method for treating acute myelogenous leukemia in a subject in need thereof comprising administering to the subject a therapeutically effective amount of an HDAC6-specific inhibitor, or a pharmaceutically acceptable salt thereof.

In another embodiment, provided herein is a method for treating acute myelogenous leukemia in a subject in need thereof comprising administering to the subject a therapeutically effective amount of an HDAC1/2-specific inhibitor, or a pharmaceutically acceptable salt thereof.

In yet another embodiment, provided herein is a method for treating acute myelogenous leukemia in a subject in need thereof comprising administering to the subject a therapeutically effective amount of an HDAC1/2/6-specific inhibitor, or a pharmaceutically acceptable salt thereof.

In another embodiment, provided herein is a method for treating acute myelogenous leukemia in a subject in need thereof comprising administering to the subject a therapeutically effective amount of a compound of Formula I, or a pharmaceutically acceptable salt thereof.

In another embodiment, provided herein is a method for treating acute myelogenous leukemia in a subject in need thereof comprising administering to the subject a therapeutically effective amount of a compound of Formula II, or a pharmaceutically acceptable salt thereof.

In another embodiment, provided herein is a method for treating acute myelogenous leukemia in a subject in need thereof comprising administering to the subject a therapeutically effective amount of a compound of Formula III, or a pharmaceutically acceptable salt thereof.

In another embodiment, provided herein is a method for treating acute myelogenous leukemia in a subject in need thereof comprising administering to the subject a therapeutically effective amount of a compound of Formula IV, or a pharmaceutically acceptable salt thereof.

In another embodiment is a method for treating acute myelogenous leukemia in a subject in need thereof comprising administering to the subject a therapeutically effective amount of Compound A, or a pharmaceutically acceptable salt thereof.

In another embodiment is a method for treating acute myelogenous leukemia in a subject in need thereof comprising administering to the subject a therapeutically effective amount of Compound B, or a pharmaceutically acceptable salt thereof.

In another embodiment is a method for treating acute myelogenous leukemia in a subject in need thereof comprising administering to the subject a therapeutically effective amount of Compound C, or a pharmaceutically acceptable salt thereof.

In another embodiment is a method for treating acute myelogenous leukemia in a subject in need thereof comprising administering to the subject a therapeutically effective amount of Compound D, or a pharmaceutically acceptable salt thereof.

In another embodiment is a method for treating acute myelogenous leukemia in a subject in need thereof comprising administering to the subject a therapeutically effective amount of Compound E, or a pharmaceutically acceptable salt thereof.

In another embodiment is a method for treating acute myelogenous leukemia in a subject in need thereof comprising administering to the subject a therapeutically effective amount of Compound F, or a pharmaceutically acceptable salt thereof.

In another embodiment is a method for treating acute myelogenous leukemia in a subject in need thereof comprising administering to the subject a therapeutically effective amount of Compound G, or a pharmaceutically acceptable salt thereof.

In another embodiment is a method for treating acute myelogenous leukemia in a subject in need thereof comprising administering to the subject a therapeutically effective amount of Compound H, or a pharmaceutically acceptable salt thereof.

In another embodiment is a method for treating acute myelogenous leukemia in a subject in need thereof comprising administering to the subject a therapeutically effective amount of Compound J, or a pharmaceutically acceptable salt thereof.

Also provided herein are methods for inhibiting migration and/or invasion of leukemia cells. In particular, provided herein are methods for inhibiting migration and/or invasion of leukemia cells in a subject in need thereof. Specifically, provided herein are methods for inhibiting migration and invasion of leukemia cells, or both, in a subject in need thereof comprising administering to the subject a therapeutically effective amount of an HDAC inhibitor of Formulas I, II, III, IV, Compound A, Compound B, Compound C, Compound D, Compound E, Compound F, Compound G, Compound H, or Compound J. In an embodiment, the HDAC inhibitor is Compound J, or a pharmaceutically acceptable salt thereof.

Provided herein are methods for decreasing cell viability of cancer cells by administering a combination comprising an HDAC inhibitor and azacitidine. In an embodiment, the HDAC inhibitor is Compound J, or a pharmaceutically acceptable salt thereof.

Also provided herein are methods for inducing differentiation of cancer cells by administering a combination comprising an HDAC inhibitor and azacitidine. In an embodiment, the HDAC inhibitor is Compound 0.1, or a pharmaceutically acceptable salt thereof.

Also provided herein are methods for inducing apoptosis of cancer cells by administering a combination comprising an HDAC inhibitor and azacitidine. In an embodiment, the HDAC inhibitor is Compound J, or a pharmaceutically acceptable salt thereof.

Kits

In other embodiments, kits are provided. Kits provided herein include package(s) comprising compounds or compositions provided herein. In some embodiments, kits comprise an HDAC inhibitor, or a pharmaceutically acceptable salt thereof, and azacitidine, or a pharmaceutically acceptable salt thereof.

The phrase "package" means any vessel containing compounds or compositions presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

Kits can further contain instructions for administering compounds or compositions provided herein to a patient. Kits also can comprise instructions for approved uses of compounds herein by regulatory agencies, such as the United States Food and Drug Administration. Kits can also contain labeling or product inserts for the compounds. The package(s) and/or any product insert(s) may themselves be approved by regulatory agencies. The kits can include compounds in the solid phase or in a liquid phase (such as buffers provided) in a package. The kits can also include buffers for preparing solutions for conducting the methods, and pipettes for transferring liquids from one container to another.

EXAMPLES

Examples have been set forth below for the purpose of illustration and to describe certain specific embodiments provided herein. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations and/or methods provided herein may be made without departing from the spirit provided herein and the scope of the appended claims. Definitions of the variables in the structures in the schemes herein are commensurate with those of corresponding positions in the formulae presented herein.

The synthesis of the compounds of Formula I (Compounds A and B) is provided in PCT/US2011/021982, which is incorporated herein by reference in its entirety. The synthesis of compounds of Formula II (Compounds C and D) is provided in PCT/US2011/060791, which is incorporated herein by reference in its entirety. The synthesis of compounds of Formula III, as well as Compound J is provided in U.S. application Ser. No. 14/069,741, which is incorporated herein by reference in its entirety. The synthesis of compounds of Formula IV (e.g., Compound G) is provided in International Application No. PCT/US2014/059863, which is incorporated herein by reference in its entirety.

Example 1

Synthesis of 2-(diphenylamino)-N-(7-(hydroxyamino)-7-oxoheptyl)pyrimidine-5-carboxamide (Compound A)

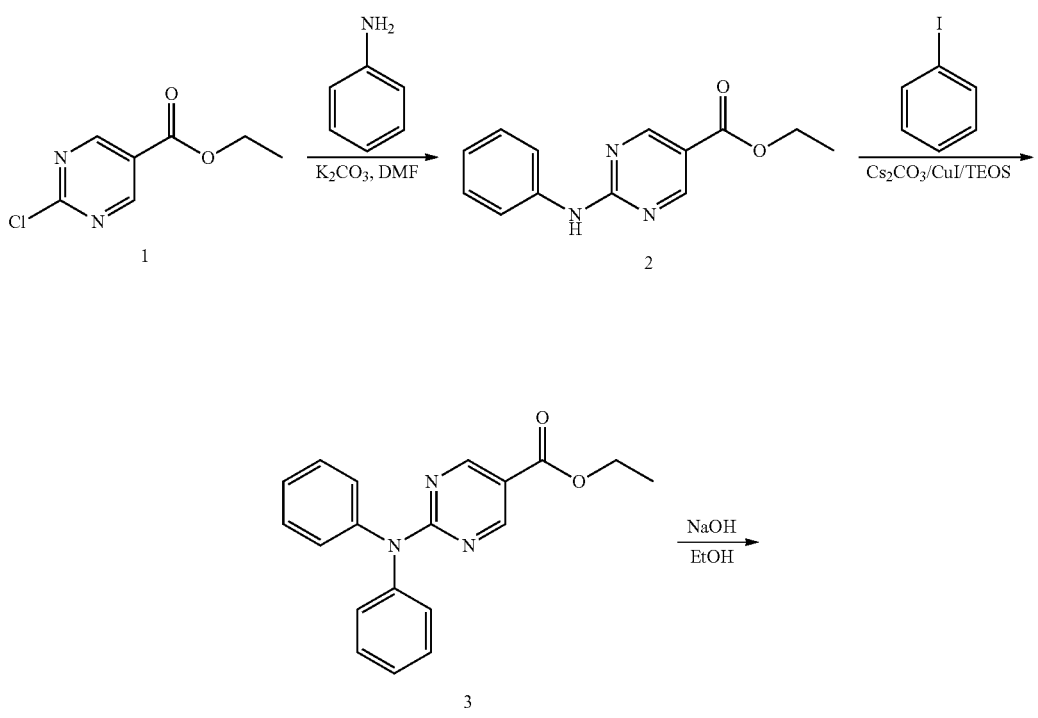

-continued

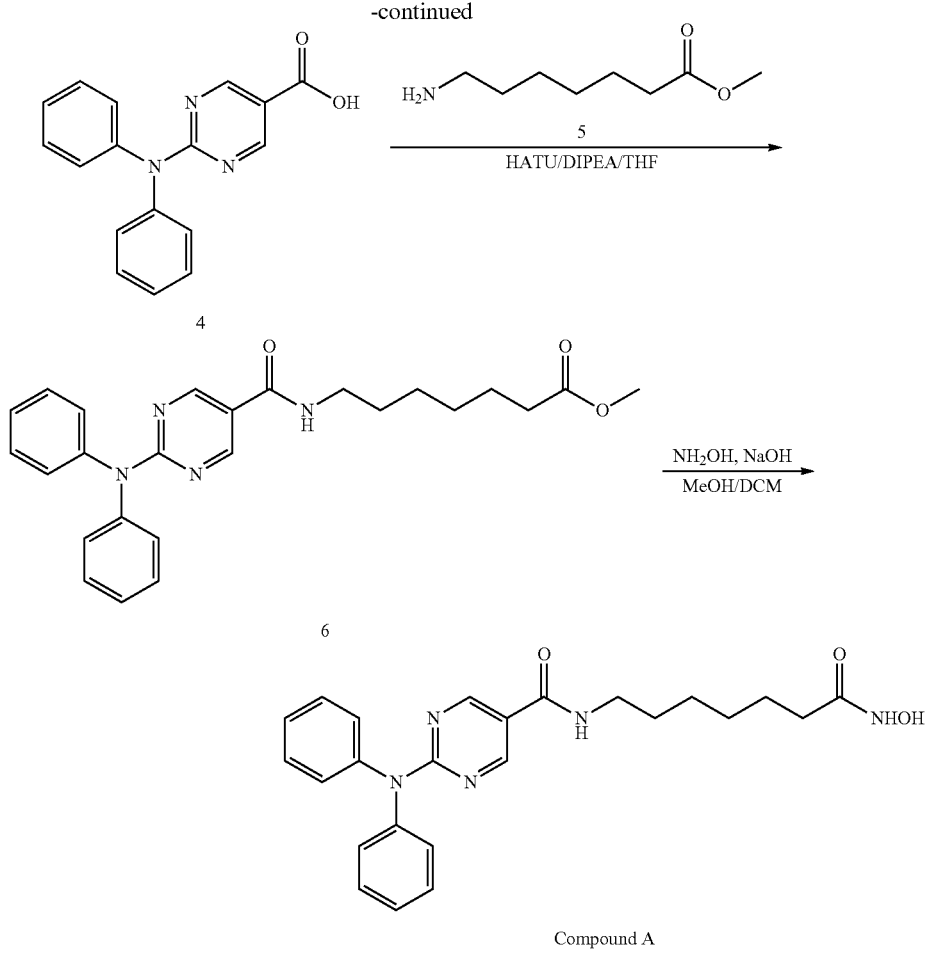

Compound A

Synthesis of Intermediate 2: A mixture of aniline (3.7 g, 40 mmol), compound 1 (7.5 g, 40 mmol), and $K_2CO_3$ (11 g, 80 mmol) in DMF (100 ml) was degassed and stirred at 120° C. under $N_2$ overnight. The reaction mixture was cooled to r.t. and diluted with EtOAc (200 ml), then washed with saturated brine (200 ml×3). The organic layers were separated and dried over $Na_2SO_4$, evaporated to dryness and purified by silica gel chromatography (petroleum ethers/EtOAc=10/1) to give the desired product as a white solid (6.2 g, 64%).

Synthesis of Intermediate 3: A mixture of compound 2 (6.2 g, 25 mmol), iodobenzene (6.12 g, 30 mmol), CuI (955 mg, 5.0 mmol), $Cs_2CO_3$ (16.3 g, 50 mmol) in TEOS (200 ml) was degassed and purged with nitrogen. The resulting mixture was stirred at 140° C. for 14 hrs. After cooling to r.t., the residue was diluted with EtOAc (200 ml). 95% EtOH (200 ml) and $NH_4F$—$H_2O$ on silica gel [50 g, pre-prepared by the addition of $NH_4F$ (100 g) in water (1500 ml) to silica gel (500 g, 100-200 mesh)] was added, and the resulting mixture was kept at r.t. for 2 hrs. The solidified materials were filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4: 2N NaOH (200 ml) was added to a solution of compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layers were separated, washed with water (2×100 ml), brine (2×100 ml), and dried over $Na_2SO_4$. Removal of the solvent gave a brown solid (2.5 g, 92%).

Synthesis of Intermediate 6: A mixture of compound 4 (2.5 g, 8.58 mmol), compound 5 (2.52 g, 12.87 mmol), HATU (3.91 g, 10.30 mmol), and DIPEA (4.43 g, 34.32 mmol) was stirred at r.t. overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide (Compound A): A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at r.t. for 20 min. After removal of the solvent, the mixture was neutralized with 1M HCl to give a white precipitate. The crude product was filtered and purified by pre-HPLC to give a white solid (950 mg, 48%).

Example 2

Synthesis of 2-((2-chlorophenyl)(phenyl)amino)-N-(7-(hydroxyamino)-7-oxoheptyl)pyrimidine-5-carboxamide (Compound B)

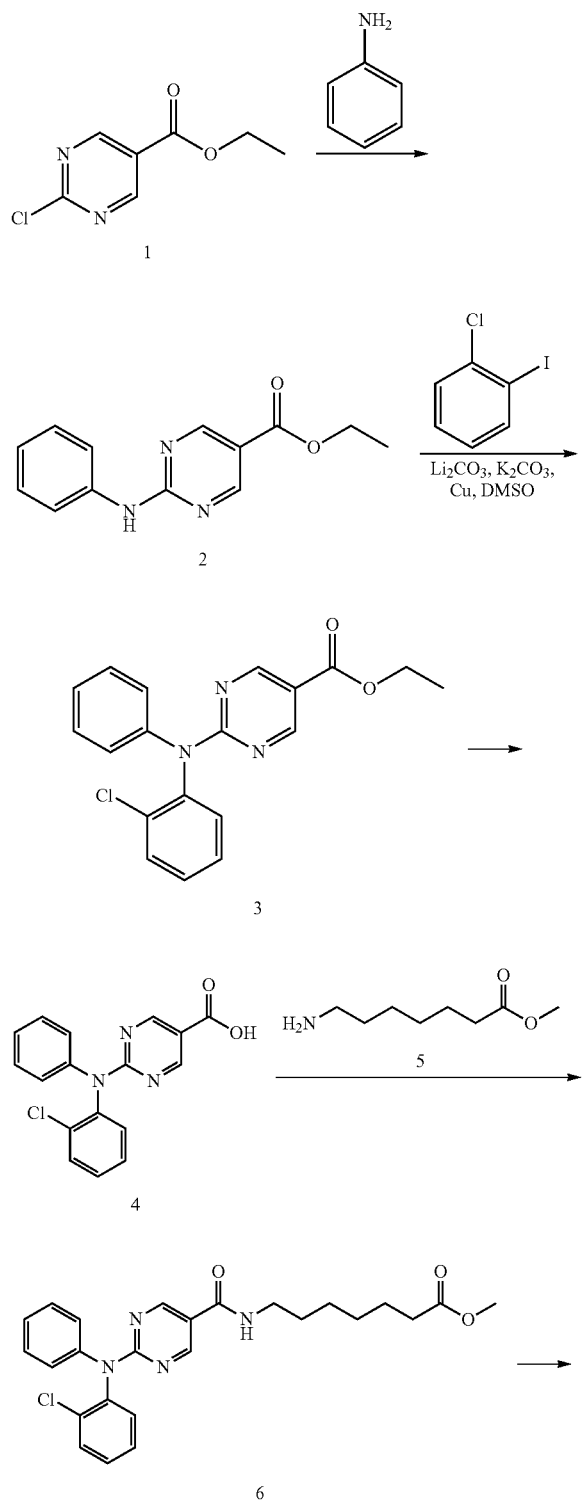

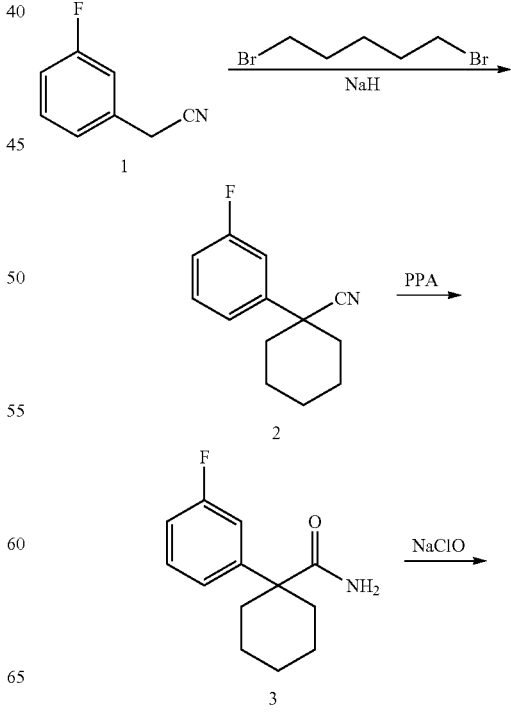

Compound B

Synthesis of Intermediate 2: See synthesis of intermediate 2 in Example 1.

Synthesis of Intermediate 3: A mixture of compound 2 (69.2 g, 1 equiv.), 1-chloro-2-iodobenzene (135.7 g, 2 equiv.), $Li_2CO_3$ (42.04 g, 2 equiv.), $K_2CO_3$ (39.32 g, 1 equiv.), Cu (1 equiv. 45 μm) in DMSO (690 ml) was degassed and purged with nitrogen. The resulting mixture was stirred at 140° C. Work-up of the reaction gave compound 3 at 93% yield.

Synthesis of Intermediate 4: See synthesis of intermediate 4 in Example 1.

Synthesis of Intermediate 6: See synthesis of intermediate 6 in Example 1.

Synthesis of 2-((2-chlorophenyl)(phenyl)amino)-N-(7-(hydroxyamino)-7-oxoheptyl)pyrimidine-5-carboxamide (Compound B): See synthesis of Compound A in Example 1.

Example 3

Synthesis of 2-((1-(3-fluorophenyl)cyclohexyl)amino)-N-hydroxypyrimidine-5-carboxamide (Compound C)

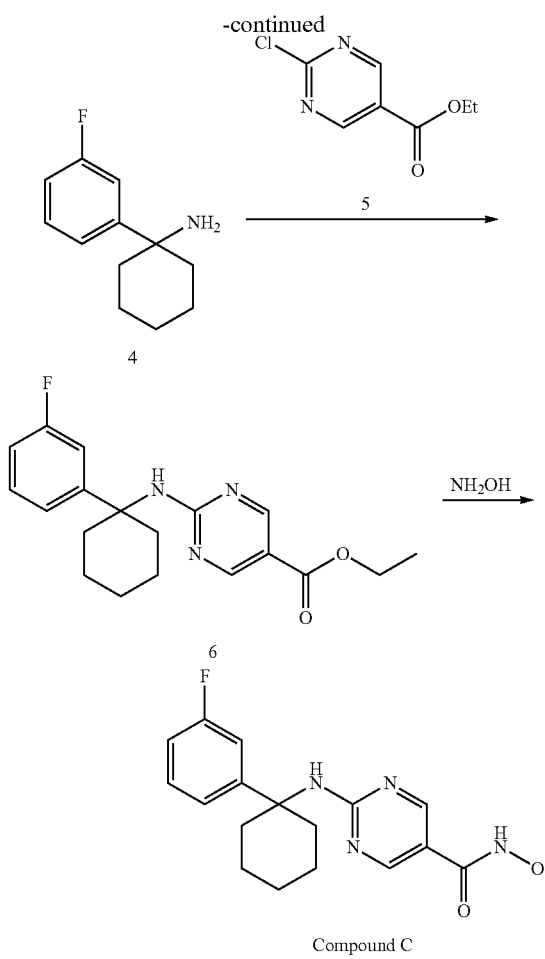

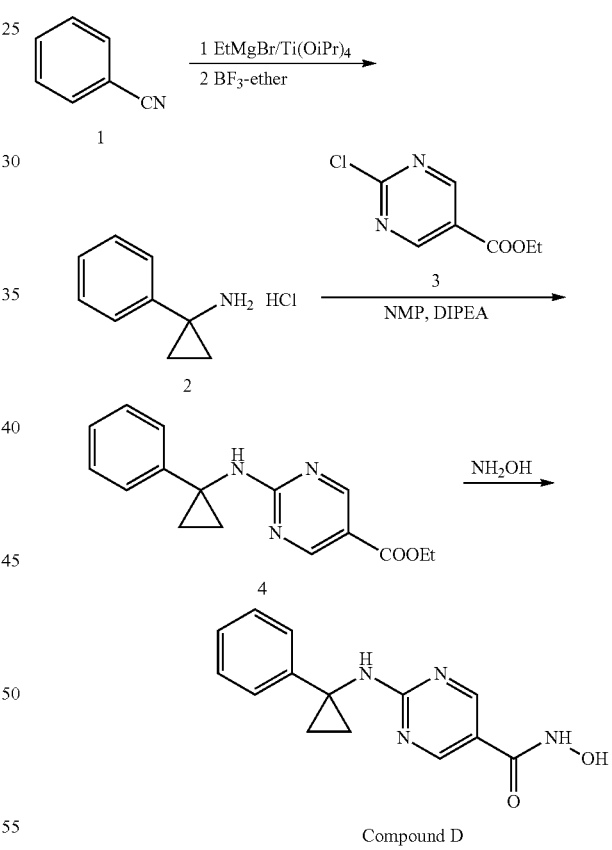

Compound C

Compound D

Synthesis of Intermediate 2: To a solution of compound 1 (100 g, 0.74 mol) in dry DMF (1000 ml) was added 1,5-dibromopentane (170 g, 0.74 mol). NaH (65 g, 2.2 eq) was added dropwise while the reaction was cooled in an ice bath. The resulting mixture was vigorously stirred overnight at 50° C. The suspension was carefully quenched with ice water and extracted with ethyl acetate (3×500 ml). The combined organic layers were concentrated to afford the crude product, which was purified by flash column chromatography to give compound 2 as pale solid (100 g, 67%).

Synthesis of Intermediate 3: A solution of compound 2 (100 g, 0.49 mol) in PPA (500 ml) was heated at 110° C. for about 5-6 hours. After completion, the resulting mixture was carefully adjusted to a pH of about 8-9 with sat.NaHCO₃ solution. The resulting precipitate was collected and washed with water (1000 ml) to afford compound 3 as white solid (95 g, 87%).

Synthesis of Intermediate 4: To a solution of compound 3 (95 g, 0.43 mol) in n-BuOH (800 ml) was added NaClO (260 ml, 1.4 eq). 3N NaOH (400 ml, 2.8 equiv.) was then added at 0° C. and the reaction was stirred overnight at r.t. The resulting mixture was extracted with EA (2×500 ml), and the combined organic layers washed with brine. The solvent was removed in vacuo to afford the crude product which was further purified by treatment with HCl salt to yield compound 4 as a white powder (72 g, 73%).

Synthesis of Intermediate 6: To a solution of compound 4 (2.29 g 10 mmol) in dioxane (50 ml) was added compound 5 (1.87 g, 1.0 equiv.) and DIPEA (2.58 g, 2.0 equiv.). The mixture was heated overnight at 110-120° C. The resulting mixture was directly purified on silica gel column to afford the coupled product, compound 6, as a white solid (1.37 g, 40%).

Synthesis of 2-((1-(3-fluorophenyl)cyclohexyl)amino)-N-hydroxypyrimidine-5-carboxamide (Compound C):

To a solution of compound 6 (100 mg, 0.29 mmol) in MeOH/DCM (10 ml, 1:1) was added 50% NH₂OH in water (2 ml, excess). Sat. NaOH in MeOH (2 ml, excess) was then added at 0° C. and the reaction was stirred for 3-4 hours. After completion, the resulting mixture was concentrated and acidified with 2N HCl to reach a pH of 4-5. The precipitate was collected and washed with water (10 ml) to remove excess NH₂OH. Drying the precipitate afforded 24-(1-(3-fluorophenyl)cyclohexyl)amino)-N-hydroxypyrimidine-5-carboxamide as a white powder (70 mg, 73%).

Example 4

Synthesis of N-hydroxy-2-((1-phenylcyclopropyl)amino)pyrimidine-5-carboxamide (Compound D)

Synthesis of Intermediate 2: A solution of compound 1, benzonitrile, (250 g, 1.0 equiv.), and Ti(OiPr)₄ (1330 ml, 1.5 equiv.) in MBTE (3750 ml) was cooled to about −10 to −5° C. under a nitrogen atmosphere. EtMgBr (1610 ml, 3.0M, 2.3 equiv.) was added dropwise over a period of 60 min., during which the inner temperature of the reaction was kept below 5° C. The reaction mixture was allowed to warm to 15-20° C. for 1 hr. BF₃-ether (1300 ml, 2.0 equiv.) was added dropwise over a period of 60 min., while the inner temperature was maintained below 15° C. The reaction mixture was stirred at 15-20° C. for 1-2 hr. and stopped when a low level of benzonitrile remained. 1N HCl (2500 ml) was added dropwise while maintaining the inner temperature below 30° C. NaOH (20%, 3000 ml) was added dropwise to bring the pH to about 9.0, while still maintaining a temperature below 30° C. The reaction mixture was extracted with MTBE (3 L×2) and EtOAc (3 L×2), and the combined organic layers were dried with anhydrous Na$_2$SO$_4$ and concentrated under reduced pressure (below 45° C.) to yield a red oil. MTBE (2500 ml) was added to the oil to give a clear solution, and upon bubbling with dry HCl gas, a solid precipitated. This solid was filtered and dried in vacuum yielding 143 g of compound 2.

Synthesis of Intermediate 4: Compound 2 (620 g, 1.0 equiv) and DIPEA (1080 g, 2.2 equiv. were dissolved in NMP (3100 ml) and stirred for 20 min. Compound 3 (680 g, 1.02 equiv.) was added and the reaction mixture was heated to about 85-95° C. for 4 hrs. The solution was allowed to slowly cool to r.t. This solution was poured onto H$_2$O (20 L) and much of the solid was precipitated out from the solution with strong stirring. The mixture was filtered and the cake was dried under reduced pressure at 50° C. for 24 hr., yielding 896 g of compound 4 (solid, 86.8%).

Synthesis of N-hydroxy-2-((1-phenylcyclopropyl)amino) pyrimidine-5-carboxamide (Compound D): A solution of MeOH (1000 ml) was cooled to about 0-5° C. with stirring. NH$_2$OH HCl (1107 g, 10 equiv.) was added, followed by careful addition of NaOCH$_3$ (1000 g, 12.0 equiv.) The resulting mixture was stirred at 0-5° C. for one hr, and was filtered to remove the solid. Compound 4 (450 g, 1.0 equiv.) was added to the reaction mixture in one portion, and stirred at 10° C. for two hours until compound 4 was consumed. The reaction mixture was adjusted to a pH of about 8.5-9 through addition of HCl (6N), resulting in precipitation. The mixture was concentrated under reduced pressure. Water (3000 ml) was added to the residue with intense stirring and the precipitate was collected by filtration. The product was dried in an oven at 45° C. overnight (340 g, 79% yield).

Example 5

Synthesis of N-(2-amino-5-(thiophen-2-yl)phenyl)-2-cyclopropyl-1-(2-morpholinoethyl)-1H-indole-5-carboxamide (Compound E)

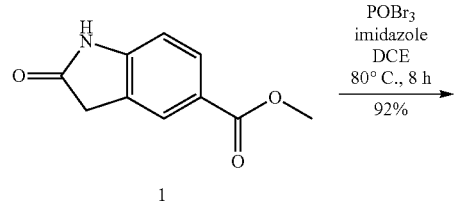

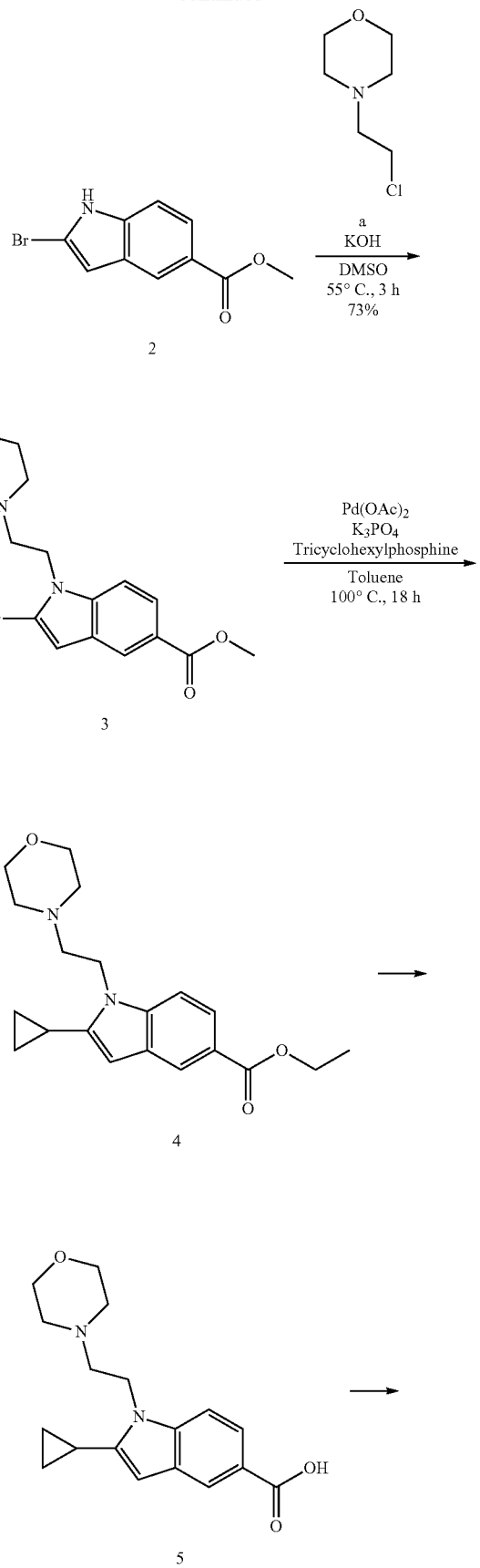

-continued

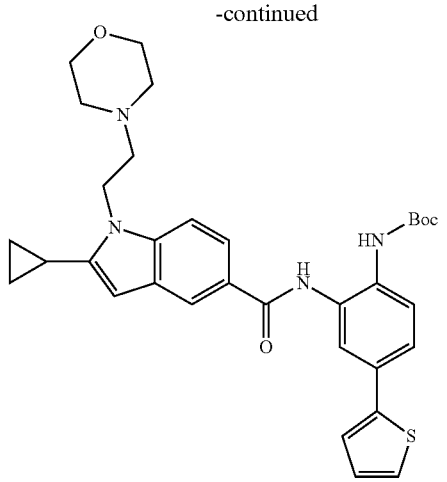

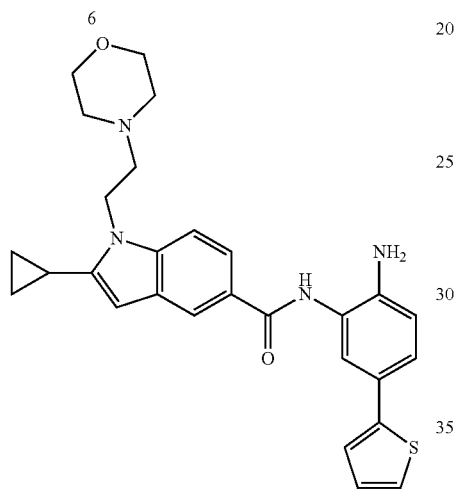

Compound E

Experimental Procedure

Step 1:

To a solution of compound 1 in DCE was added POBr$_3$ and imidazole. The reaction was stirred at 80° C. overnight. Water and DCM were added to the reaction, and the organic layer was separated, washed with brine, and dried under reduced pressure to give compound 2.

Step 2:

To a solution of compound 2 in DMSO was added compound a and KOH. The resulting reaction mixture was stirred at 45° C. for 4 h, quenched with H$_2$O, and extracted with EA. The combined organic layers were purified by gel chromatography to yield the desired product, compound 3.

Step 3:

A mixture of compound 3, cyclopropyl boronic acid, Pd(OAc)$_2$, tricyclohexylphosphine, and K$_3$PO$_4$ in toluene and water was stirred at 100° C. under N$_2$ atmosphere overnight. The mixture was cooled, filtered, and concentrated to obtain a residue, which was purified by Prep-TLC to get compound 4.

Step 4:

A mixture of compound 4 and NaOH in EtOH and THF was stirred at 60° C. for 5 h. The mixture was concentrated to obtain a residue, to which was added aq. sat. citric acid and extracted with EA. The organic layers were separated, dried, filtered and concentrated to obtain compound 5.

Step 5:

A mixture of compound 5, tert-butyl 2-amino-4-(thiophen-2-yl)phenylcarbamate, HOAT, EDCI, and DIPEA in DMF was stirred at 55° C. for overnight. Water was added to the mixture, and extracted with EA. The organic layers were separated, dried, filtered, and concentrated to get a residue, which was purified by Prep-TLC to afford compound 6.

Step 6:

To a solution of compound 6 in DCM was added TFA and stirred at r.t. for 1 h. The mixture was concentrated to obtain a residue, which was purified by Prep-HPLC to afford compound 7. $^1$H NMR (500 MHz, DMSO) δ 9.63 (s, 1H), 8.16 (s, 1H), 7.79-7.73 (m, 1H), 7.51 (d, J=2.1 Hz, 2H), 7.36 (d, J=5.1 Hz, 1H), 7.29 (dd, J=8.3, 2.1 Hz, 1H), 7.25 (d, J=3.5 Hz, 1H), 7.05 (dd, J=5.0, 3.6 Hz, 1H), 6.82 (d, J=8.3 Hz, 1H), 6.24 (s, 1H), 5.12 (s, 2H), 4.43 (s, 2H), 3.57 (s, 5H), 2.77-2.58 (m, 2H), 2.09 (s, 1H), 1.02 (d, J=8.0 Hz, 2H), 0.76 (d, J=4.4 Hz, 2H). LCMS: m/z=487.2 (M+H)+.

Example 6

Synthesis of N-hydroxy-2-((4-phenyl-1-(phenylcarbamoyl)piperidin-4-yl)amino)pyrimidine-5-carboxamide (Compound G)

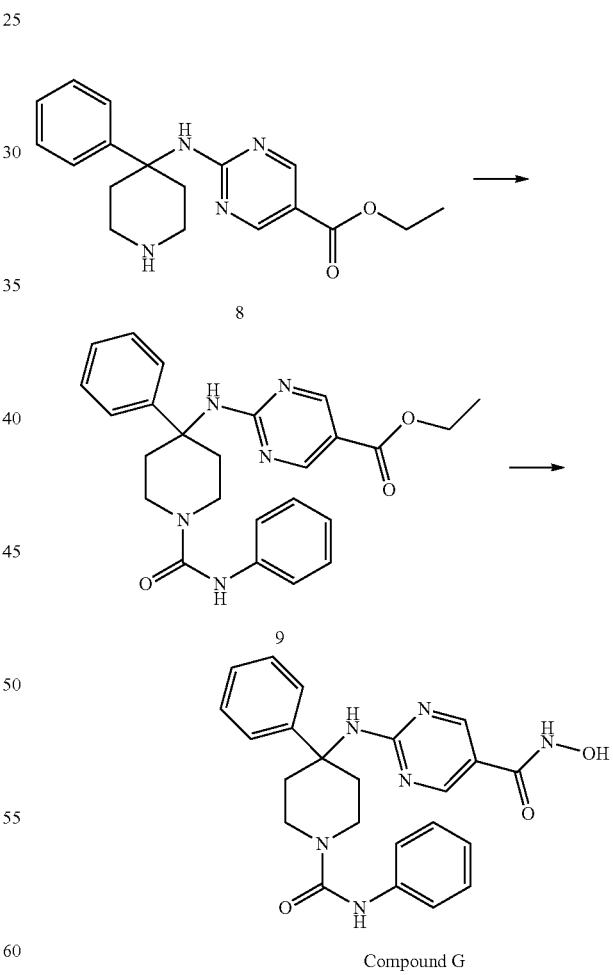

Compound G

Step 1:

To a solution of compound 8 (85 mg, 0.26 mmol) in THF (4 mL) was added isocyanatobenzene (46 mg, 0.39 mmol), DIPEA (0.2 ml) at r.t. The reaction was stirred for 2 hrs. and subsequently concentrated in vacuo to give compound 9 (80 g, yield: 69%).

Step 2:

To a solution of compound 9 (80 mg, 0.18 mmol) in MeOH (3 mL) and DCM (1 ml) at 0° C. was added NH$_2$OH (0.2 ml). The reaction was stirred for 10 mins, at which time NaOH/MeOH (0.4 ml) was added. The reaction was stirred for 2 hrs. The resulting reaction mixture was concentrated, adjusted to pH=5 using 2N HCl, extracted with EA (10 ml), and purified by Pre-HPLC to afford N-hydroxy-2-((4-phenyl-1-(phenylcarbamoyl)piperidin-4-yl)amino)pyrimidine-5-carboxamide (14 mg, 17%). $^1$H NMR (500 MHz, DMSO) δ 10.83 (s, 1H), 8.96 (s, 1H), 8.60 (s, 1H), 8.49 (s, 2H), 8.37 (s, 1H), 8.20 (s, 1H), 7.47-7.46 (d, J=7.6 Hz, 2H), 7.41-7.39 (d, J=7.4 Hz, 2H), 7.29-7.26 (t, J=7.7 Hz, 2H), 7.23-7.20 (m, J=7.7 Hz, 2H), 7.18-7.15 (t, J=7.3 Hz, 1H), 6.92 (t, J=7.3 Hz, 1H), 4.03 (d, J=13.2 Hz, 2H), 3.13 (t, J=12.1 Hz, 2H), 2.64 (d, J=13.0 Hz, 2H), 1.90 (t, J=11.0 Hz, 2H). LCMS: m/z=433 (M+H)$^+$.

Example 7

Synthesis of N-(2-amino-5-(thiophen-2-yl)phenyl)-2-(piperazin-1-yl)quinoline-6-carboxamide Compound J The preparation of Compound J is provided in U.S. patent application Ser. No. 14/069,741, which is summarized below.

Reaction Scheme:

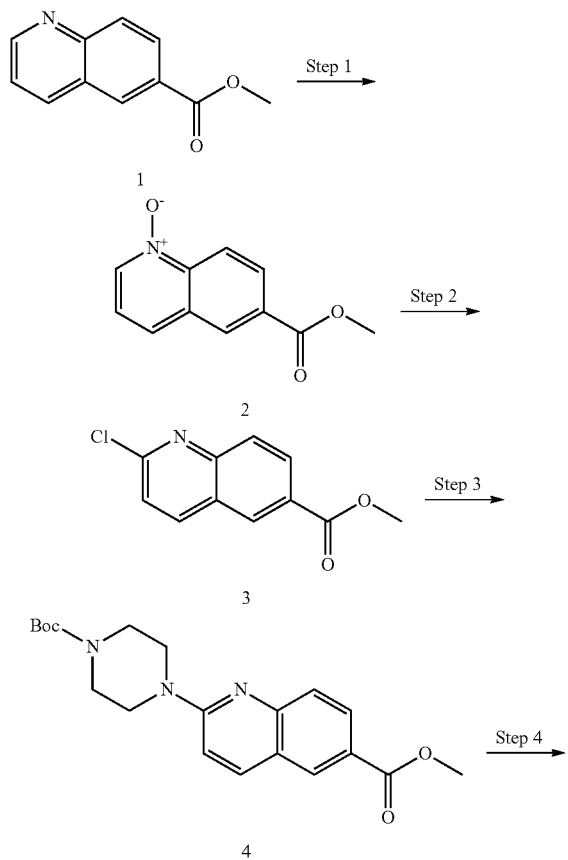

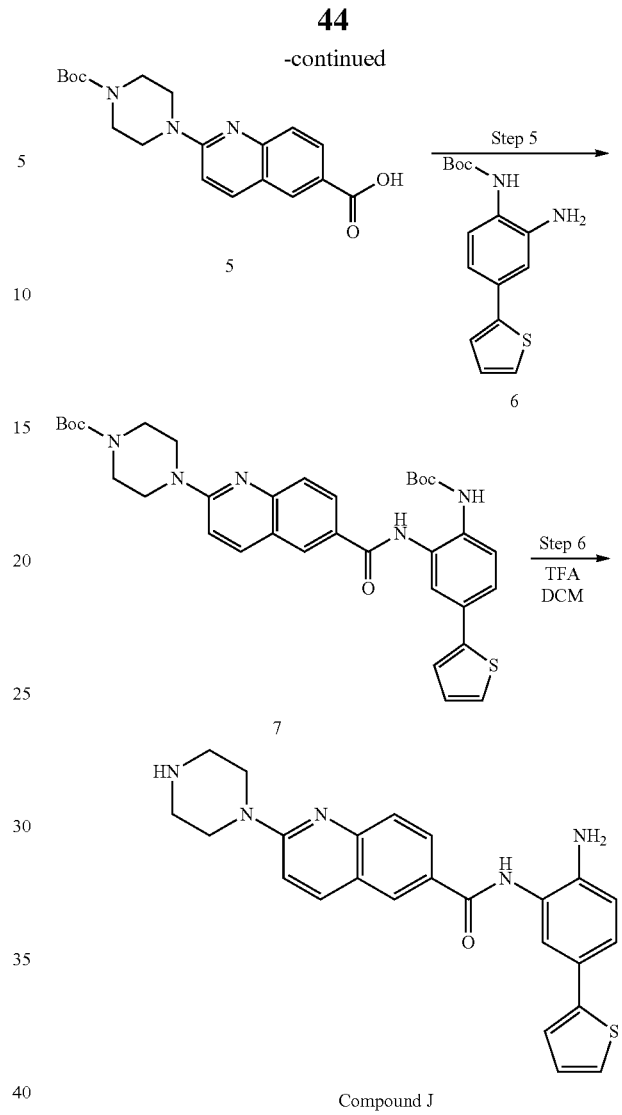

Compound J

Experimental Procedure

Step 1:

A mixture of compound 1 (10 g, 0.53 mol) and m-CPBA (18.4 g, 0.106 mol) in DCM (50 ml) is stirred at r.t. overnight. Aq. NaHCO$_3$ (40 ml, saturated) is added to the reaction mixture and stirred for 30 min. The organic layer is separated, dried, filtered and concentrated to obtain a residue, which can be re-crystallized in ethyl acetate (5 ml) to afford compound 2 as a light yellow solid.

Step 2:

To a solution of compound 2 (4.0 g, 0.020) and DMF (8 ml) in DCM is added SOCl$_2$ (8 ml) slowly at 0° C. and stirred at r.t. for 5 h. The resulting mixture is concentrated to obtain a residue, and DCM (50 ml) with Aq. NaHCO$_3$ (saturated, 20 ml) is added and stirred for 30 min. The organic layer is separated and concentrated to obtain a residue, which is purified by silica gel chromatography to afford compound 3 as a white solid.

Step 3:

A mixture of compound 3 (10 g, 0.045 mol), CuI (10 g, 0.53 mol), N-boc-piperazine (25 g, 0.135 mol) and K$_2$CO$_3$ (18.6 g, 0.135 mol) in DMSO (120 ml) is stirred at 100° C. overnight. Upon completion, as monitored by TLC (thin-layer chromatography), 300 ml of EA (ethyl acetate) is added, followed by filtration. Concentration of the mixture yields a residue, to which water (300 ml) and Aq. Citric acid (saturated, 30 ml) are added. Stirring at r.t. for 30 min., followed by filtration yields compound 4 as a yellow solid that can be used in the next step without purification.

Step 4:

A mixture of compound 4 (18 g, crude) and 2M NaOH (50 ml) in EtOH (100 ml) and THF (100 ml) is stirred at 70° C. for 4 h. TLC can be used to monitor the reaction. The reaction mixture is concentrated to a residue, to which water (300 ml) and aq. sat. citric acid (40 ml) are added. Subsequent filtration yields compound 5 as a yellow solid.

Step 5:

A mixture of compound 5 (1 equiv.), tert-butyl 2-amino-4-(thiophen-2-yl)phenylcarbamate (1 equiv.), HOAT (1.5 equiv.), EDCI (2 equiv.), and DIPEA (4 equiv.) in DMF is stirred at 55° C. overnight. Water is added to the mixture, and extracted with EA. The organic layers are separated, dried, filtered, and concentrated to yield a residue, which can be purified by by Prep-TLC to afford compound 7.

Step 6:

A mixture of compound 7 (95 mg 0.15 mmol) and TFA (2 ml) in 2 ml DCM is stirred at r.t. for 2 h. Evaporation of the solvent yields crude product which can be purified by HPLC to afford the white product, Compound J (19 mg, 30%). $^1$H NMR (500 MHz, DMSO) δ 9.79 (s, 1H), 8.42 (d, J=1.8 Hz, 1H), 8.17-8.09 (m, 2H), 7.60 (d, J=8.8 Hz, 1H), 7.51 (d, J=2.0 Hz, 1H), 7.36 (dd, J=5.1, 0.8 Hz, 1H), 7.33-7.28 (m, 2H), 7.25 (d, J=3.5 Hz, 1H), 7.06 (dd, J=5.0, 3.6 Hz, 1H), 6.83 (d, J=8.3 Hz, 1H), 5.18 (s, 2H), 3.73 (s, 4H), 2.89 (s, 4H). LCMS: m/z=430 (M+H)$^+$ Example 8

HDAC Enzyme Assays

Compounds for testing are diluted in DMSO to 50 fold the final concentration and a ten point three fold dilution series is made. The compounds are diluted in assay buffer (50 mM HEPES, pH 7.4, 100 mM Kill, 0.001% Tween-20, 0.05% BASE, 20 µM TEC) to 6 fold their final concentration. The HDAC enzymes (purchased from BPS Biosciences) are diluted to 1.5 fold their final concentration in assay buffer. The dipeptide substrate and trypsin at 0.05 µM final concentration are diluted in assay buffer at 6 fold their final concentration. The final enzyme concentrations to use in these assays are 3.3 ng/ml (HDAC1), 0.2 ng/ml (HDAC2), 0.08 ng/ml (HDAC3) and 2 ng/ml (HDAC6). The final substrate concentrations to use are 16 µM (HDAC1), 10 µM (HDAC2), 17 µM (HDAC3) and 14 µM (HDAC6). Five µl of compound and 20 µl of enzyme are added to wells of a black, opaque 384 well plate in duplicate. Enzyme and compound are incubated together at room temperature for 10 min. Five µl of substrate is added to each well, the plate is shaken for 60 seconds and placed into a Victor 2 microliter plate reader. The development of fluorescence is monitored for 60 min. and the linear rate of the reaction is calculated. The IC$_{50}$ is determined using Graph Pad Prism by a four parameter curve fit.

Example 9

Synergy of HDAC Inhibitors and Azacitidine on AML Cells

Inhibition of HDAC or DNMT (DNA methyltransferase) has been shown to be cytotoxic to AML cells. Different HDAC inhibitors (Compound A and Compound C are HDAC6 selective, Compound E is HDAC1/2 selective, and Compound F is a control) and the DNMT inhibitor, azacitidine, were combined in an AML cell viability assay measured by a Cell Titer Glo Assay™. With the same amount of cultured AML cells in each well, serial dilutions of one compound were added into each row of the wells from left to right, and serial dilutions of the second compound were mixed into each column of these wells from top to bottom. Therefore, those AML cells on the testing plate were exposed to various combinations of the two compounds at different concentrations. The viable cells in each well were measured after 72 hours incubation at 37° C., and the percentage of unviable cells was calculated and normalized to the total cells. These values were reported as Fa (Fractional Activity), in the range of 0-1.0, to reflect cytotoxicity of the testing compounds, alone or in combinations. Combination Index (CI) values were calculated using the software CalcuSyn to determine whether a combination was synergistic (CI<1.0), additive (CI=1.0), or antagonistic (CI>1.0). The CI values were plotted as a function of Fa, as shown in FIGS. 1A-D. In order to avoid any possible false positives due to experimental data variability, a combination was determined "synergistic" only when CI<0.7, as shown in the shaded area of each graph. From these results, it was concluded that the tested combinations have a synergistic cytotoxic effect on AML cells, based on the synergy data from the three tested AML cell lines: HL-60, Kasumi-3 and THP-1. HDAC1/2 inhibition appears to have a more predominant effect than HDAC3 or HDAC6 because the most synergy was observed from the Compound E/azacitidine combination. These results are presented in FIGS. 1A-D, where the graph in the top left (FIG. 1A) shows data for azacitidine and Compound A in HL-60 cells, the graph in the top right (FIG. 1B) shows data for azacitidine and Compound C in HL-60 cells, the graph in the lower left (FIG. 1C) shows data for azacitidine and Compound E in HL-60 cells, and the graph in the lower right (FIG. 1D) shows data for azacitidine and Compound F in HL-60 cells. Thus, the data in FIGS. 1A-D show that azacitidine shows significant synergistic cell killing with Compound A and other HDAC isoform inhibitors in AML cell lines (Kasumi-3, HL-60, and THP-1). The synergism is driven predominantly by HDAC1/2 inhibition.

Example 10

HDAC Inhibition Increases Apoptosis and Suppresses AML/ETO in AML

Figure 2A:
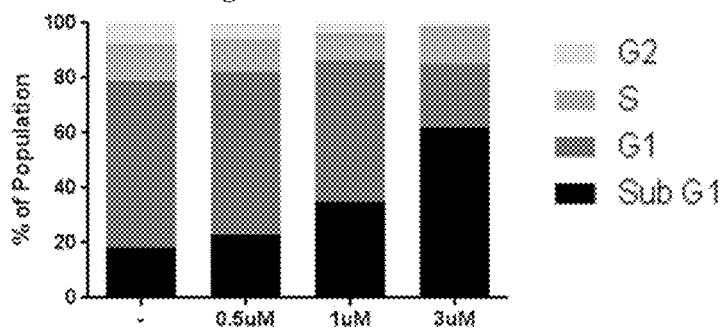
FIGS. 2A-D are a set of three graphs and pictures showing that HDAC inhibition increases apoptosis and suppresses AML1/ETO in AML.
Figure 2B:
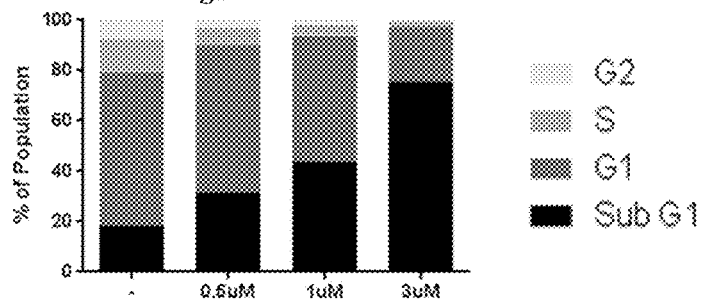
Figure 2C:
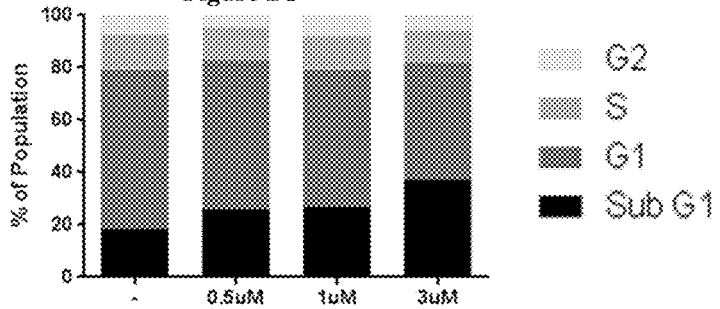

HDAC inhibition causing AML cell death (apoptosis) was measured by staining the AML cells with propidium iodide after the cells were exposed to different concentrations of the HDAC inhibitors. Four distinct cell populations, G1, S, G2, and sub-G1, were separated and quantified based on their propidium iodide staining patterns. The sub-G1 cells are those dying or dead cells, and the percentage of this population was a reflection of the tested compound cytotoxicity. Increased amount of sub-G1 cells as the function of increased concentrations of HDAC inhibitors, especially the HDAC1/2 selective inhibitor Compound E, suggested HDAC1/2 mediated AML cytotoxicity. These results are presented in FIGS. 2A-C, which shows data for the Kasumi-1 cell cycle at 72 hours. FIG. 2A shows data for Compound B, FIG. 2B shows data for Compound G, and FIG. 2C shows data for Compound E.

Figure 2D:
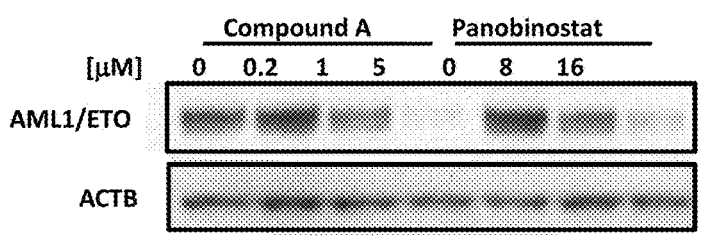
Figure 3A:
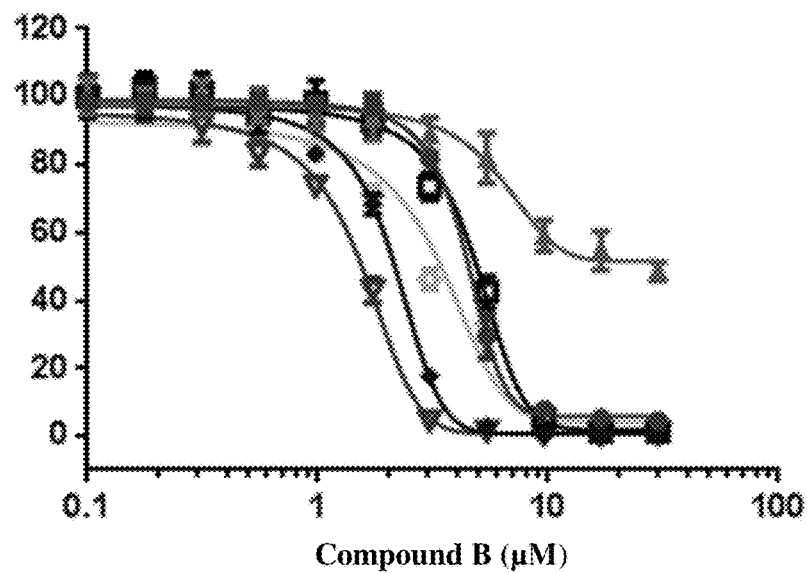
FIGS. 3A-D are a set of four graphs that show the single agent activity on viability in AML cell lines. 6 AML cell lines: HL-60 (large filled circles), THP-1 (upright filled triangles), MV-4-11 (small filled diamonds), Kasumi-1 (open squares), NB4 (open upside-down triangles), and MOLM-13 (open diamonds) were exposed to increasing concentrations of either Compound B (FIG. 3A), Compound A (FIG. 3B), Compound E (FIG. 3C), or azacitidine (FIG. 3D) to determine their response to drug treatment.
Figure 3B:
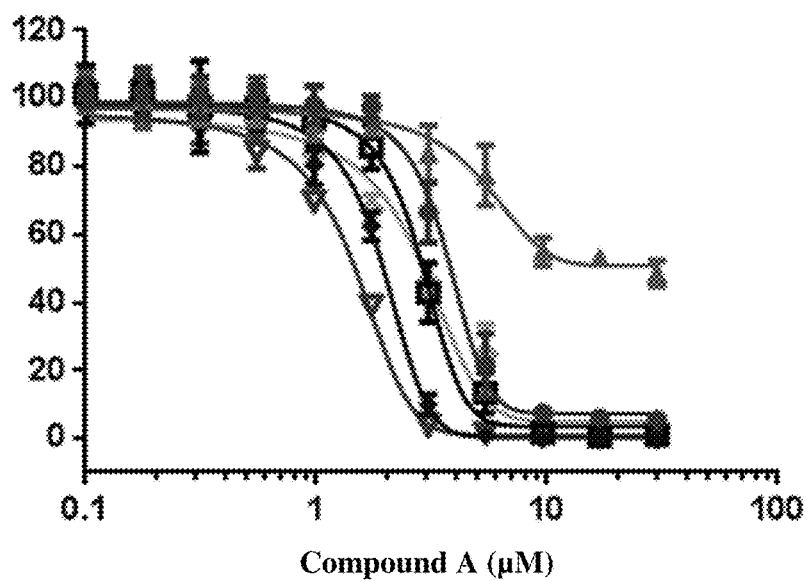
Figure 3C:
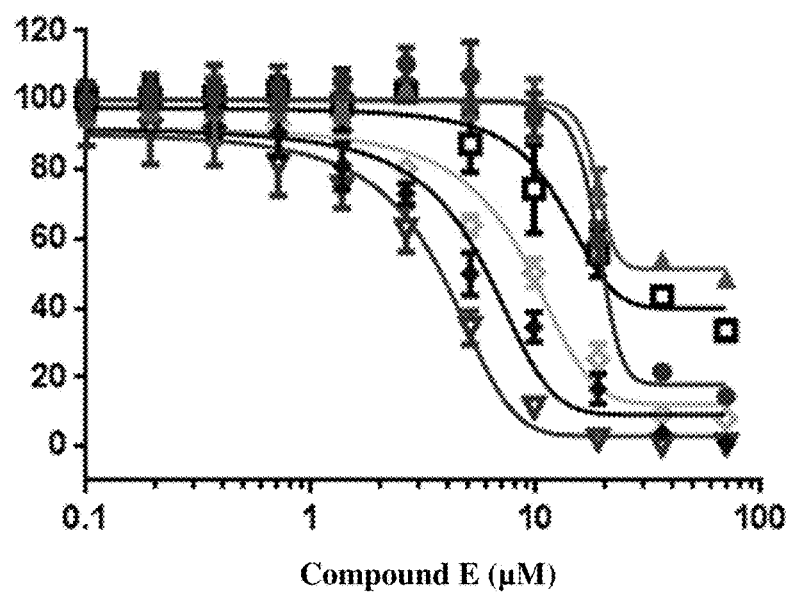
Figure 3D:
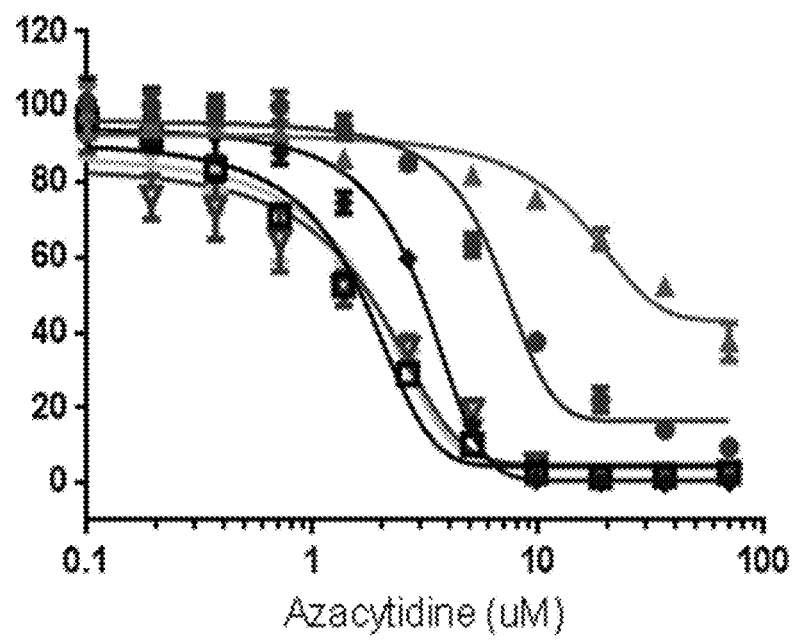

One type of AML has a signature chromosome translocation t(8;21) and therefore expression of a unique fusion protein AML1/ETO. This fusion protein has been reported as critical for AML cell growth, and the pan-HDAC inhibitor panobinostat is able to cause its loss in the AML cell line Kasumi-1, which has the t(8;21) translocation. In this study, Kasumi-1 cells were exposed to different concentrations of the HDAC inhibitor Compound A, or another HDAC1/2/6 selective inhibitor Compound G (data not shown), for 24 hours. The whole cell lysates were separated by SDS-PAGE (SDS-polyacrylamide gel electrophoresis) and transferred to a membrane (Western blot). The AML1/ETO fusion protein was detected on the membrane using an AML1 specific antibody. The results showed that Compound A and Compound G both decrease the amount of this fusion protein in a concentration dependent manner. These results are presented in FIG. 2D.

Example 11

Isoform Selective Histone Deacetylase (HDAC) Inhibitors Synergize in Combination with Azacitidine in Acute Myeloid Leukemia (AML)

AML is a heterogeneous group of hematopoietic stem cell disorders characterized by defects in myeloid differentiation and increased proliferation of neoplastic hematopoietic precursor cells. Aberrant epigenetic regulation plays an important role in the pathogenesis of AML. The DNA methyltransferase inhibitor azacitidine was approved for the treatment of myelodysplastic syndrome, which frequently progresses to AML.

HDAC inhibitors are emerging as promising agents for the treatment of AML. Isoform selective HDAC inhibitors have the potential to reduce the combination of drug toxicity and other side effects observed with non-selective inhibitors, while also realizing beneficial therapeutic effects. One example is ricolinostat (Compound A), a first-in-class orally available HDAC inhibitor that is 11-fold selective for HDAC6, synergizes with bortezomib (Blood, 20[210]: 4061) and immunomodulatory agents (Quayle, et al, ASH, 2013) in preclinical models of multiple myeloma, and has thus far demonstrated an improved safety and tolerability profile in Phase I trials (Raje, et al, EHA, 2014).

This work evaluated the combinatorial efficacy of azacitidine and HDAC inhibitors selective for either HDAC6 or HDAC1/2 on AML cells.

Time course studies demonstrated induction of differentiation, accumulation of cell cycle arrest, and initiation of apoptosis after prolonged exposure to HDAC inhibitors (see FIGS. 3-4).

FIGS. 3A-D show the single agent activity on viability in AML cell lines. Briefly, each of the following cell lines: HL-60, THP-1, MV-4-11, Kasumi-1, NB4, and MOLM-13 were exposed to increasing concentrations of either Compound B (FIG. 3A), Compound A (FIG. 3B), Compound E (FIG. 3C), or azacitidine (FIG. 3D) to determine their response to drug treatment. Compound B is about 10 times selective for HDAC6. Compound A is about 10 times selective for HDAC6. Compound E is selective for HDAC1/2. The panel of cell lines was also treated with azacitidine to measure their sensitivity. Thus, the data in FIGS. 3A-D show that AML cell lines are sensitive to HDAC inhibition.

Figure 4A:
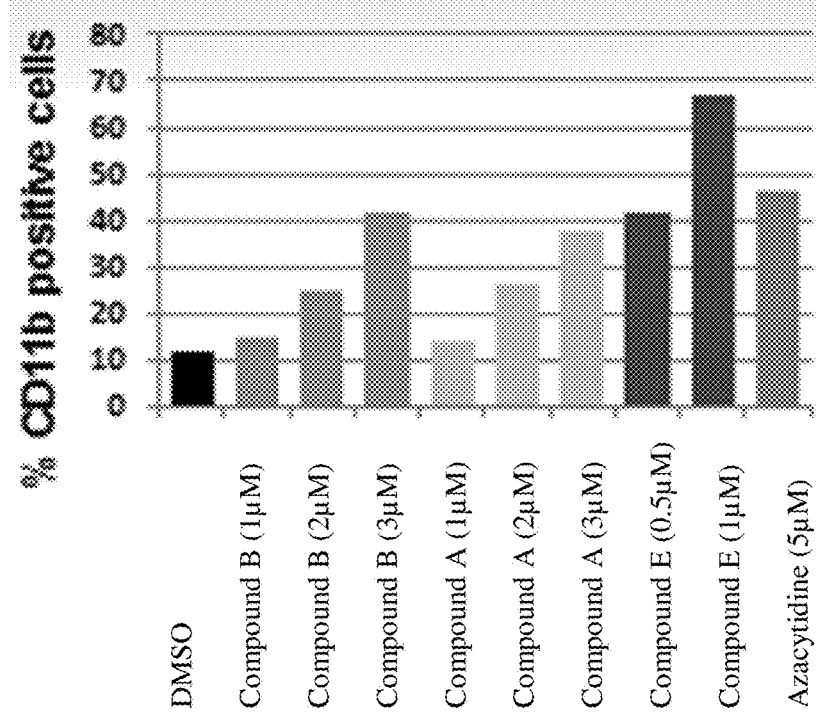
FIGS. 4A-F are a set of 6 graphs that show the single agent activity on differentiation and apoptosis in AML cell lines. 3 AML cell lines: HL-60 (FIGS. 4A and 4D), Kasumi-1 (FIGS. 4B and 4E), and NB4 (FIGS. 4C and 4F) were treated with the indicated concentrations of compounds.
Figure 4B:
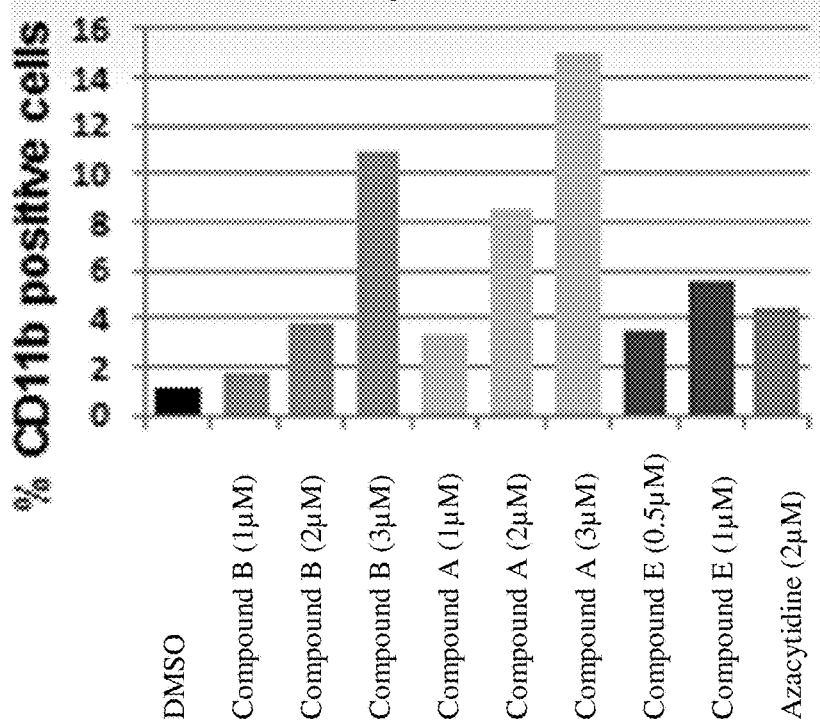
Figure 4C:
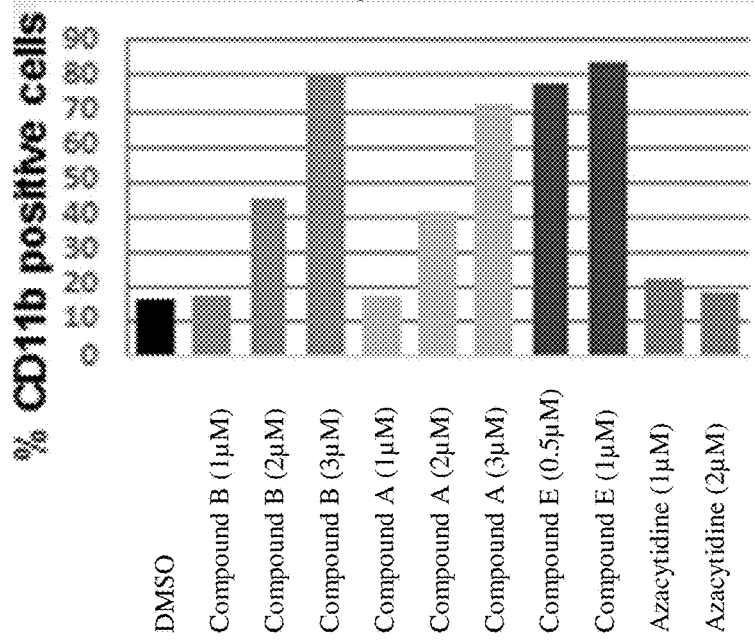
Figure 4D:
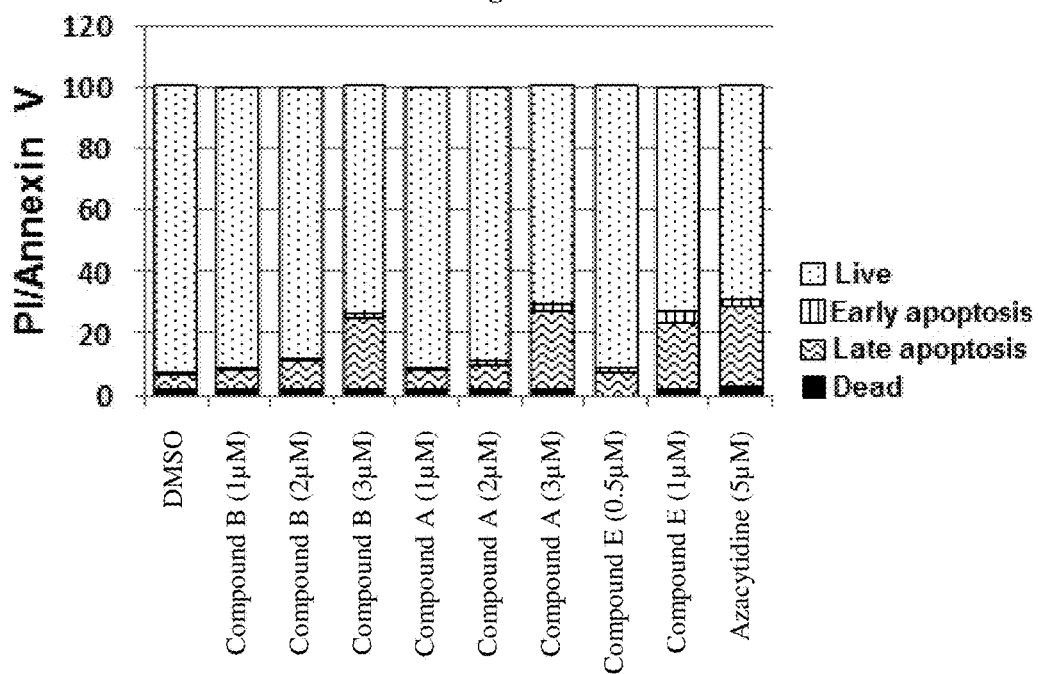
Figure 4E:
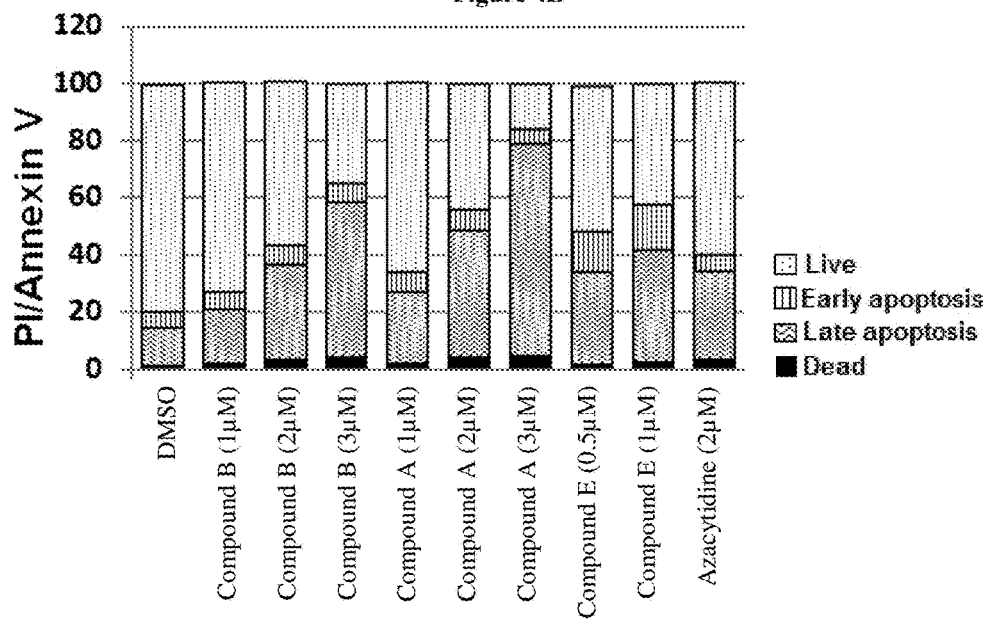
Figure 4F:
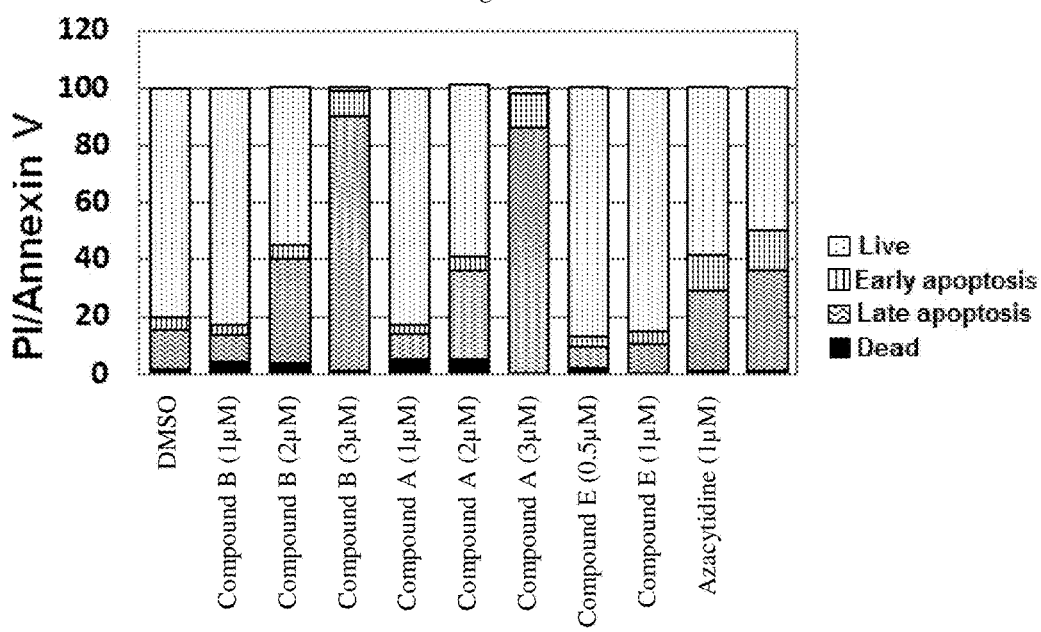
Figure 5A:
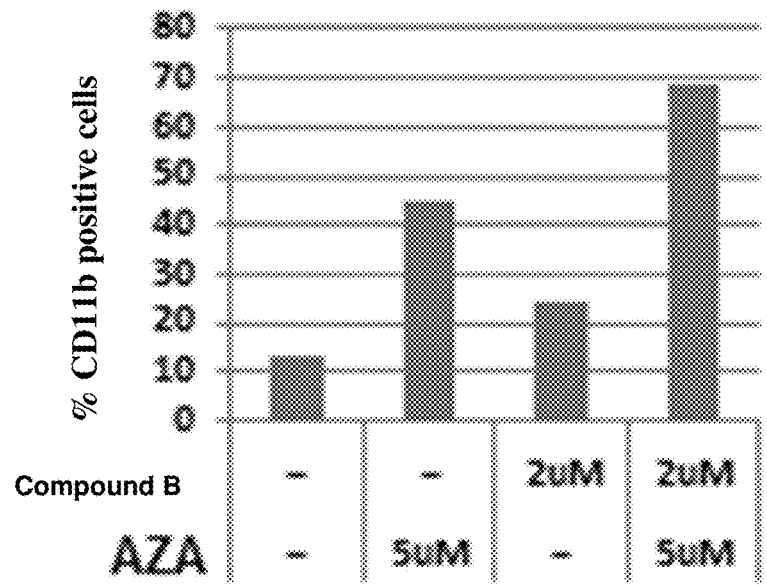
FIGS. 5A-F are a set of 6 graphs that show the combination of HDAC inhibitors and azacitidine in the HL-60 cell line. Cells were treated with DMSO, Compound B, Compound A, or Compound E as a single agent or in combination with azacitidine for 96 hours. Surface levels of the myeloid differentiation marker CD11b were determined (FIGS. 5A, 5C, 5E). Apoptosis was assessed by flow cytometry by measuring Annexin V binding and cellular permeability to propidium iodide at 96 hours post-treatment (FIGS. 5B, 5D, 5F). The relative fraction of cells that were alive, in early apoptosis, in late apoptosis, or dead was then determined.
Figure 5B:
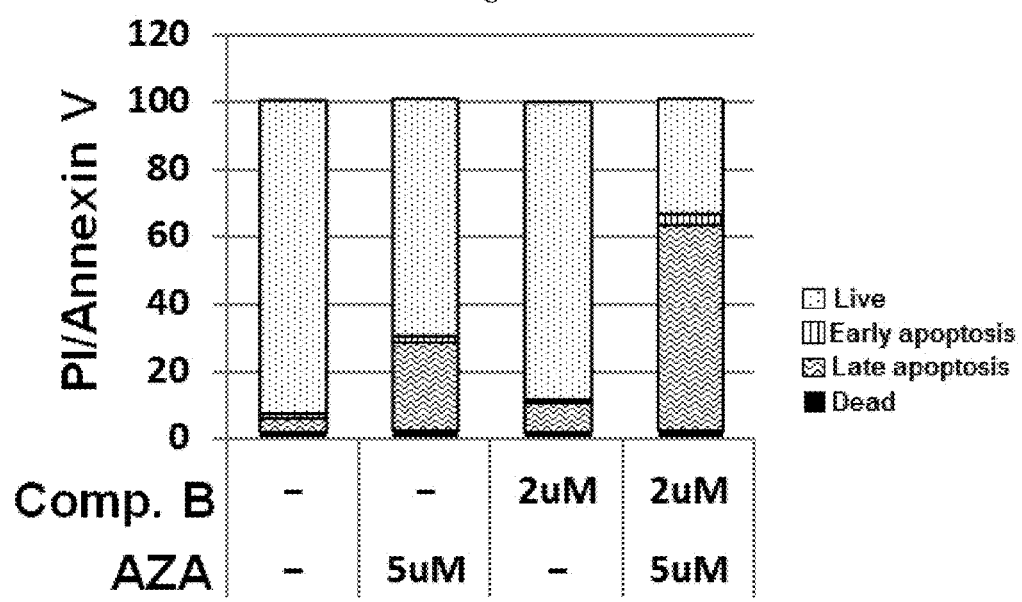
Figure 5C:
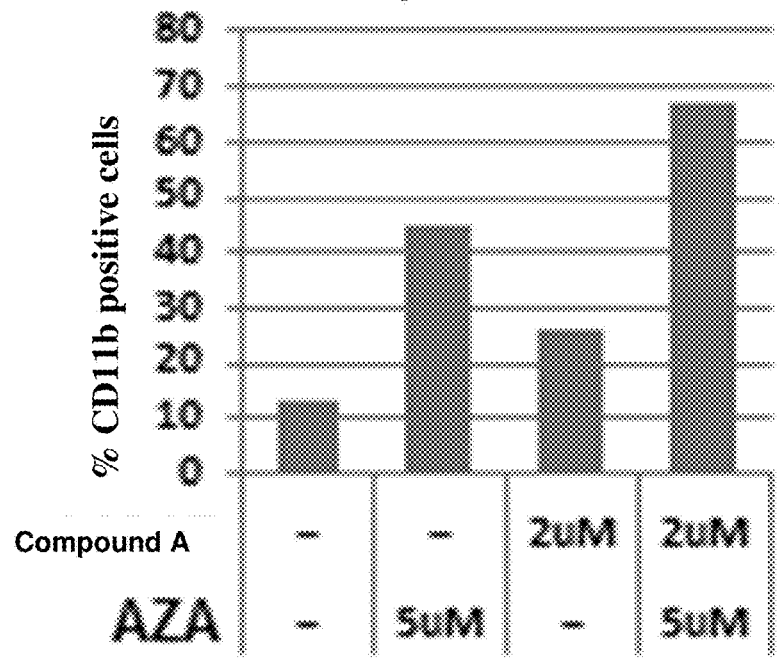
Figure 5D:
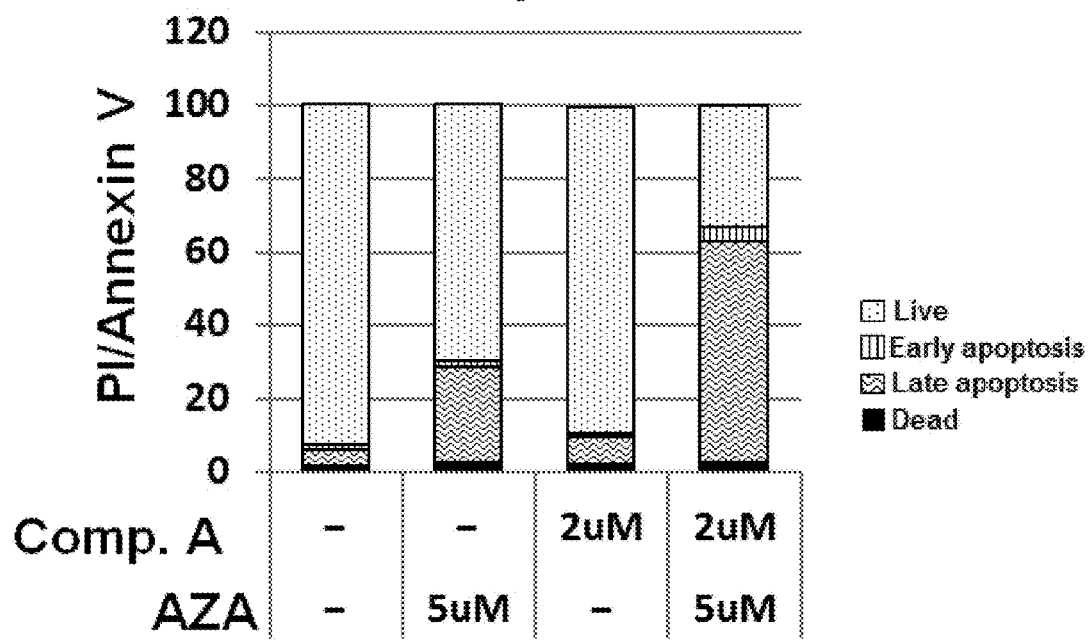
Figure 5E:
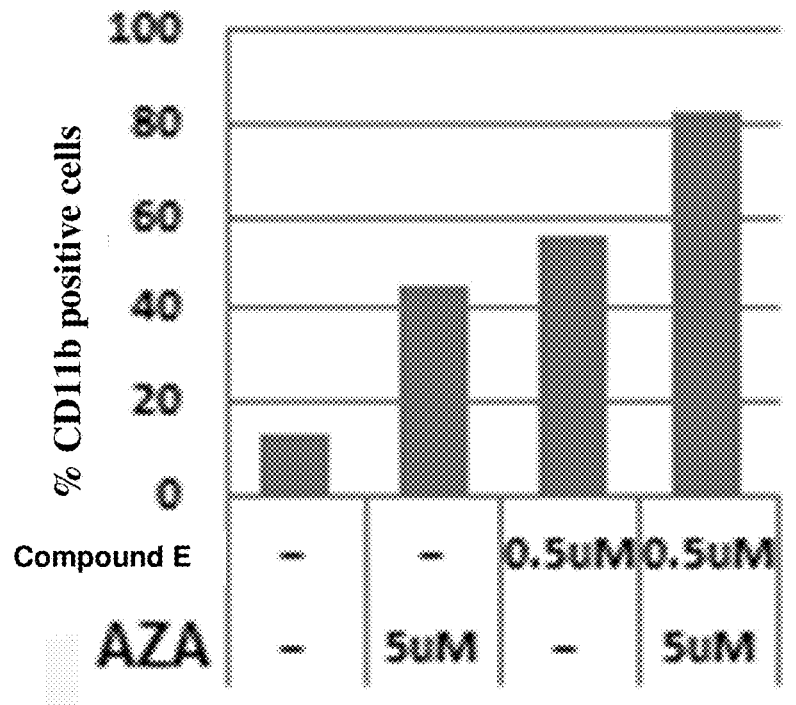
Figure 5F:
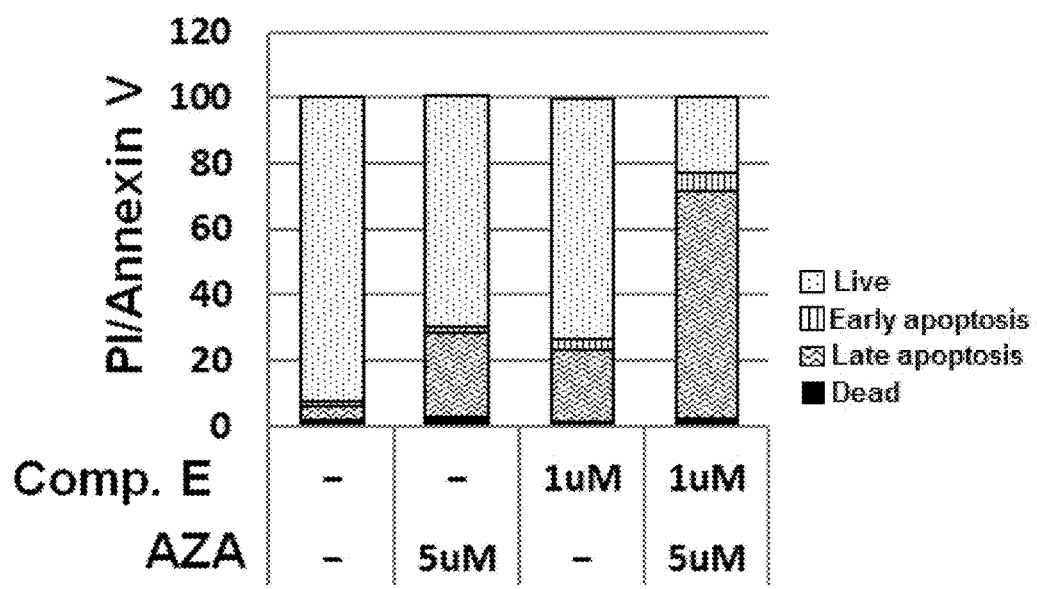

FIGS. 4A-F show the single agent activity on differentiation and apoptosis in AML cell lines. Briefly, the AML cell lines HL-60 (FIGS. 4A and 4D), Kasumi-1 (FIGS. 4B and 4E) and NB4 (FIGS. 4C and 4F) were treated with the indicated concentrations of compounds. In FIGS. 4A-C, surface levels of myeloid differentiation marker CD11b were determined by FACS at 72 hours post-treatment. Compound B, Compound A, and Compound E increased the percentage of CD11b positive cells in all three cell lines. Azacitidine increased CD11b positive cells in HL-60 (FIG. 4A) and Kasumi-1 cells (FIG. 4B) and had minimal effects in NB4 cells (FIG. 4C). In FIGS. 4D-F, apoptosis was assessed by flow cytometry by measuring Annexin V binding and cellular permeability to propidium iodide at 96 hours post-treatment. The relative fraction of cells that were alive, in early apoptosis, in late apoptosis, or dead was then determined. Treatment with Compound B, Compound A, and azacitidine resulted in an increase in apoptosis relative to control cells. Compound E induced apoptosis in HL-60 (FIG. 4D) and Kasumi-1 (FIG. 4E) cells, but had minimal effects in NB4 cells (FIG. 4F). Thus, the data in FIGS. 4A-F show that treatment of AML cells with Compound B, Compound A, Compound E, and azacitidine induced differentiation and apoptosis.

Combining HDAC inhibitors with azacitidine led to synergistic induction of differentiation and apoptosis in AML cells in vitro (see FIGS. 5-7).

FIGS. 5A-F show the combination of HDAC inhibitors and azacitidine in the HL-60 cell line. Briefly, cells were treated with DMSO, Compound B, Compound A, or Compound E as a single agent or in combination with azacitidine for 96 hours. Surface levels of CD11b (FIGS. 5A, 5C, 5E) and apoptosis (FIGS. 5B, 5D, 5F) was assessed by flow cytometry, as in FIG. 4. The combination of Compound B with azacitidine, Compound A with azacitidine, and Compound E with azacitidine resulted in synergistic increases of CD11b positive cells (FIGS. 5A, 5C, 5E) and apoptotic cells (FIGS. 5B, 5D, 5F) compared to single agent treatment. Thus, the data in FIGS. 5A-F show that the treatment of HL-60 cells with Compound B, Compound A, or Compound E plus azacitidine significantly induced differentiation and apoptosis.

Figure 6A:
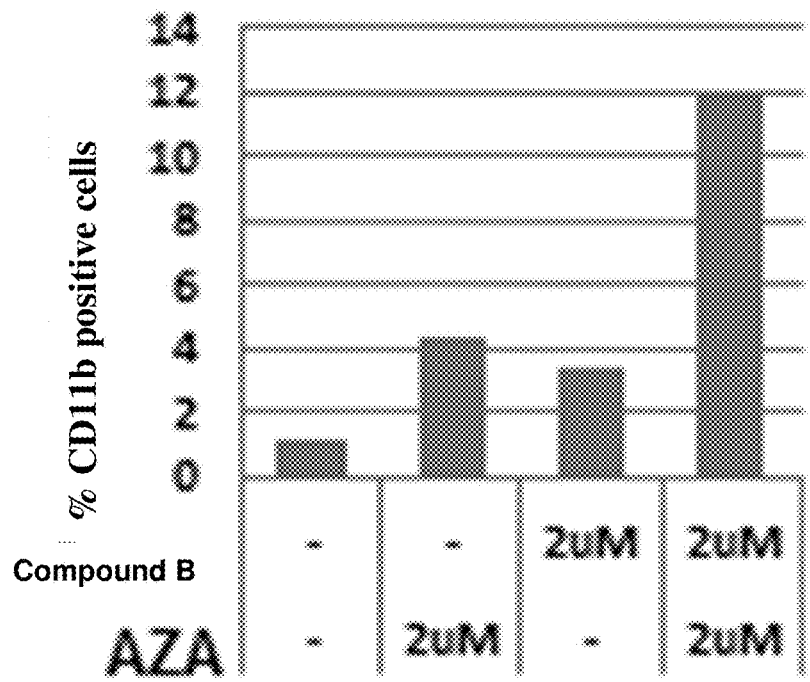
FIGS. 6A-F are a set of 6 graphs that show the combination of HDAC inhibitors and azacitidine in the Kasumi-1 cell line. Cells were treated with DMSO, Compound B, Compound A, or Compound E as a single agent or in combination with azacitidine at the indicated concentrations. Surface levels of the myeloid differentiation marker CD11b were determined (FIGS. 6A, 6C, 6E). Apoptosis was assessed by flow cytometry by measuring Annexin V binding and cellular permeability to propidium iodide at 96 hours post-treatment (FIGS. 6B, 6D, 6F). The relative fraction of cells that were alive, in early apoptosis, in late apoptosis, or dead was then determined.
Figure 6B:
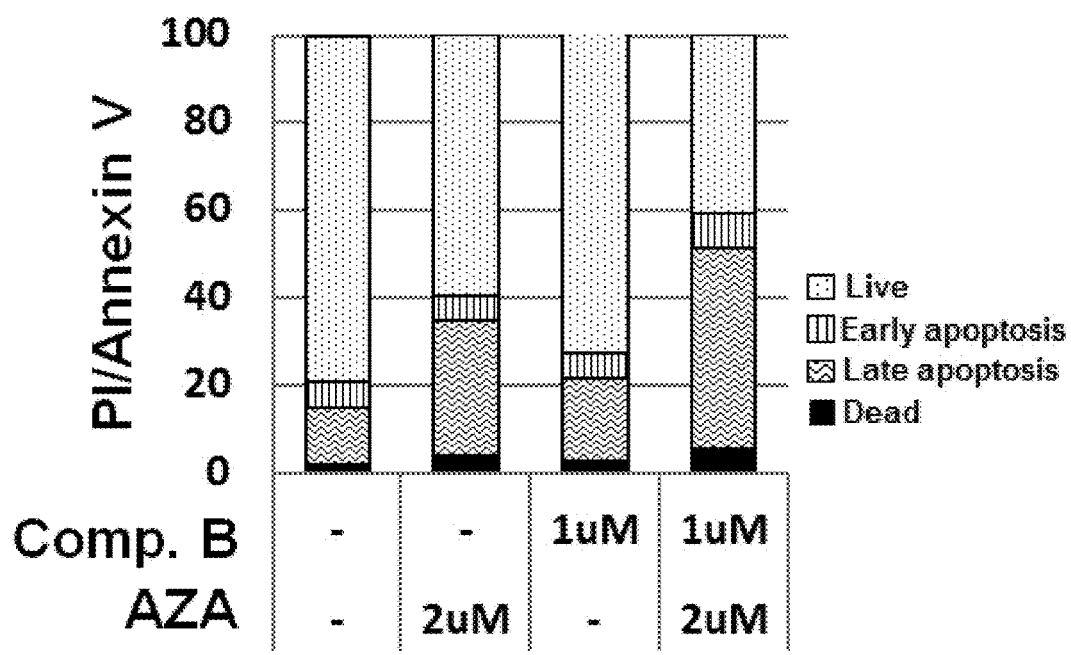
Figure 6C:
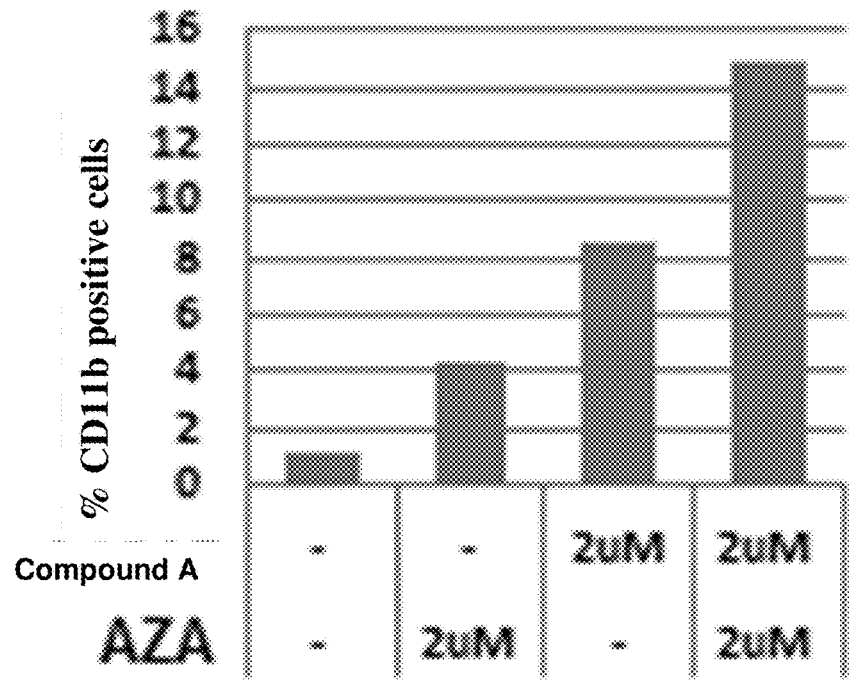
Figure 6D:
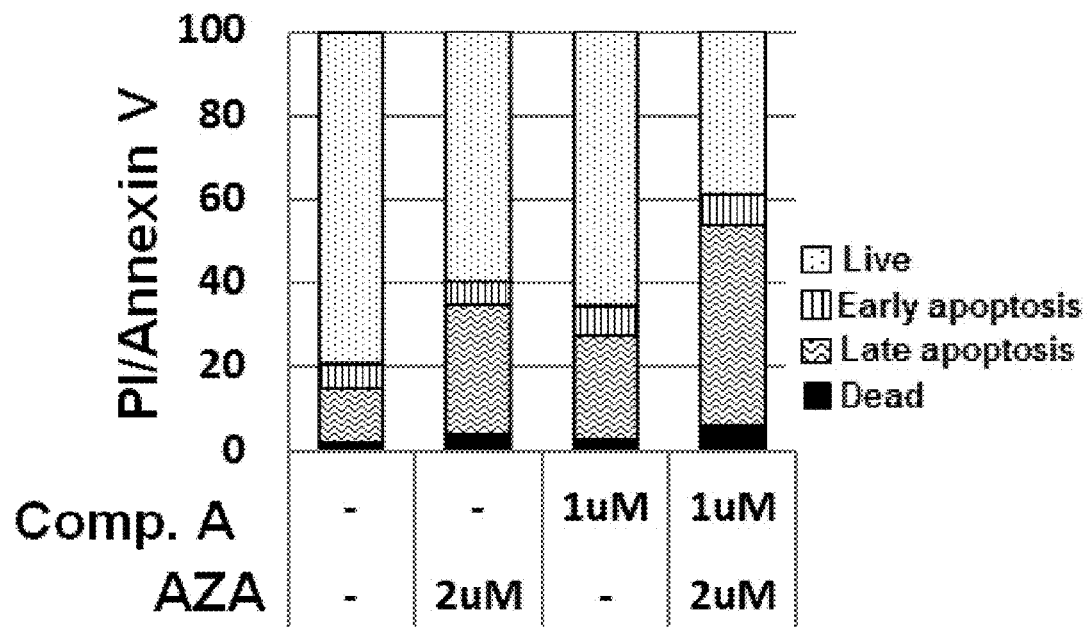
Figure 6E:
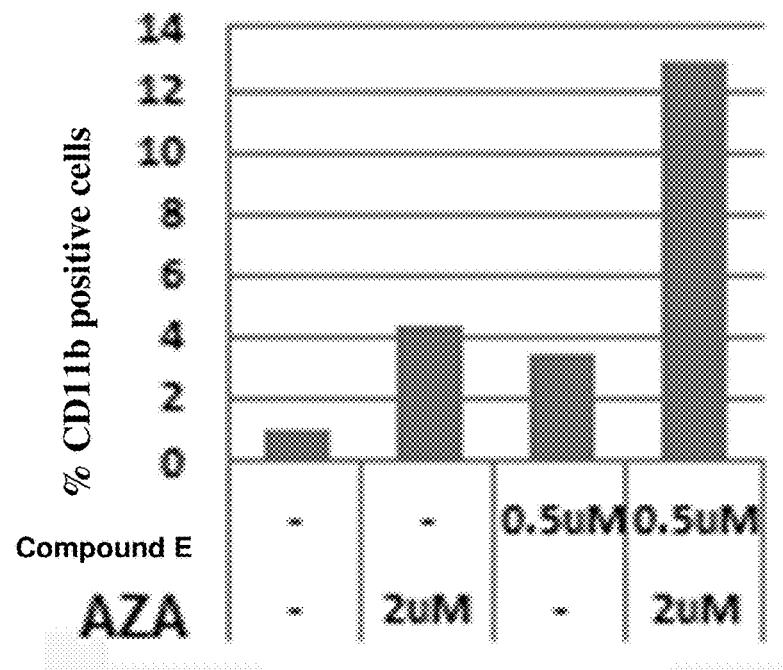
Figure 6F:
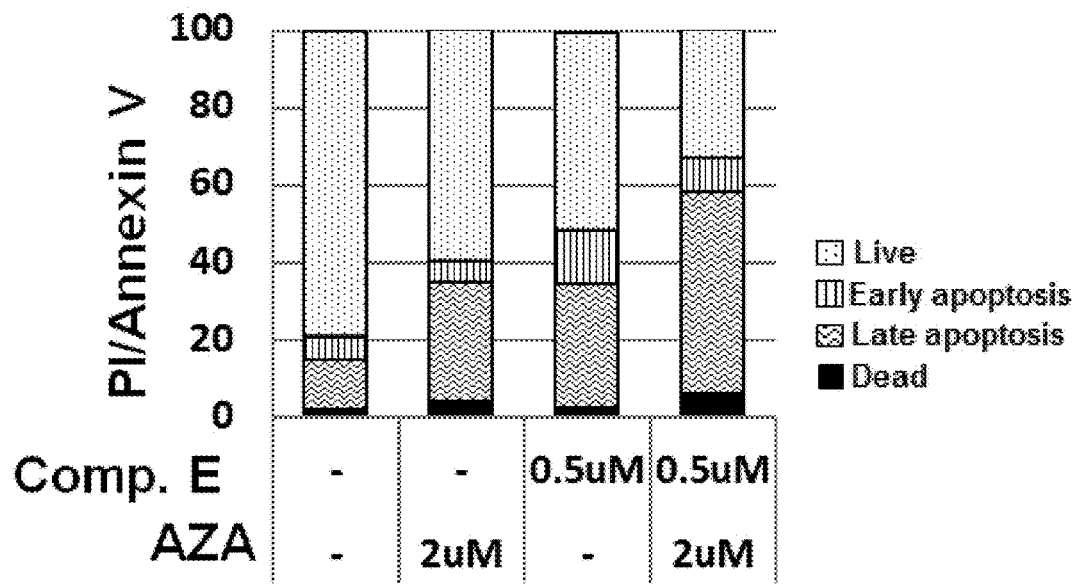

FIGS. 6A-F shows the combination of HDAC inhibitors and azacitidine in the Kasumi-1 cell line. Briefly, cells were treated with DMSO, Compound B, Compound A, or Compound E as a single agent or in combination with azacitidine at the indicated concentrations. Surface levels of CD11b were determined 72 hours post-treatment (FIGS. 6A, 6C, 6E), and apoptosis was assessed 96 hours post-treatment (FIGS. 6B, 6D, 6F). The combination of Compound B, Compound A, or Compound E with azacitidine resulted in synergistic increases of CD11b positive cells (FIGS. 6A, 6C, 6E) and apoptotic cells (FIGS. 6B, 6D, 6F) compared to single agent treatment. Thus, the data in FIGS. 6A-F show that the treatment of Kasumi-1 cells with Compound B, Compound A, or Compound E plus azacitidine significantly induced differentiation and apoptosis.

Figure 7A:
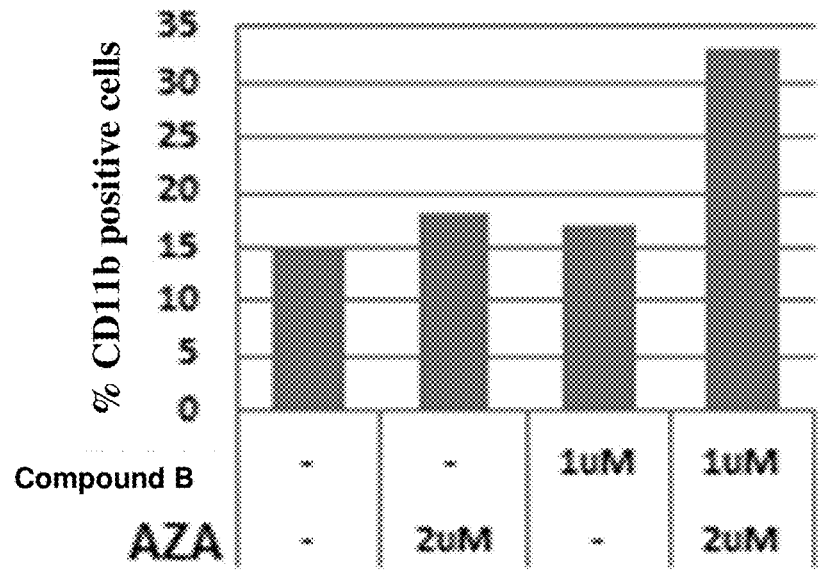
FIGS. 7A-F are a set of 6 graphs that show the combination of HDAC inhibitors and azacitidine in the NB4 cell line. Cells were treated with DMSO, Compound B, Compound A, or Compound E as a single agent or in combination with azacitidine at the indicated concentrations. Surface levels of the myeloid differentiation marker CD11b were determined (FIG. 7A, 7C, 7E). Apoptosis was assessed by flow cytometry by measuring Annexin V binding and cellular permeability to propidium iodide at 96 hours post-treatment (FIG. 7B, 7D, 7F). The relative fraction of cells that were alive, in early apoptosis, in late apoptosis, or dead was then determined.
Figure 7B:
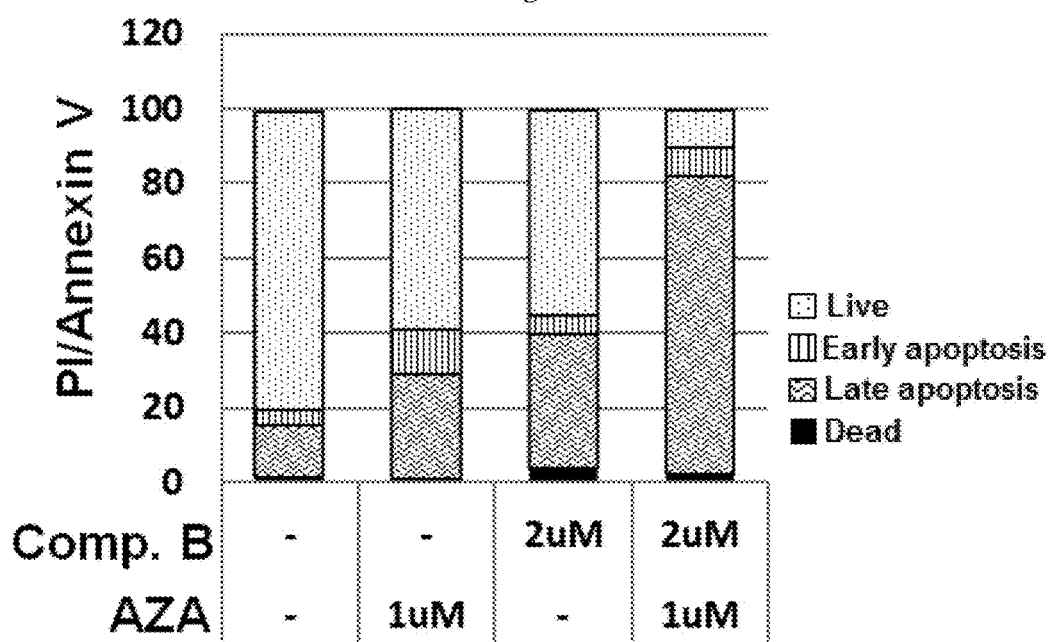
Figure 7C:
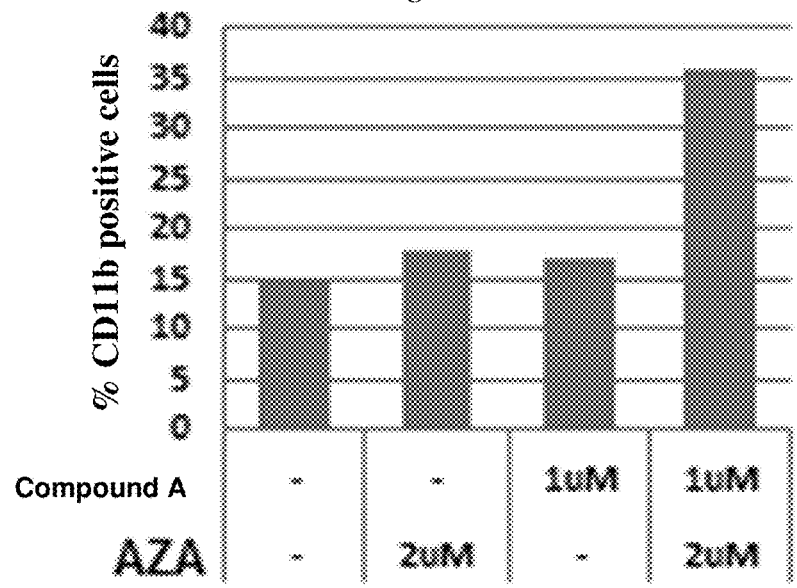
Figure 7D:
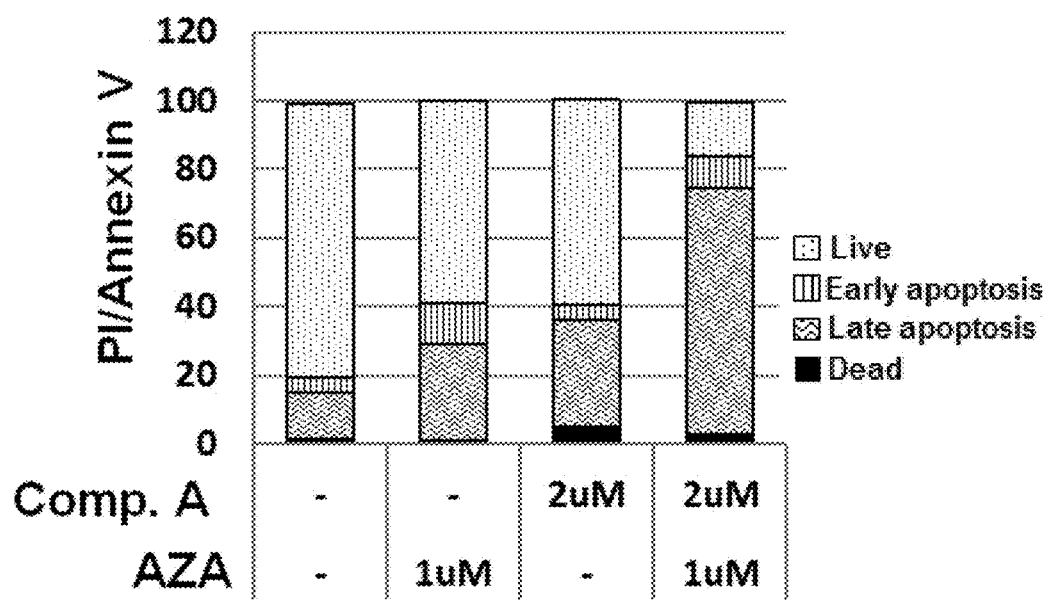
Figure 7E:
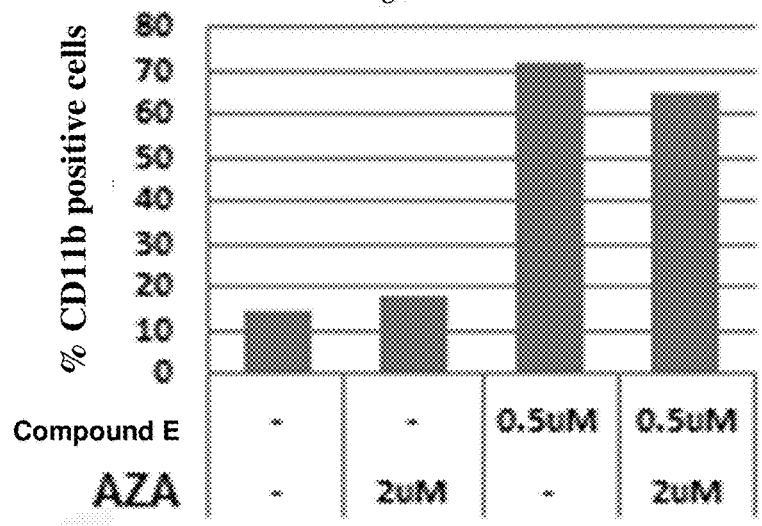
Figure 7F:
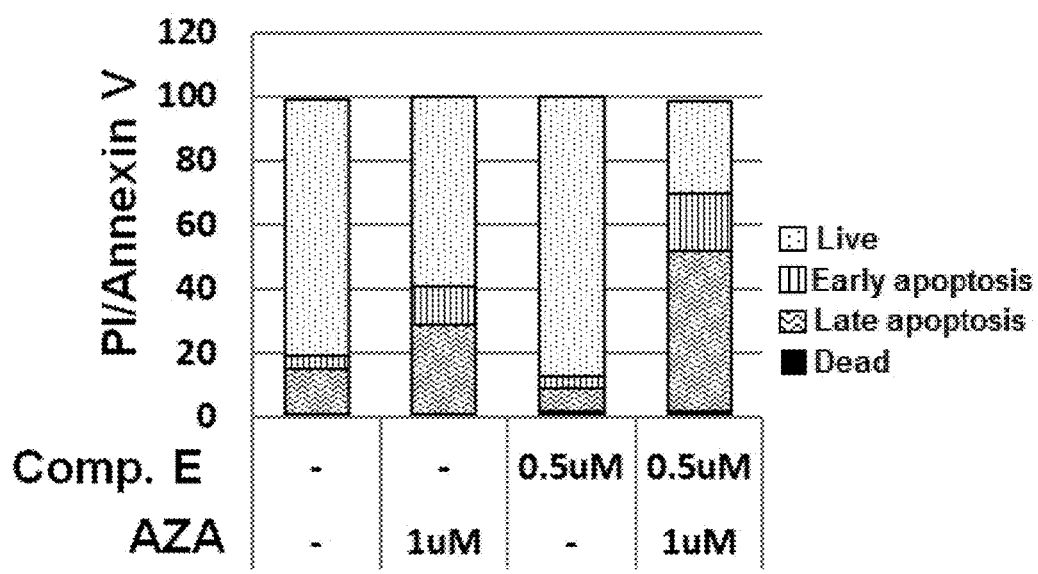

FIGS. 7A-F show the combination of HDAC inhibitors and azacitidine in the NB4 cell line. Briefly, cells were treated with DMSO, Compound B, Compound A, or Compound E as single agent or in combination with azacitidine at the indicated concentrations. Surface levels of CD11b were determined 72 hours post-treatment (FIGS. 7A, 7C, 7E), and apoptosis was assessed 96 hours post-treatment (FIGS. 7B, 7D, 7F). The combination of Compound B or Compound A with azacitidine resulted in synergistic increases of CD11b positive cells (FIGS. 7A, 7C). The combination of Compound B, Compound A, or Compound E with azacitidine resulted in synergistic increases of apoptotic cells compared to single agent treatment (FIGS. 7B, 7D, 7F). Thus, the data in FIGS. 7A-F show that the treatment of NB4 cells with Compound B, Compound A, or Compound E plus azacitidine significantly induced differentiation and apoptosis.

HDAC inhibitors selective for HDAC1/2 showed the strongest cellular activities. Furthermore, HDAC inhibitors reduced the level of AML1-ETO fusion protein, which is essential for the survival of cell lines carrying this fusion protein. The potential of the drug combination is being explored in animal models of AML and in primary AML cells. Together, these findings provide support for the clinical evaluation of selective HDAC inhibitors in combination with azacitidine in AML patients.

Example 12

HDAC1/2 Inhibition Reduces Cell Viability

The following HDAC inhibitors were used to evaluate the relationship between HDAC selectivity and the viability of AML cell lines upon exposure to the HDAC inhibitor:

| Compounds | Structure | Selectivity | Class |
|---|---|---|---|
| Compound E | 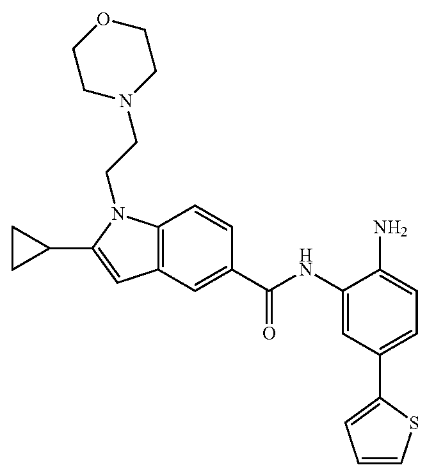 [SMILES: Nc1ccc(-c2cccs2)cc1NC(=O)c1ccc2c(c1)cc(C1CC1)n2CCN1CCOCC1] | HDAC1/2 | Benzamide |
| Compound H | 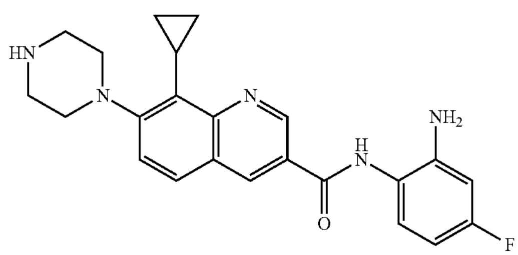 [SMILES: Nc1cc(F)ccc1NC(=O)c1cnc2c(C3CC3)c(N3CCNCC3)ccc2c1] | HDAC3 | Benzamide |
| Compound C | 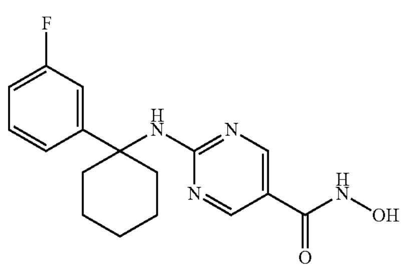 [SMILES: O=C(NO)c1cnc(NC2(c3cccc(F)c3)CCCCC2)nc1] | HDAC6 | Hydroxamate |
| Compound A (ricolinostat) | 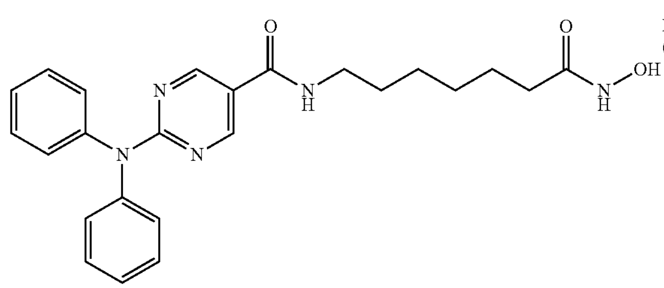 | HDAC6 (1/2/3) | Hydroxamate |

| Compounds | Structure | Selectivity | Class |
|---|---|---|---|
| Compound B | 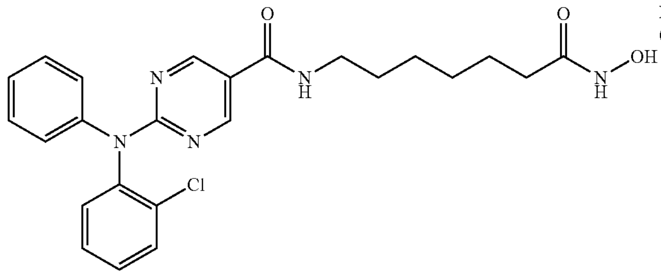 | HDAC6 (1/2/3) | Hydroxamate |
| Compound G | 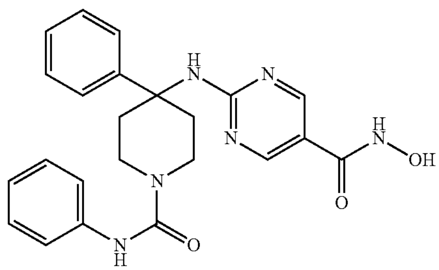 [SMILES: O=C(NO)c1cnc(NC2(c3ccccc3)CCN(C(=O)Nc3ccccc3)CC2)nc1] | HDAC6 (1/2) | Hydroxamate |

The above panel includes an HDAC3 selective inhibitor, Compound H, which is described in U.S. application Ser. No. 14/169,732, and is incorporated herein in its entirety:

Compound H

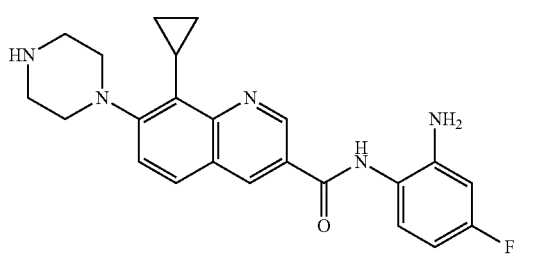

$IC_{50}$(nM) HDAC1 = >2000 HDAC2 = 589 HDAC3 = 57

Figure 8A:
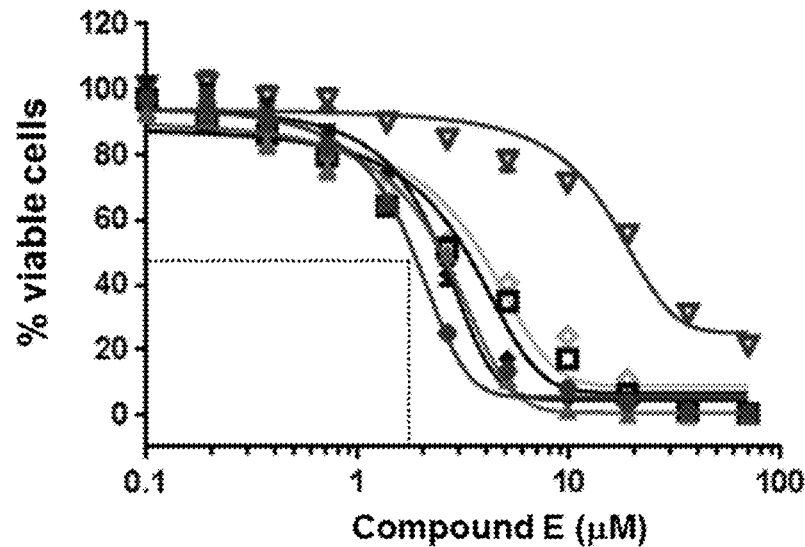
FIGS. 8A-F show exposure of AML cell lines to increasing doses of Compound E (FIG. 8A), Compound H (FIG. 8B), Compound C (FIG. 8C), Compound A (FIG. 8D), Compound B (FIG. 8E) and Compound G (FIG. 8F) for 72 h to confirm their sensitivity to HDAC inhibition. 6 AML cell lines were used in this study: HL-60 (large filled circles), NB4 (upright filled triangles), Kasumi-1 (small filled diamonds), MV4-11 (open squares), THP-1 (open upside-down triangles), and MOLM-13 (open diamonds).
Figure 8B:
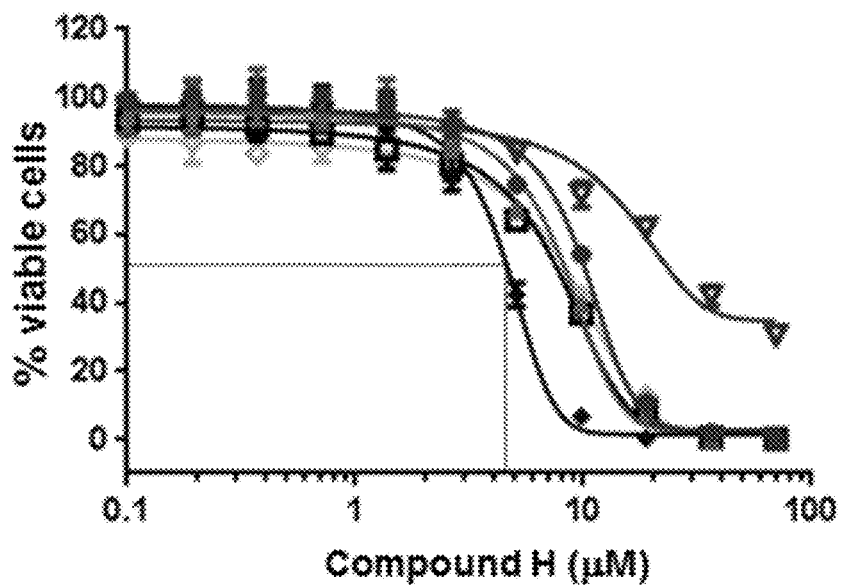
Figure 8C:
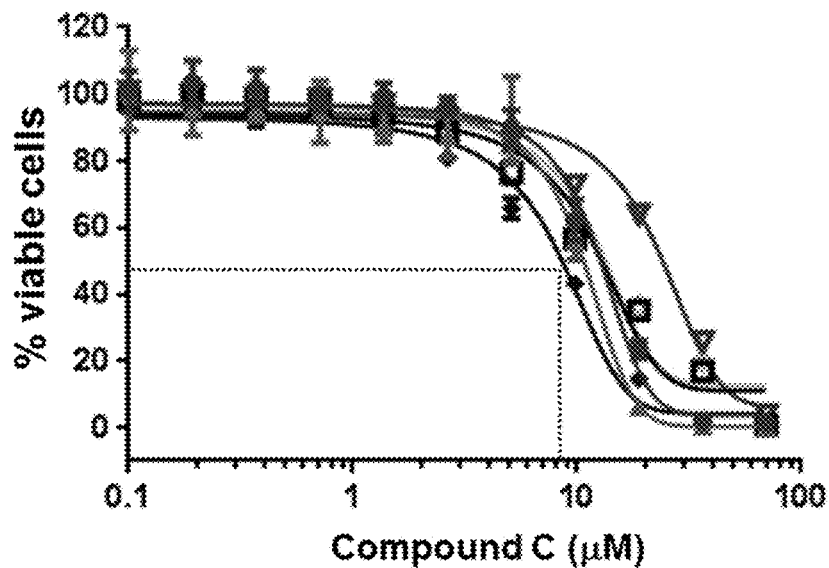
Figure 8D:
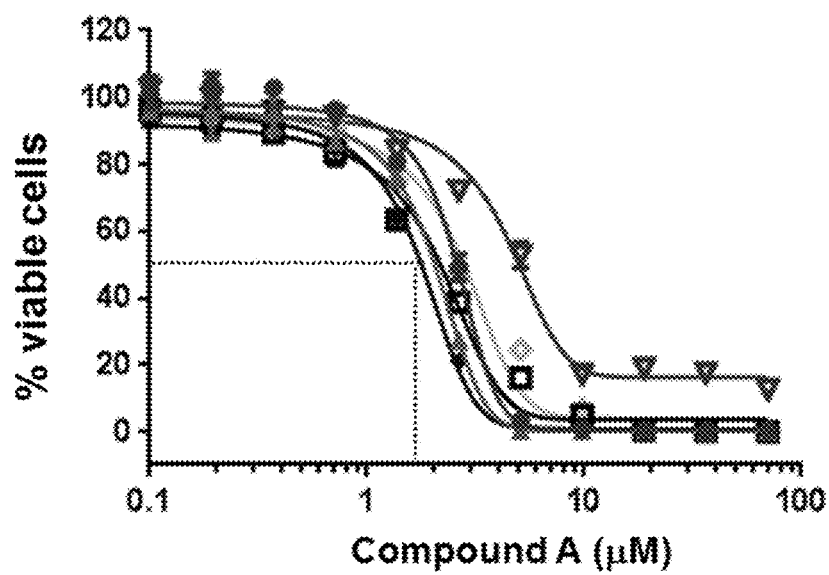
Figure 8E:
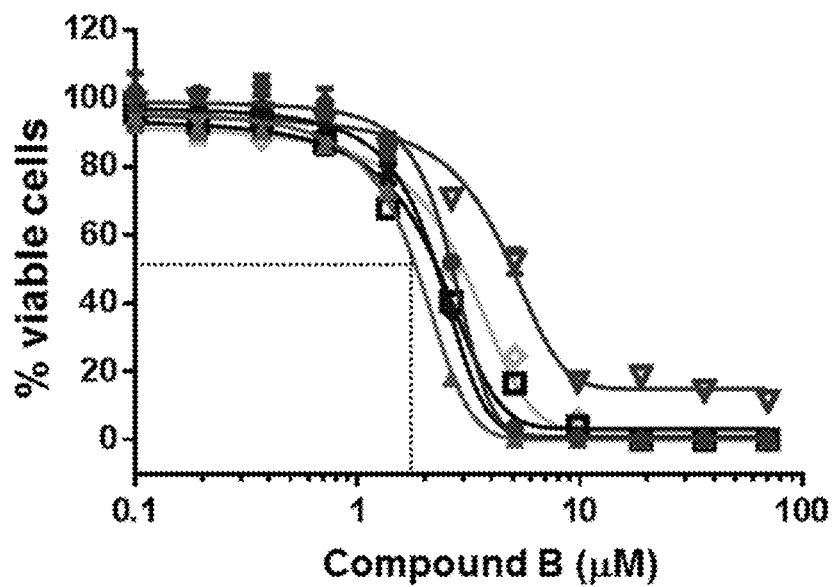
Figure 8F:
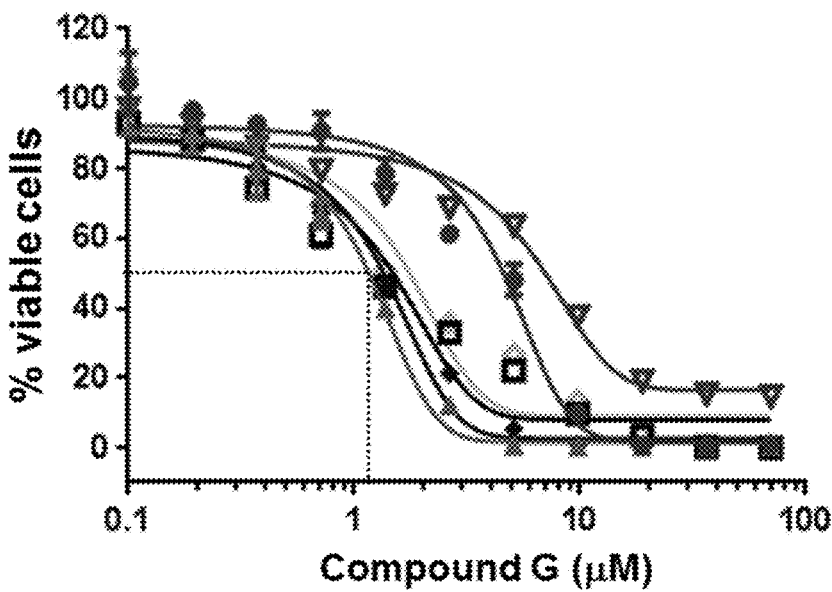

FIGS. 8A-F show the single agent activity on viability in AML cell lines. Briefly, each of the following cell lines: HL-60, NB4, MV4-11, Kasumi-1, THP-1, and MOLM-13 were exposed to increasing doses of either Compound E (FIG. 8A), Compound H (FIG. 8B), Compound C (FIG. 8C), Compound A (FIG. 8D), Compound B (FIG. 8E), and Compound G (FIG. 8F) for 72 hours to confirm their sensitivity to HDAC inhibition. Viability was calculated as a percentage of control (DMSO treated cells). Growth inhibition curves were generated using GraphPad Prism 6. The $IC_{50}$ of Compound E is within its HDAC1/2 selective range (FIG. 8A). The $IC_{50}$ of Compound A and Compound G has some inhibitory effects on HDAC1/2 at their $IC_{50}$ values (FIGS. 8D and 8F). The $IC_{50}$ of Compound C and Compound H is beyond its selective range for HDAC6 and HDAC3, respectively, and likely has an inhibitory effect on HDAC1/2 (FIGS. 8C and 8B). Together, these data indicate HDAC1/2 inhibition reduces cell viability.

Example 13

Figure 9A:
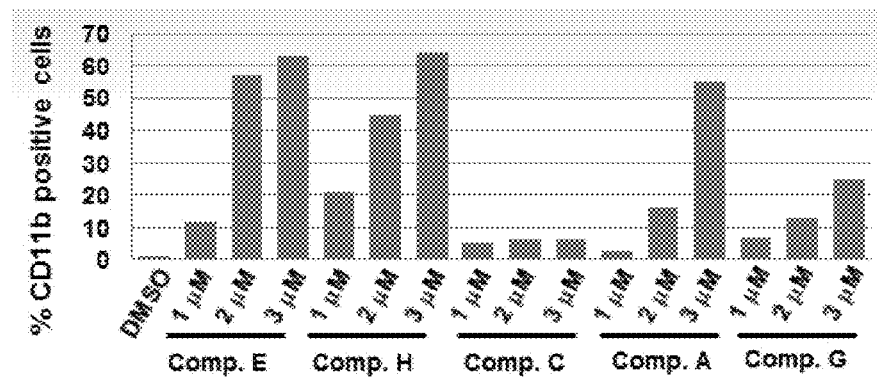
FIGS. 9A-C show treatment of MV4-11 with the indicated doses of compounds.
Figure 9B:
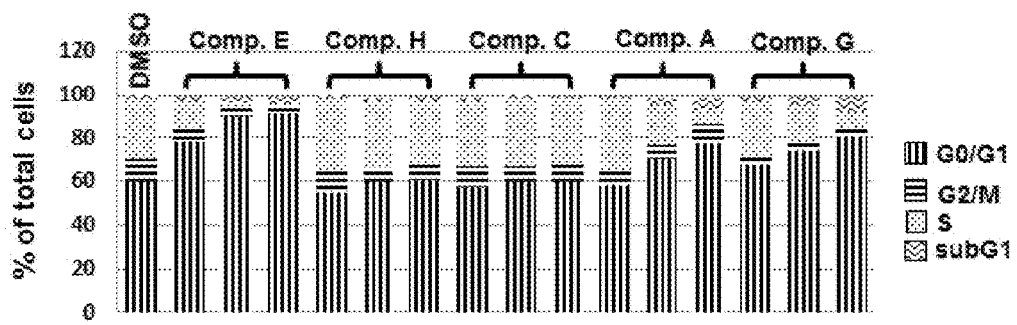
Figure 9C:
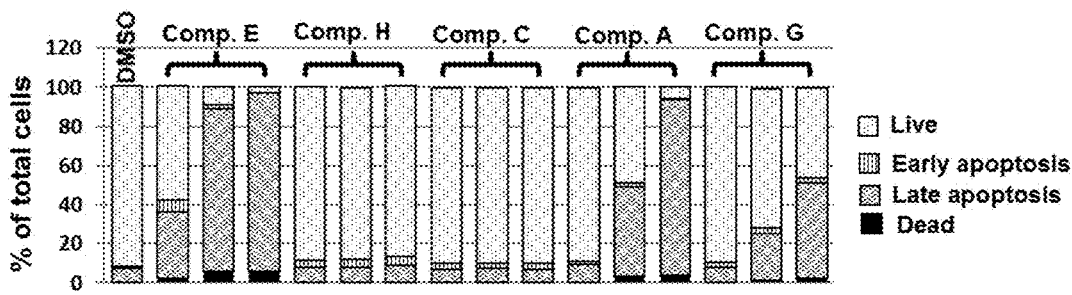

HDAC1/2 Inhibition is Sufficient to Induce Differentiation, Cell Cycle Arrest, and Apoptosis FIGS. 9A-C shows treatment of MV4-11 with the indicated doses of compounds. FIG. 9A shows surface levels of myeloid differentiation marker CD11b, determined by FACS at 72 h post-treatment. Compound E, Compound H, Compound A, and Compound G increased the percentage of CD11b positive cells. Compound C had no effect on CD11b positive cells. FIG. 9B shows assessment of the cell cycle by flow cytometry after incorporation of EdU and staining with Far Red at 72 h post-treatment. The distribution of cells among G0/G1 phase, G2/M phase, S phase and subG1 phase was determined. Compound E, Compound A, and Compound G induced cell cycle arrest. FIG. 9C shows the assessment of apoptosis by flow cytometry via measuring Annexin V binding and cellular permeability to propidium iodide at 96 h post-treatment. The relative fraction of cells that were live, in early apoptosis, in late apoptosis, or dead was then determined. Treatment with Compound E, Compound A, and Compound G resulted in an increase in apoptosis relative to control cells.

In summary, HDAC1/2 inhibition is sufficient to induce differentiation, cell cycle arrest and apoptosis in AML cell lines. HDAC3 inhibition induces differentiation marker CD11b only (i.e., had no effect on cell cycle and apoptosis). Selective HDAC6 inhibition has no obvious impact or effect.

Example 14

HDAC1/2 Inhibition Induces Differentiation and Apoptosis in AML Cells

Figure 10A:
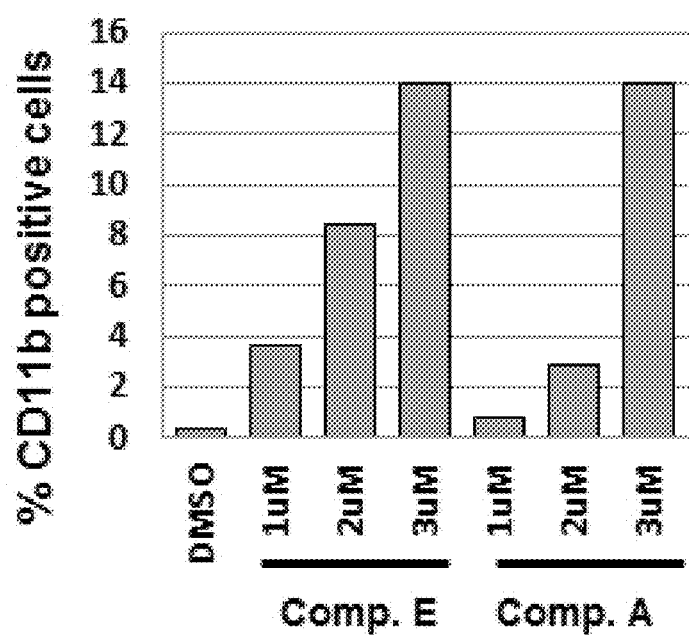
FIGS. 10A-F show the treatment of the following AML cell lines: Kasumi-1 (FIGS. 10A and 10B), HL-60 (FIGS. 10C and 10D) and NB4 (FIGS. 10E and 10F), with indicated doses of compounds.
Figure 10B:
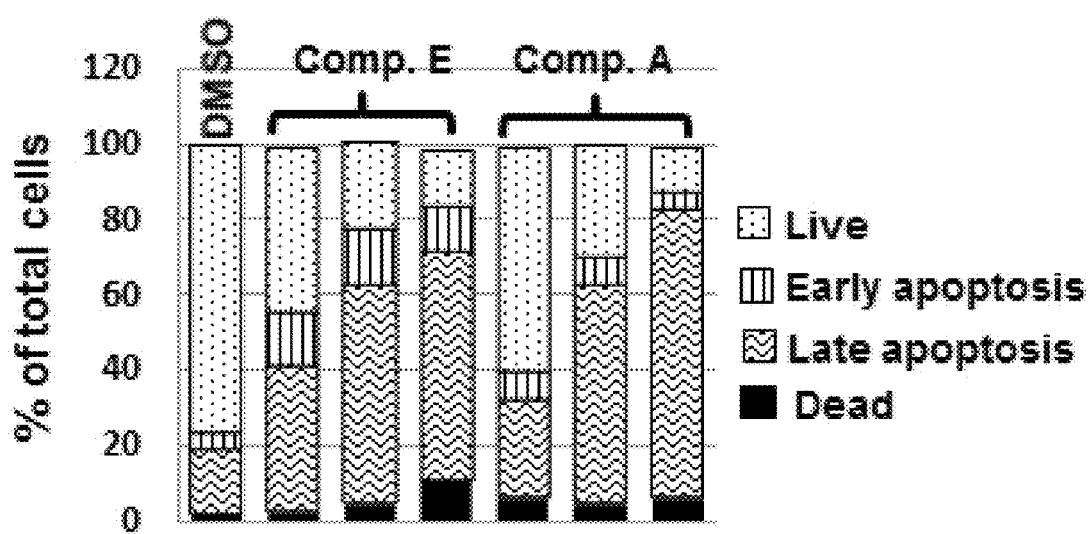
Figure 10C:
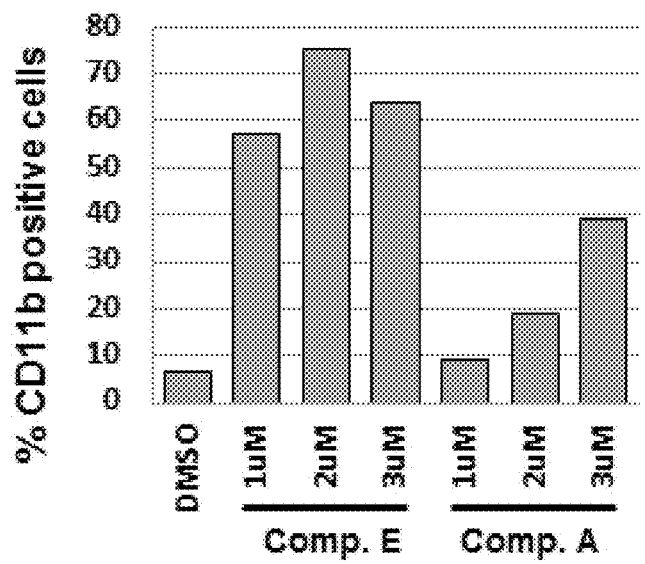
Figure 10D:
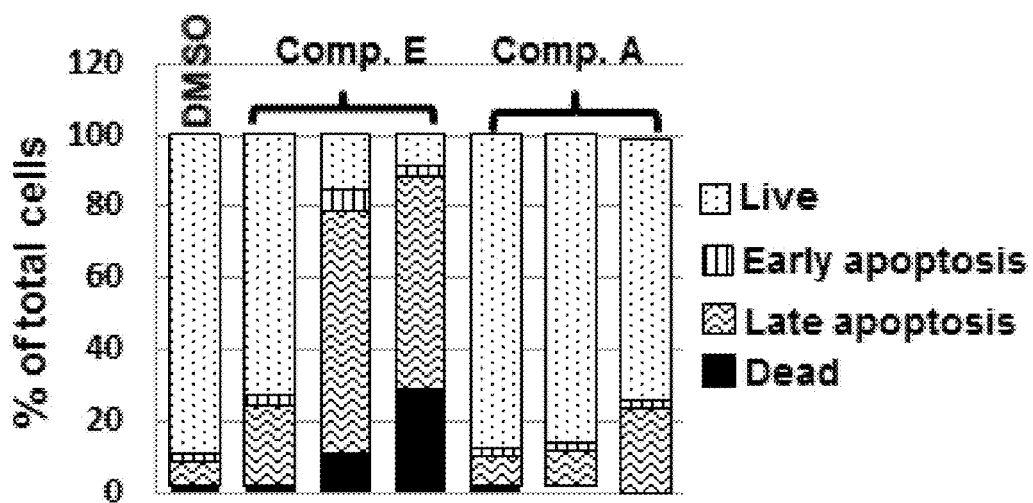
Figure 10E:
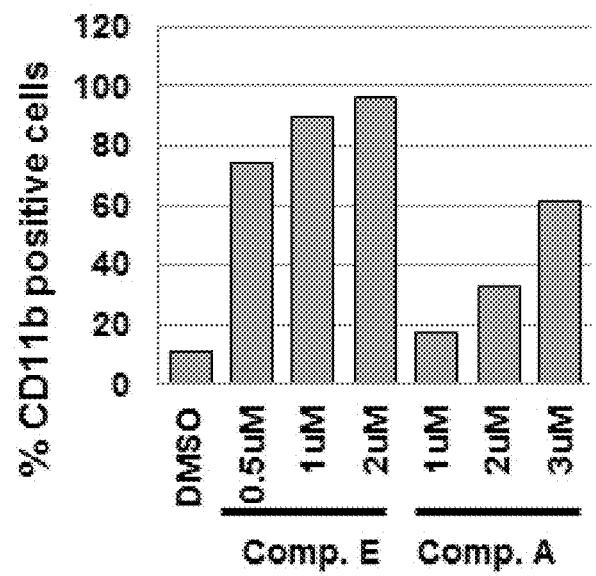
Figure 10F:
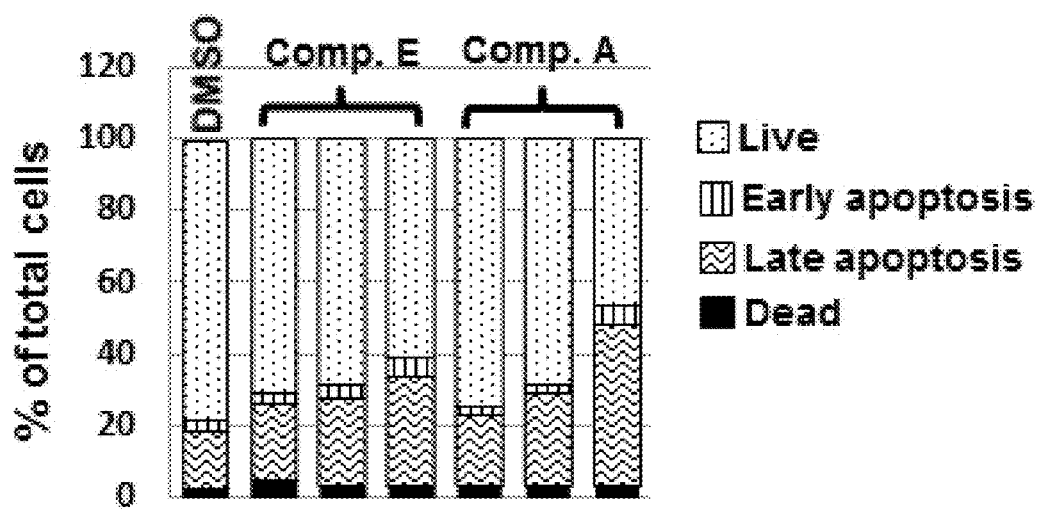
Figure 11A:
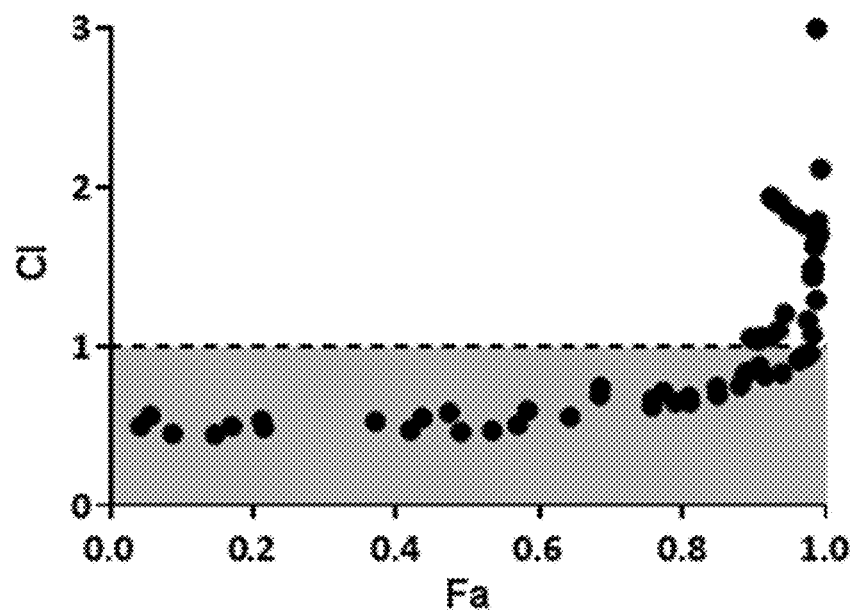
FIGS. 11A-D show that combinations of HDAC1/2 inhibition with azacitidine result in synergistic decreases in HL-60 cell viability. HL-60 cells were treated with increasing doses of azacitidine with Compound E (FIG. 11A) or with Compound A (FIG. 11B) or with Compound H (FIG. 11C) or with Compound C (FIG. 11D), and cell viability was assessed at 72 hr by cell titer glo assay. The combination index (CI) and relative fraction affected (Fa) was determined at each dose level using CalcuSyn software. The measurement of CI values less than 1 (shaded region) strongly support a synergistic interaction between drugs.
Figure 11B:
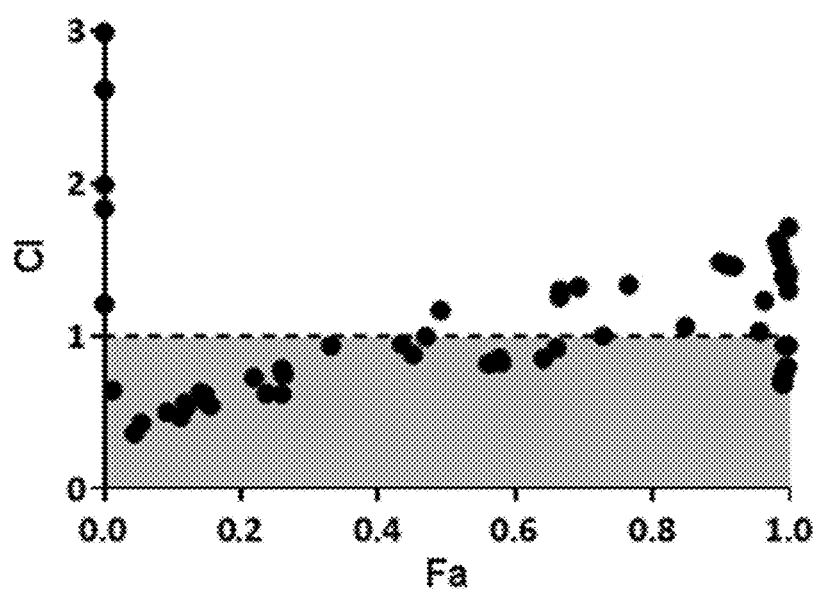
Figure 11C:
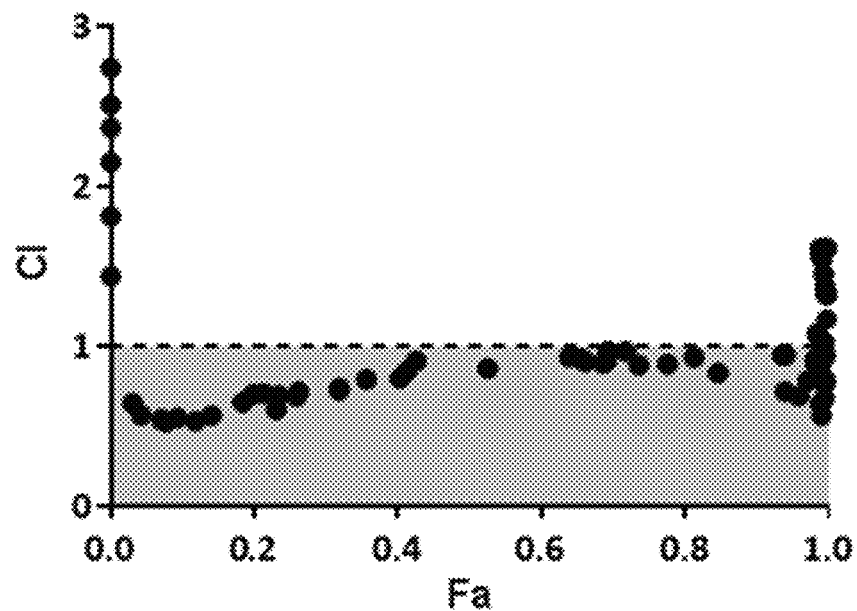
Figure 11D:
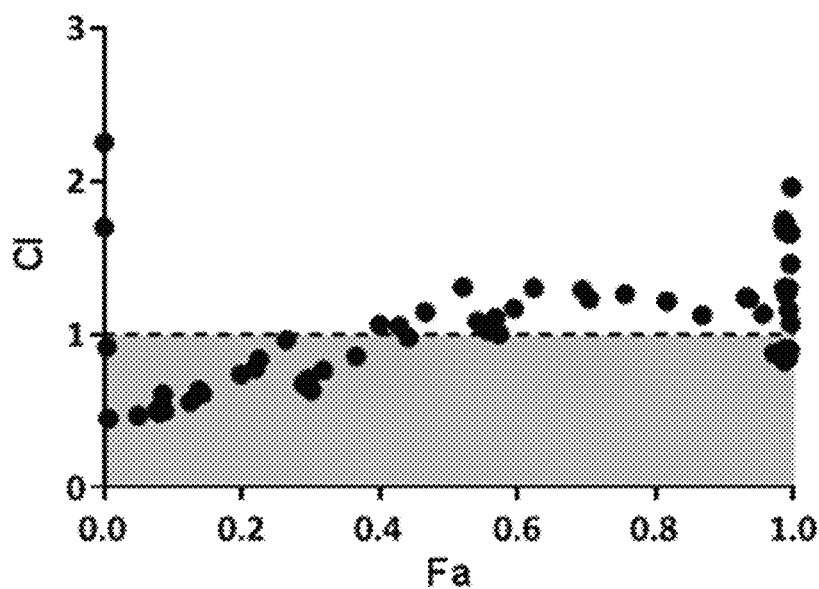

FIGS. 10A-F show the treatment of the following AML cell lines: Kasumi-1 (FIGS. 10A and 10B), HL-60 (FIGS. 10C and 10D) and NB4 (FIGS. 10E and 10F), with indicated doses of compounds. FIGS. 10A, 10C, and 10E show surface levels of myeloid differentiation marker CD11b determined by FACS at 72 h post-treatment. Compound E and Compound A increased percentage of CD11b positive cells in all three cell lines. FIGS. 10B, 10D, and 10F show the assessment of apoptosis by FACS (see, e.g., FIG. 9C).

Treatment with Compound E and Compound A resulted in increased apoptosis relative to control cells. Further, Compound E and Compound A induced differentiation and apoptosis in a dose-dependent manner in all three cell lines described.

Example 15

HDAC1/2 Inhibition Synergizes with Azacitidine in HL-60 Cells

FIGS. 11A-D show that combinations of HDAC1/2 inhibition with azacitidine result in synergistic decreases in HL-60 cell viability. HL-60 cells were treated with increasing doses of azacitidine with Compound E (FIG. 11A) or with Compound A (FIG. 11B) or with Compound H (FIG. 11C) or with Compound C (FIG. 11D), and cell viability was assessed at 72 hr by cell titer glo assay. The combination index (CI) and relative fraction affected (Fa) was determined at each dose level using CalcuSyn software. The measurement of CI values less than 1 (shaded region) strongly support a synergistic interaction between drugs. Significant enhancement of azacitidine activity is observed in combination with HDAC1/2 inhibition. Compound E showed the strongest synergistic interaction with azacitidine.

Example 16

HDAC1/2 Inhibition Enhances Activity of Azacitidine

Figure 12A:
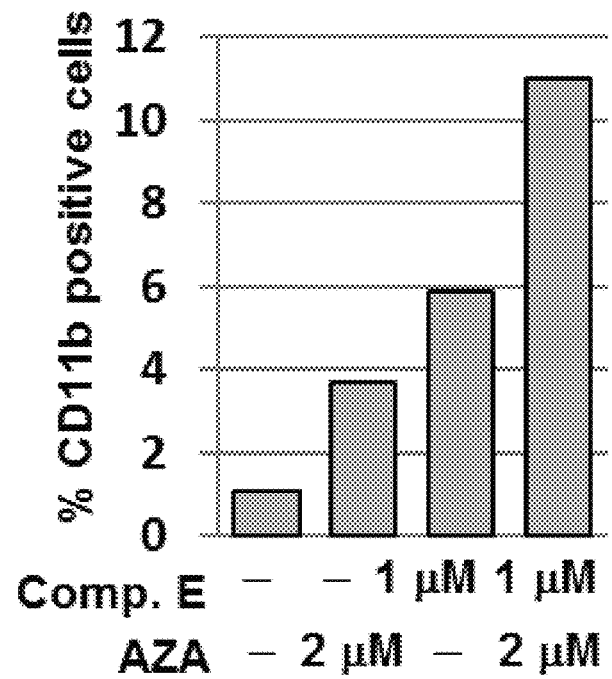
FIGS. 12A-F show the treatment of MV4-11 cells with Compound E or with Compound A or with Compound B as single agent or in combination with azacitidine at indicated doses.
Figure 12B:
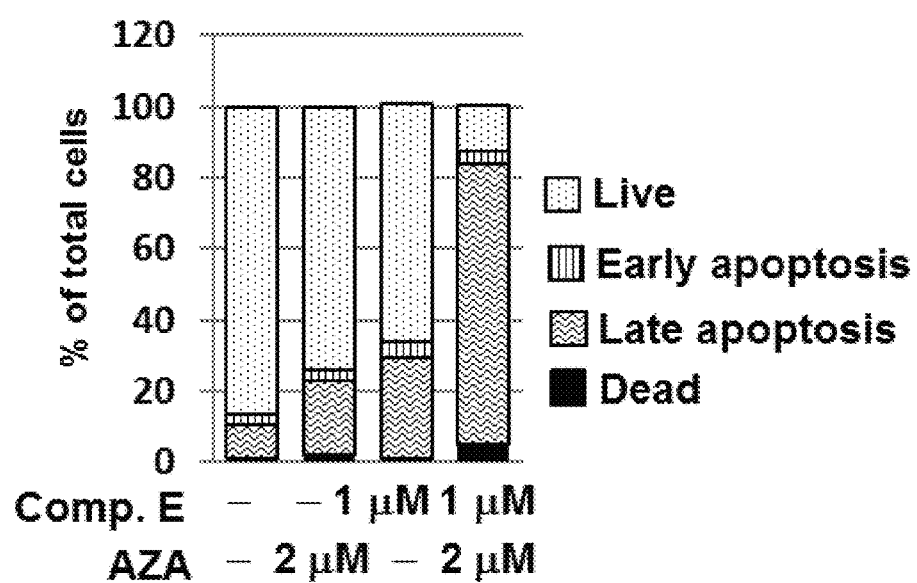
Figure 12C:
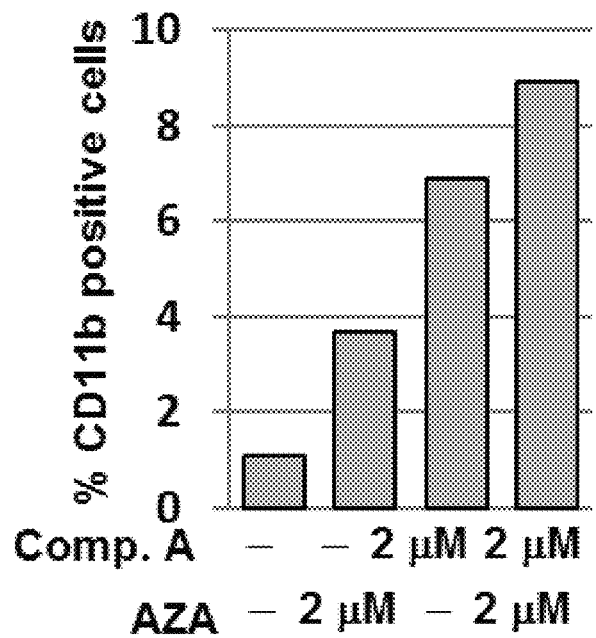
Figure 12D:
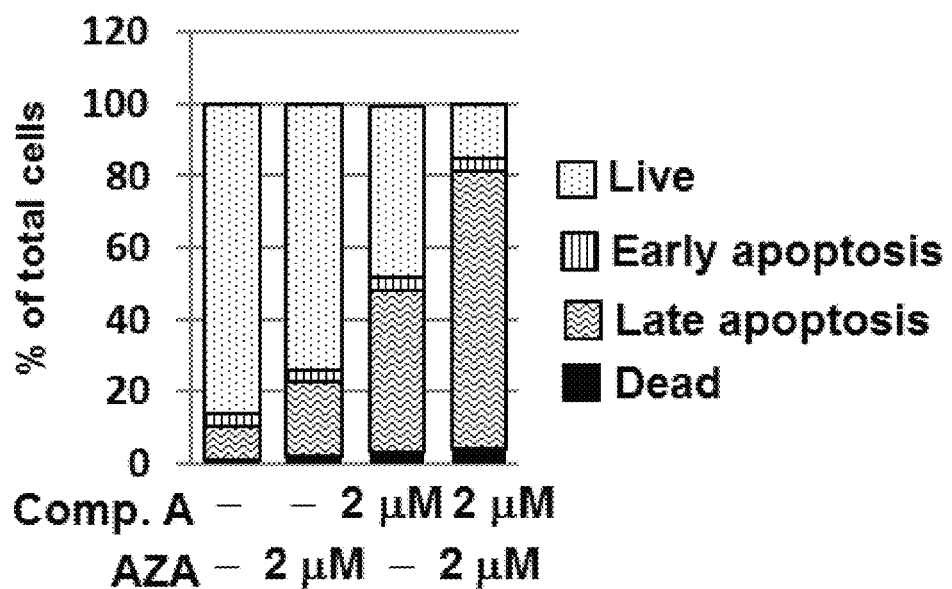
Figure 12E:
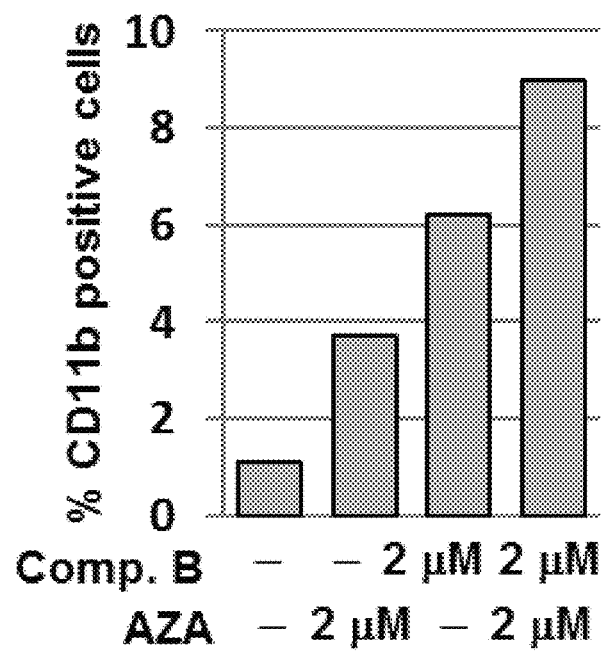
Figure 12F:
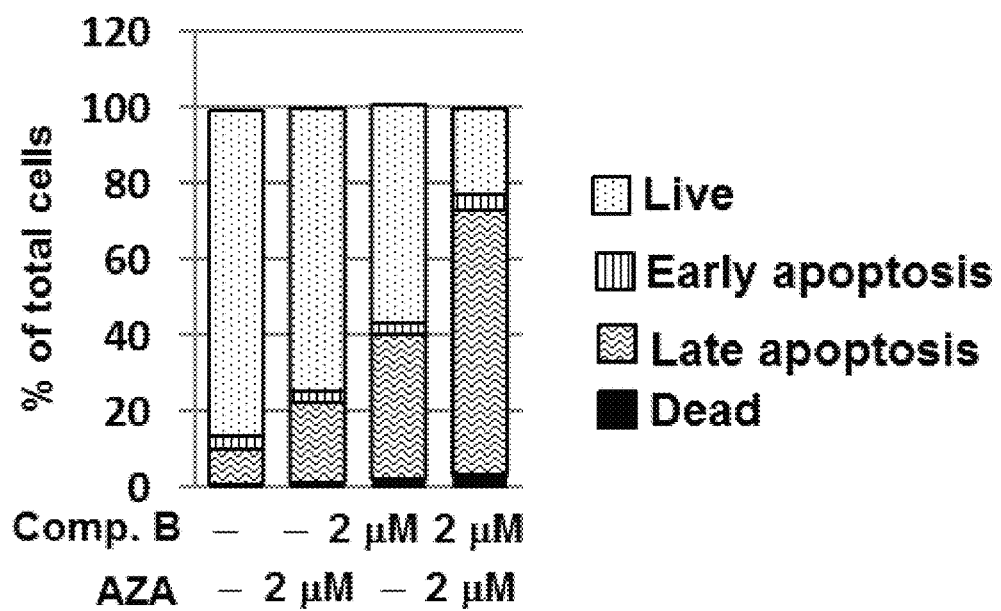

FIG. 12A-F show the treatment of MV4-11 cells with azacitidine plus Compound E or plus Compound A or plus Compound B significantly induced differentiation and apoptosis. MV4-11 cells were treated with Compound E or with Compound A or with Compound B as single agent or in combination with azacitidine at indicated doses. FIGS. 12A, 12C, and 12E show surface levels of CD11b determined by FACS at 72 h post-treatment. FIGS. 12B, 12D, and 12F show assessment of apoptosis by FACS (as in, e.g., FIG. 9C) at 96 h post-treatment.

Combination of Compound E with azacitidine, Compound A with azacitidine and Compound B with azacitidine resulted in further increase of percentage of CD11b positive cells and enhanced induction of apoptosis greater than either single agent. As described above, this example shows significant enhancement of azacitidine activity in combination with HDAC1/2 inhibition.

Example 17

Compound a Enhanced Tumor Growth Inhibition by Azacitidine

Figure 13A:
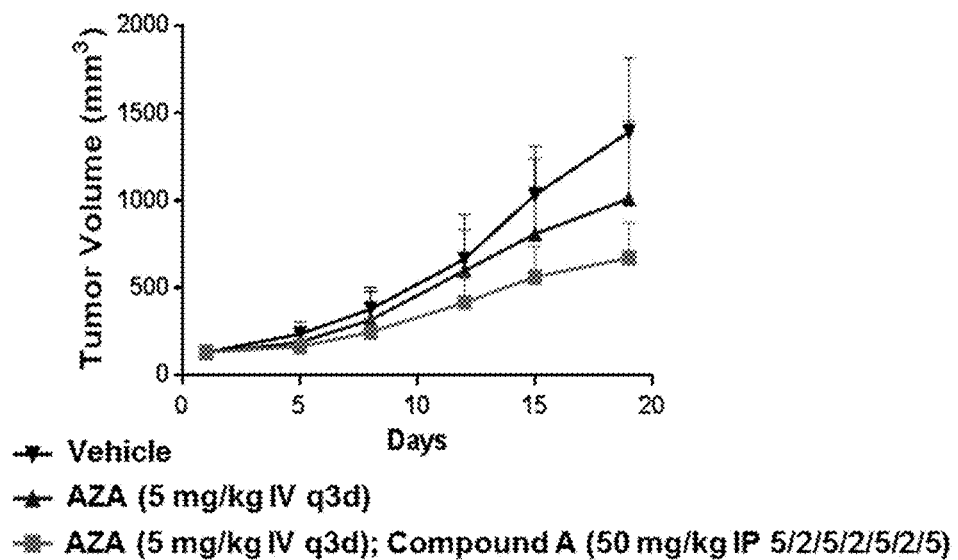
FIG. 13A shows that treatment with Compound A plus azacitidine reduced tumor growth in vivo as compared to treatment with azacitidine or vehicle alone.
Figure 13B:
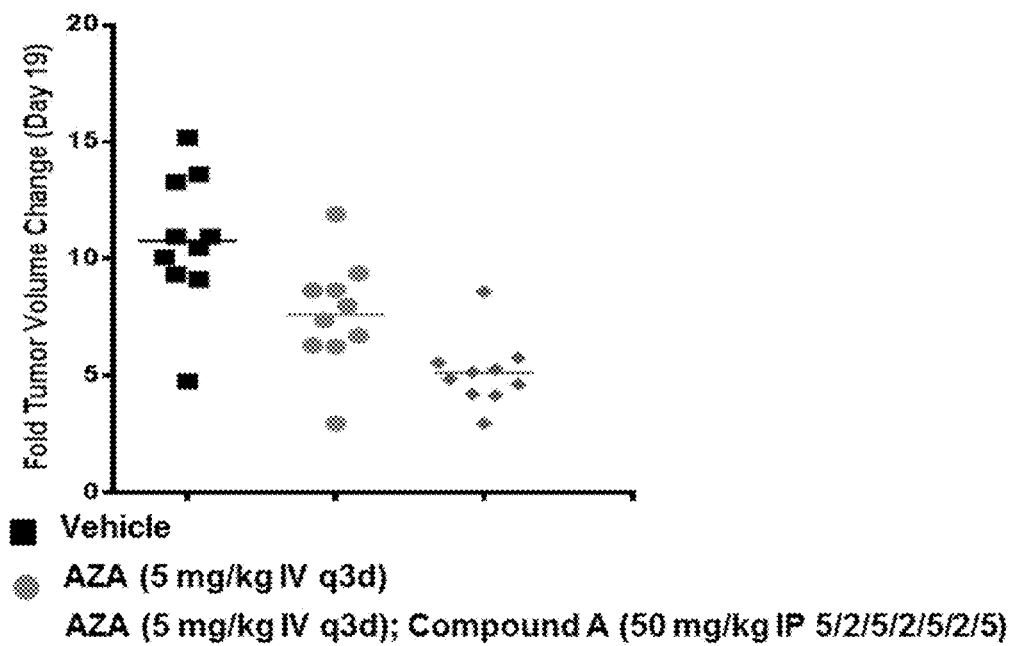
FIG. 13B shows that treatment with Compound A plus azacitidine reduced the fold tumor volume change as compared to treatment with azacitidine or vehicle alone.
Figure 13C:
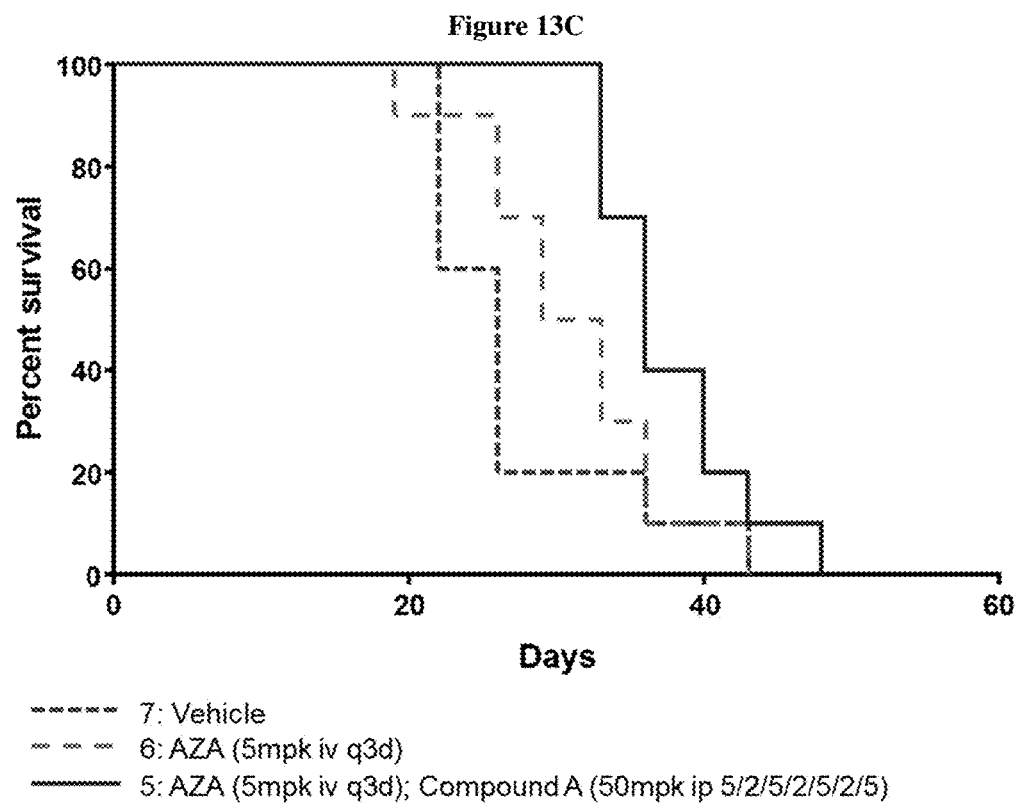
FIG. 13C shows that treatment with Compound A plus azacitidine increased survival in vivo as compared to treatment with azacitidine or vehicle alone.
Figure 14A:
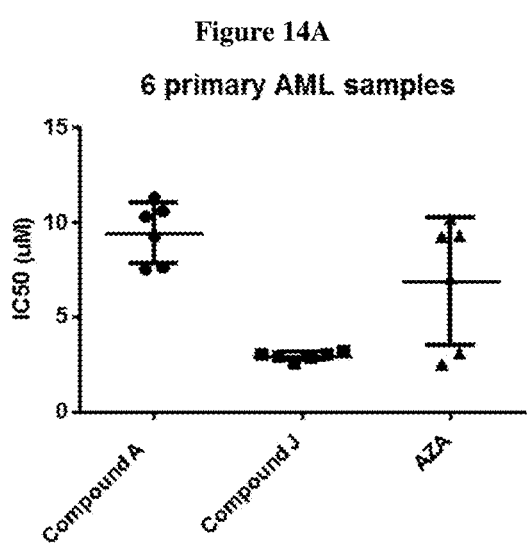
FIG. 14A shows the $IC_{50}$ values of Compound A, Compound J and azacitidine on inhibiting colony formation in 6 bone marrow samples derived from AML patients.
Figure 14B:
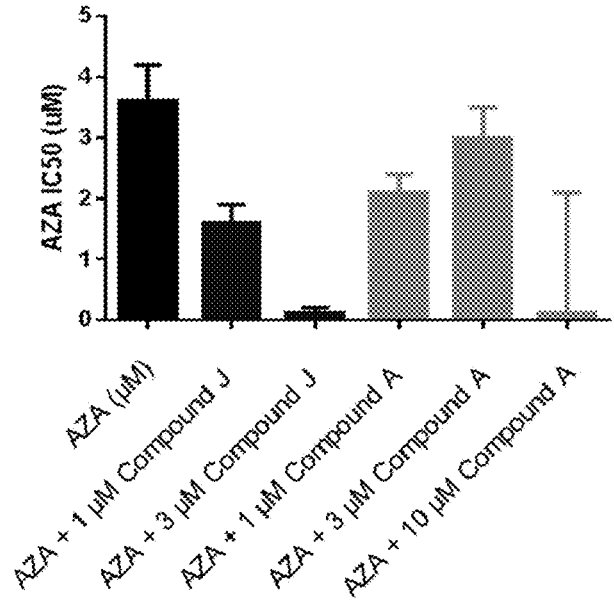
FIG. 14B shows the effect of HDAC1/2 inhibition alone and in combination with azacitidine on colony formation of the primary AML patient sample 4031113SH.
Figure 14C:
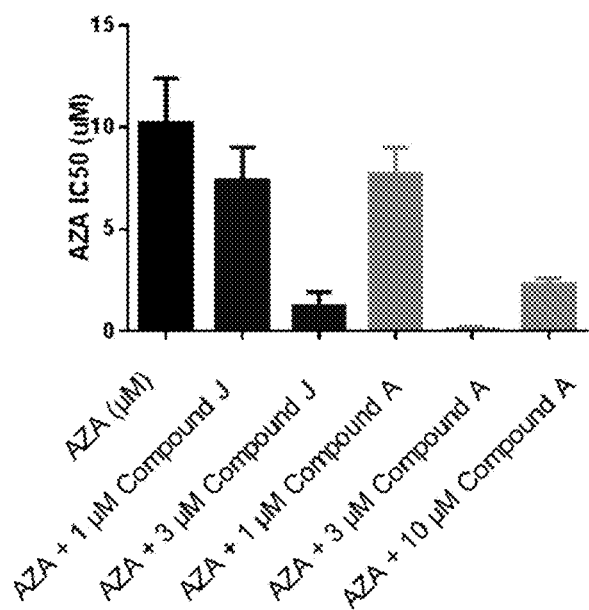
FIG. 14C shows the effect of HDAC1/2 inhibition alone and in combination with azacitidine on colony formation of the primary AML patient sample VMBM0007.
Figure 14D:
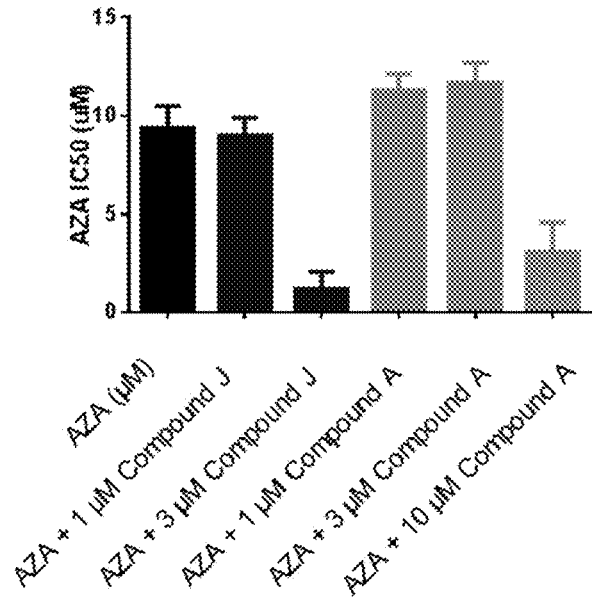
FIG. 14D shows the effect of HDAC1/2 inhibition alone and in combination with azacitidine on colony formation of the primary AML patient sample 184090514.
Figure 14E:
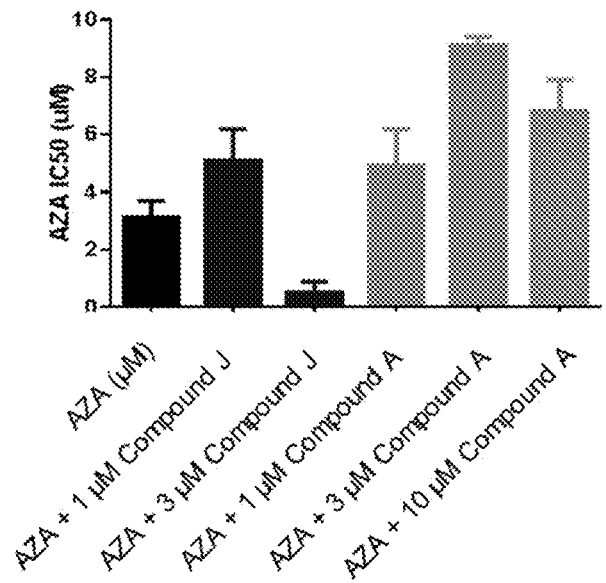
FIG. 14E shows the effect of HDAC1/2 inhibition alone and in combination with azacitidine on colony formation of the primary AML patient sample 103113SH.

FIGS. 13A-C show that treatment with Compound A plus azacitidine reduces tumor growth in vivo. Ncr nu/nu mice implanted with MV4-11 cells were treated with vehicle, azacitidine (5 mg/kg IV q3d), or azacitidine (5 mg/kg IV q3d) plus Compound A (50 mg/kg IP 5/2/5/2/5/2/5) for up to 4 weeks. (A) Tumor volume was measured twice weekly and the mean tumor volume±SD is plotted. (B) Fold tumor volume change on day 19 relative to day 1 is plotted. (C) Survival curve was plotted. Single agent azacitidine reduced tumor growth and increased survival of MV4-11. This effect was further enhanced by addition of Compound A.

Example 18

HDAC1/2 Inhibition Enhanced the Activity of Azacitidine in pPrimary AML Sample Colony Formation Assay FIG. 14A-E, shows that HDAC1/2 inhibition alone and in combination with azacitidine reduces colony formation of primary AML patient samples. (A) 6 bone marrow samples derived from AML patients were cultured in methylcellulose-based medium and treated with increasing concentrations of Compound A, Compound J and azacitidine for 14 days when the colonies reach reasonable size. IC50 values for each drug are plotted. The median IC50 values for Compound A, Compound J and azacitidine are 9.76 uM, 2.95 uM and 8.11 uM, respectively. The relative potency of the three drugs are Compound J>azacitidine>Compound A. (B-E) Each bone marrow sample from AML patient was treated with increasing concentrations of azacitidine alone or in the presence of Compound J at 1 uM or 3 uM or Compound A at 1 uM, 3 uM or 10 uM. IC50 values were plotted for each patient sample. For sample 4031113SH (B) and sample VMBM0007 (C), Compound J and Compound A decreased azacitidine IC50 value, indicating a good combination effect of HDAC1/2 inhibition with azacitidine on these primary AML cell growth. For sample 184090514 (D), Compound J at 3 uM and Compound A at 10 uM, the concentrations close to their IC50 values, significantly reduced azacitidine IC50 value, indicating a good combination effect. For sample 103113SH (E), only Compound J at 3 uM reduced azacitidine IC50. Together, Compound J is more potent on inhibiting primary AML cell growth than Compound A and azacytidine. Compound J at the concentrations close to or below its own IC50 value significantly reduced IC50 value of azacitidine on all 4 primary AML cell colony formation.

Example 19

Ex Vivo Pharmacological Profiling of Azacitidine, Compound A and Compound J

Figure 15A:
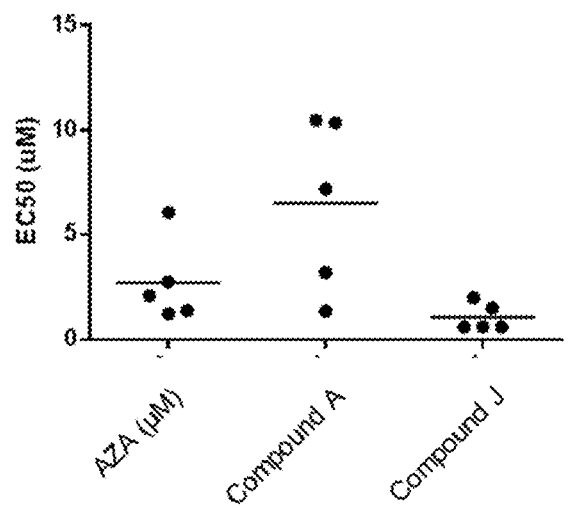
FIG. 15A shows the $IC_{50}$ values of azacitidine, Compound A and Compound J on inhibiting proliferation of AML blast freshly derived from bone marrow of AML patients.
Figure 15B:
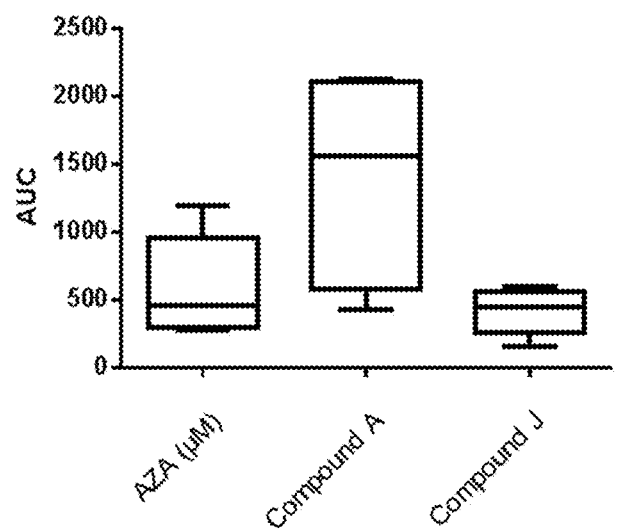
FIG. 15B shows the AUC (area under the curve) values for azacitidine, Compound A and Compound J on inhibiting proliferation of AML blast freshly derived from bone marrow of AML patients.
Figure 15C:
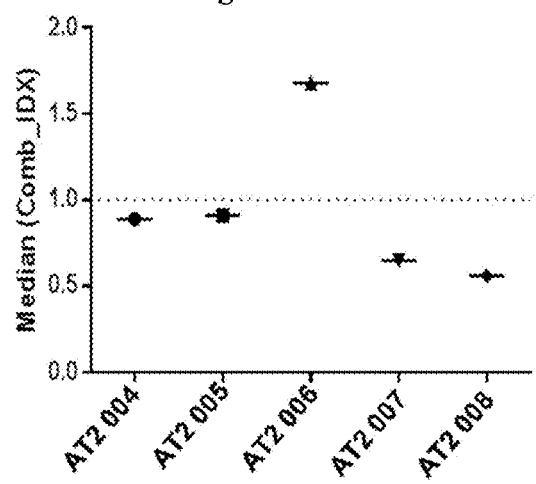
FIG. 15C shows that the combination of azacitidine with Compound J results in a synergistic interaction between the two drugs on inhibiting proliferation of primary AML cells freshly derived from AML patients in 4 out of 5 bone marrow samples.

FIG. 15A-C, shows that HDAC1/2 inhibition alone and in combination with azacitidine inhibit proliferation of AML blast freshly derived from bone marrow of AML patients. (A-B), 5 bone marrow samples derived from AML patients were treated with increasing concentrations of azacitidine, Compound A and Compound J and live AML cells were quantified by flow cytometry at 96 h. IC50 values (A) and AUC values (B) were plotted. The median IC50 values for Compound A, Compound J and azacitidine are 7.2 uM, 0.6 uM and 2.1 uM, respectively. The relative potency of the three drugs are Compound J>azacitidine>Compound A, consistent with the result in FIG. 2. (C) 5 bone marrow samples derived from AML patients were treated with increasing doses of azacitidine with Compound J and live AML cells were quantified by flow cytometry at 96 h. The combination index (Comb IDX) were calculated and median Comb IDX values were plotted. In 4 out of 5 samples, the Comb IDX value is less than 1, supporting a synergistic interaction between the two drugs on inhibiting proliferation of primary AML cells freshly derived from AML patients.

Example 20

Gene Expression Profiling

MV4-11 cells were plated at 2×10⁵ cells/ml and treated with azacitidne at 1 µM, Compound E at 1 µM, Compound E at 2 µM, azacitidine at 1 µM plus Compound E at 1 µM, azacitidine at 1 µM plus Compound E at 2 µM for 24 h and 48 h. Cells were collected and RNA isolated. RNA samples were subjected to Affymetrix PrimeView Gene Expression profiling. Azacitidine at 1 µM and Compound E at 2 µM at 48 h were the focus of the initial data analysis. Molecular signatures were analyzed by GSEA (http://www.broadinstitute.org/gsea/index.jsp). The genes and signatures that were upregulated by the single and combination treatment are significantly more than those that were downregulated, consistent with the mechanisms of the compounds. In order to identify pathways and/or genes that mediate the combinatorial effects of azacitidine with Compound E, signatures and genes that were upregulated by single agent and further upregulated by combination treatment were identified. Signatures including apoptosis and CEBPA pathway, a major transcription factor driving differentiation, are among the top pathways and/or genes identified. More than 60 genes including GATA2 and CD86 follow this expression pattern.

Example 21

Induction of GATA2 Expression in MV4-11 AML Cell Line

Figure 16:
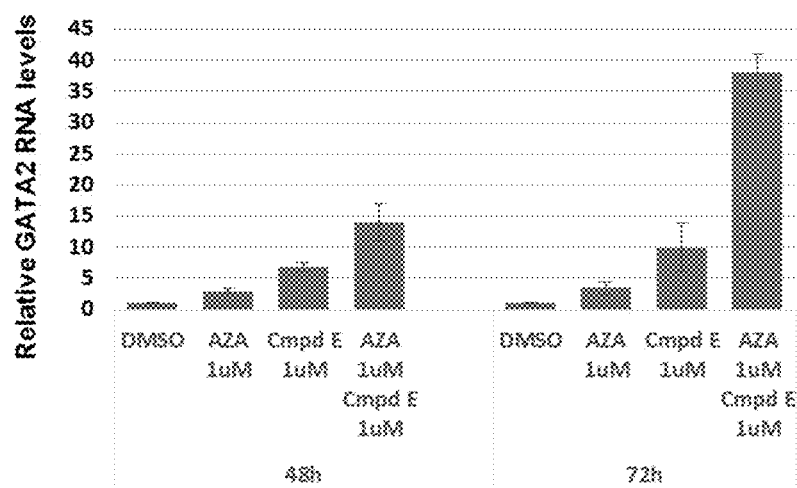
FIG. 16 shows Compound E and azacitidine synergistically induce GATA2 expression in MV4-11 AML cells.
Figure 17A:
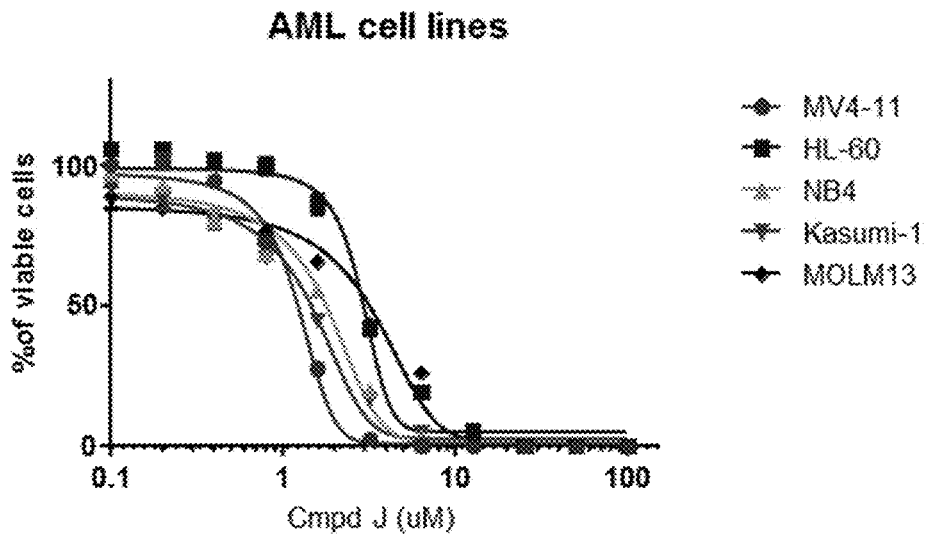
FIG. 17A shows that various AML cell lines are sensitive to HDAC1/2 inhibition.
Figure 17B:
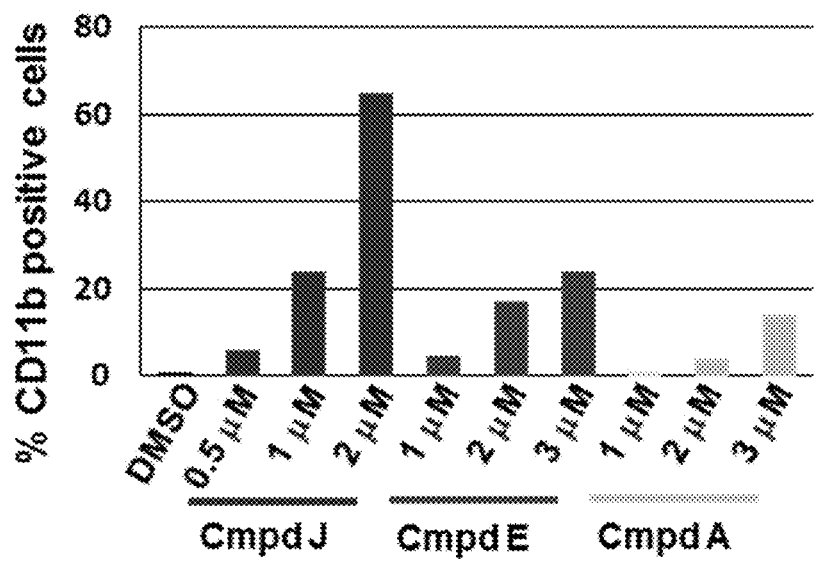
FIG. 17B shows the surface levels of myloid differentiation marker CD11b in MV4-11 (AML) cells as determined by FACS after 72 hours of treatment with the indicated compound.
Figure 17C:
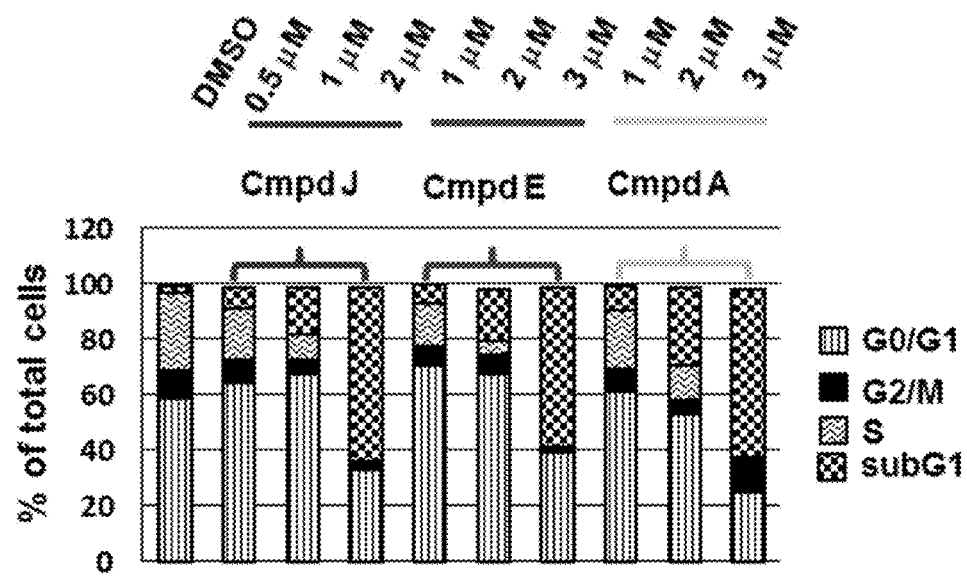
FIG. 17C shows a cell cycle assessment in MV4-11 (AML) cells as determined by flow cytometry after 72 hours of treatment with the indicated compound.
Figure 17D:
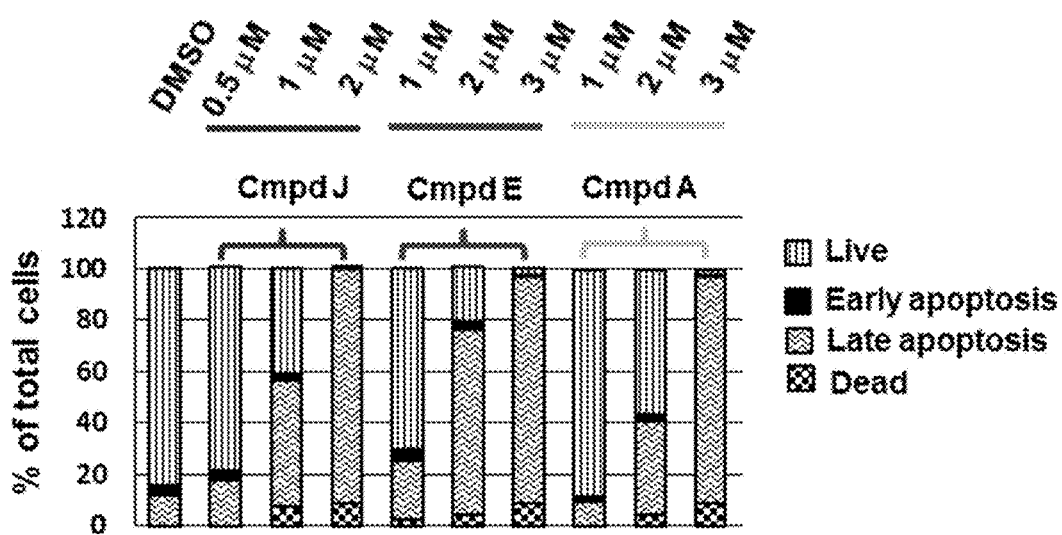
FIG. 17D shows the relative fraction of MV4-11 (AML) cells that were live, in early apoptosis, in late apoptosis or dead as assessed by flow cytometry after 72 hours of treatment with the indicated compound.

FIG. 16. Treatment of Compound E plus azacitidine significantly induced Gata2 in MV4-11 cells. (A-B) MV4-11 cells were plated at 2×10⁵ cells/ml at indicated doses for 48 h and 72 h. RNA was prepared and analyzed for GATA2 and GAPDH as internal control. Azacitidine at 1 uM and Compound E at 1 uM induced GATA2 level as single agent at 48 h and 72 h. Combination of azacitidine and Compound E further induced GATA2 expression at both time points.

Example 22

Single Agent Activity in AML Cell Lines

FIG. 17. Compound J reduces cell viability, induces CD11b and apoptosis in AML cells. (A) Indicated AML cell lines were exposed to increasing concentrations of Compound J to confirm their sensitivity to HDAC1/2 inhibition. (B-D) MV4-11 cells were treated with indicated concentrations of compounds. (B) Surface levels of myeloid differentiation marker CD11b were determined by FACS at 72 h post-treatment. Compound J showed the highest potency increasing percentage of CD11b positive cells. (C) Cell cycle was assessed by flow cytometry after incorporation of EdU and staining with Far Red at 72 h post-treatment. The distribution of cells among G0/G1 phase, G2/M phase, S phase and subG1 phase was determined. Compound J, Compound E and Compound A induced cell cycle arrest as well as apoptosis. (D) Apoptosis was assessed by flow cytometry via measuring Annexin V binding and cellular permeability to propidium iodide at 96 h post-treatment. The relative fraction of cells that were live, in early apoptosis, in late apoptosis or dead was then determined. Treatment with Compound J, Compound E, and Compound A resulted in increase in apoptosis relative to control cells.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments provided herein described herein. Such equivalents are intended to be encompassed by the following claims.

What is claimed is:

1. A pharmaceutical combination for treating leukemia comprising a therapeutically effective amount of a histone deacetylase 6 (HDAC6)-specific inhibitor, and azacitidine or a pharmaceutically acceptable salt thereof, wherein the HDAC6-specific inhibitor is a compound of Formula I:

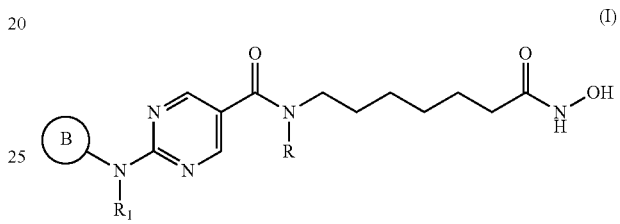

or a pharmaceutically acceptable salt thereof,
wherein,
ring B is phenyl;
R₁ is phenyl, which may be optionally mono-substituted with a halide; and
R is H.

2. The combination of claim 1, wherein the leukemia is acute myelogenous leukemia (AML).

3. The combination of claim 1, wherein the compound of Formula I is:

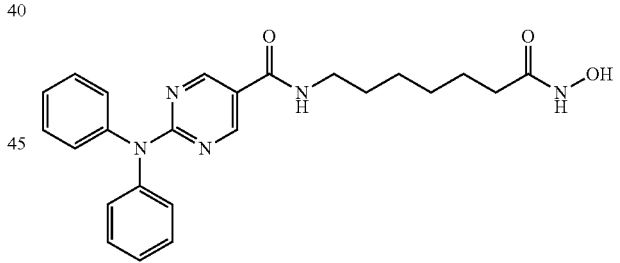

or a pharmaceutically acceptable salt thereof.

4. The combination of claim 1, wherein the compound of Formula I is:

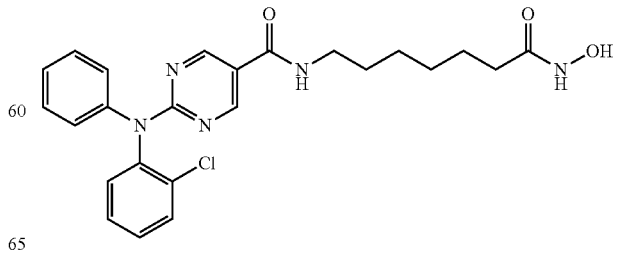

or a pharmaceutically acceptable salt thereof.

5. A pharmaceutical combination for treating leukemia comprising a therapeutically effective amount of a histone deacetylase 6 (HDAC6)-specific inhibitor, and azacitidine or a pharmaceutically acceptable salt thereof, wherein the HDAC-6 specific inhibitor is:

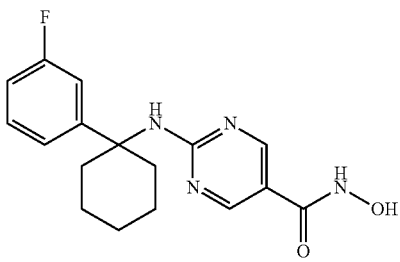 [SMILES: O=C(NO)c1cnc(NC2(c3cccc(F)c3)CCCCC2)nc1]

or a pharmaceutically acceptable salt thereof.

6. The combination of claim 1, wherein the combination further comprises a pharmaceutically acceptable carrier.

7. A method for treating acute myelogenous leukemia (AML) in a subject in need thereof comprising administering to the subject a therapeutically effective amount of a histone deacetylase 6 (HDAC6)-specific inhibitor, and azacitidine or a pharmaceutically acceptable salt thereof, wherein the HDAC6-specific inhibitor is a compound of Formula I:

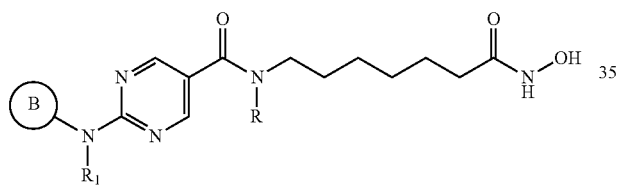

or a pharmaceutically acceptable salt thereof,
wherein,
ring B is phenyl;
$R_1$ is phenyl, which may be optionally mono-substituted with a halide; and
R is H.

8. The method of claim 7, wherein the compound of Formula I is:

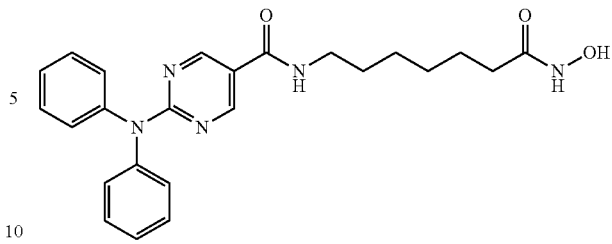

or a pharmaceutically acceptable salt thereof.

9. The method of claim 7, wherein the compound of Formula I is:

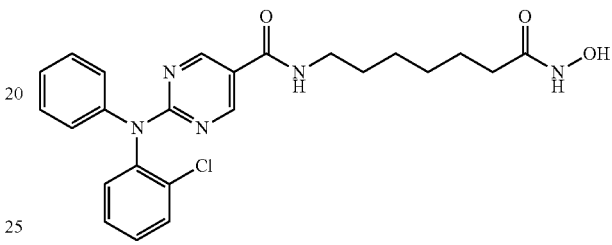

or a pharmaceutically acceptable salt thereof.

10. A method for treating acute myelogenous leukemia (AML) in a subject in need thereof comprising administering to the subject a therapeutically effective amount of a histone deacetylase 6 (HDAC6)-specific inhibitor, and azacitidine or a pharmaceutically acceptable salt thereof, wherein the HDAC-6 specific inhibitor is:

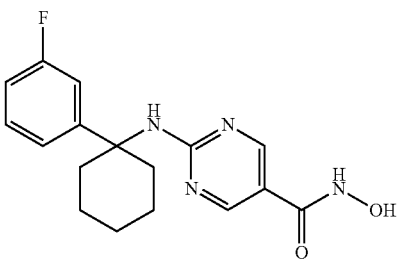 [SMILES: O=C(NO)c1cnc(NC2(c3cccc(F)c3)CCCCC2)nc1]

or a pharmaceutically acceptable salt thereof.

* * * * *